(12) United States Patent
Cummings et al.

(10) Patent No.: US 11,376,278 B2
(45) Date of Patent: Jul. 5, 2022

(54) COMPOSITIONS AND METHODS FOR TREATING DISEASE

(71) Applicant: Sulfilatec, Inc., Huntsville, AL (US)

(72) Inventors: Christopher Cummings, Madison, AL (US); David Shifrin, Nashville, TN (US)

(73) Assignee: Sulfilatec, Inc., Huntsville, AL (US)

( * ) Notice: Subject to any disclaimer, the term of this patent is extended or adjusted under 35 U.S.C. 154(b) by 0 days.

(21) Appl. No.: 16/324,681

(22) PCT Filed: Aug. 11, 2017

(86) PCT No.: PCT/US2017/046415
§ 371 (c)(1),
(2) Date: Feb. 11, 2019

(87) PCT Pub. No.: WO2018/031845
PCT Pub. Date: Feb. 15, 2018

(65) Prior Publication Data
US 2019/0216849 A1 Jul. 18, 2019

Related U.S. Application Data

(60) Provisional application No. 62/373,656, filed on Aug. 11, 2016, provisional application No. 62/402,291, filed on Sep. 30, 2016, provisional application No. 62/402,309, filed on Sep. 30, 2016, provisional application No. 62/424,057, filed on Nov. 18, 2016.

(51) Int. Cl.

| | |
|---|---|
| *A61K 33/14* | (2006.01) |
| *A61P 13/12* | (2006.01) |
| *A61P 9/00* | (2006.01) |
| *A61K 9/00* | (2006.01) |
| *A61K 33/00* | (2006.01) |
| *A61K 45/06* | (2006.01) |
| *G01N 33/84* | (2006.01) |

(52) U.S. Cl.
CPC ............ *A61K 33/14* (2013.01); *A61K 9/0019* (2013.01); *A61K 9/0053* (2013.01); *A61K 33/00* (2013.01); *A61K 45/06* (2013.01); *A61P 9/00* (2018.01); *A61P 13/12* (2018.01); *G01N 33/84* (2013.01)

(58) Field of Classification Search
None
See application file for complete search history.

(56) References Cited

U.S. PATENT DOCUMENTS

| | | | |
|---|---|---|---|
| 5,260,289 | A | 11/1993 | Hyodo et al. |
| 5,716,646 | A | 2/1998 | Smith et al. |
| 6,989,171 | B2 | 1/2006 | Portman |
| 2004/0033292 | A1* | 2/2004 | Portman .................. A23L 2/39 426/72 |
| 2004/0096845 | A1 | 5/2004 | Sakai et al. |
| 2014/0220157 | A1 | 8/2014 | Powers |
| 2016/0175347 | A1* | 6/2016 | Hudson .................. A61K 45/06 424/613 |

FOREIGN PATENT DOCUMENTS

| | | |
|---|---|---|
| WO | 99/34773 | 7/1999 |
| WO | 2005/051383 | 6/2005 |
| WO | 2015/120458 | 8/2015 |
| WO | 2016/014781 | 1/2016 |

OTHER PUBLICATIONS

Sangster et al (Food and Chem Toxicology 21:409-419, 1983—Abstract only) (Year: 1983).*
Boothe et al (J Am Vet Med Assoc 221:1131-1135, 2002) (Year: 2002).*
Strejan GH, Gilbert JJ, St Louis J. Suppression of chronic-relapsing EAE by basic protein-liposome complexes. Prog Clin Biol Res. 1984;146:429-34.
Sundaramoorthy, Munirathinam, et al. "Crystal structure of NC1 domains: Structural basis for type IV collagen assembly in basement membranes." Journal of Biological Chemistry 277.34 (2002): 31142-31153.
Tanaka, Hiroko, et al. "Rapid determination of total bromide in human serum using an energy-dispersive X-ray spectrometer." Biological and Pharmaceutical Bulletin 26.4 (2003): 457-461.
Target Heart Rates Chart www.heart.org/HEARTORG/HealthyLiving/PhysicalActivity/FitnessBasics/Target-Heart-Rates_UCM_434341_Article.jsp, Accessed on Jul. 3, 2020.
Tektas OY, Lutjen-Drecoll E. Structural changes of the trabecular meshwork in different kinds of glaucoma. Exp Eye Res. Apr. 2009;88(4):769-75.
Than ME, Bourenkov GP, Henrich S, Mann K, Bode W. The NC1 dimer of human placental basement membrane collagen IV: does a covalent crosslink exist? Biol Chem. Aug. 2005;386(8):759-66.
Than, Manuel E., et al. "The 1.9-Å crystal structure of the noncollagenous (NC1) domain of human placenta collagen IV shows stabilization via a novel type of covalent Met-Lys cross-link." Proceedings of the National Academy of Sciences 99.10 (2002): 6607-6612.
Thorner, Paul S., et al. "Coordinate gene expression of the a3, a4, and a5 chains of collagen type IV: Evidence from a canine model of X-linked nephritis with a COL4A5 gene mutation." Journal of Biological Chemistry 271.23 (1996): 13821-13828.

(Continued)

*Primary Examiner* — Craig D Ricci
(74) *Attorney, Agent, or Firm* — Baker Donelson

(57) ABSTRACT

Embodiments of the invention provide pharmaceutical compositions and methods for preventing and treating disease and promoting the health in subjects at risk of cardiovascular disease and/or kidney disease. Additional embodiments of the present invention provide compositions and methods useful for treating and preventing a cardiovascular disease or a kidney disease.

5 Claims, 11 Drawing Sheets
Specification includes a Sequence Listing.

(56) References Cited

OTHER PUBLICATIONS

Timpl R, Wiedemann H, van Delden V, Furthmayr H, Kuhn K. A network model for the organization of type IV collagen molecules in basement membranes. Eur J Biochem. Nov. 1981;120(2):203-11.
Torii, Shizuo, et al. "The REM sleep-inducing action of a naturally occurring organic bromine compound in the ancephale isole cat." Psychopharmacologia 29.1 (1973): 65-75.
Trautner, Mads, and Jens Otto Wieth. "Renal excretion of chloride, bromide and thiocyanate during water diuresis." Acta Physiologica Scandinavica 74.4 (1968): 606-615.
Travers, Joshua G., et al. "Cardiac fibrosis: the fibroblast awakens." Circulation research 118.6 (2016): 1021-1040.
Trepanier, L. A., et al. "Therapeutic serum drug concentrations in epileptic dogs treated with potassium bromide alone or in combination with other anticonvulsants: 122 cases (1992-1996)." Journal of the American Veterinary Medical Association 213.10 (1998): 1449-1453.
Tsuge, Kouichiro, Mieko Kataoka, and Yasuo Seto. "Cyanide and thiocyanate levels in blood and saliva of healthy adult volunteers." Journal of Health Science 46.5 (2000): 343-350.
Tuqan, Alia T., et al. "Evaluation of single versus multiple cryogen spray cooling spurts on in vitro model human skin." Lasers in medical science 20.2 (2005): 80-86.
Understanding Blood Pressure Readings www.heart.org/HEARTORG/Conditions/HighBloodPressure/KnowYourNumbers/Understanding-Blood-Pressure-Readings_UCM_301764_Article.jsp, Accessed on Jul. 3, 2020.
United States Pharmacopeial Convention, "Sodium Chloride" monograph, Pharmcopeial Forum, 28(4), Jul.-Aug. 2002.
USRDS, Annual Data Report, 2013.
Van Leeuwen, FX Rolaf, Bart Sangster, and Alfred G. Hildebrandt. "The toxicology of bromide ion." CRC critical reviews in toxicology 18.3 (1987): 189-213.
Van Renterghem, D., et al. "The effect of adding Br or Zn supplements to the dialysate on the concentrations of Br and Zn in the blood of hemodialysed patients." Journal of trace elements and electrolytes in health and disease 6.2 (1992): 105-109.
Vanacore, Roberto M., et al. "A role for collagen IV cross-links in conferring immune privilege to the Goodpasture autoantigen: structural basis for the crypticity of B cell epitopes." Journal of Biological Chemistry 283.33 (2008): 22737-22748.
Vanacore, Roberto M., et al. "Identification of S-hydroxylysyl-methionine as the covalent cross-link of the noncollagenous (NC1) hexamer of the α1α1α2 collagen IV network: a role for the post-translational modification of lysine 211 to hydroxylysine 211 in hexamer assembly." Journal of Biological Chemistry 280.32 (2005): 29300-29310.
Vanacore, Roberto M., et al. "The α1. α2 network of collagen IV: reinforced stabilization of the noncollagenous domain-1 by noncovalent forces and the absence of Met-Lys cross-links." Journal of Biological Chemistry 279.43 (2004): 44723-44730.
Vanacore, Roberto, et al. "A sulfilimine bond identified in collagen IV." Science 325.5945 (2009): 1230-1234.
Vesely, David L. "Family of peptides synthesized in the human body have anticancer effects." Anticancer research 34.4 (2014): 1459-1466.
Vobecký M, Pavelka S, Babický A. Bromide transfer through mother's milk and its impact on the suckling rat. Biol Trace Elem Res. Jan. 2005;103(1):37-48.
Vracko, Rudolf. "Basal lamina scaffold-anatomy and significance for maintenance of orderly tissue structure: a review." The American journal of pathology 77.2 (1974): 313.
Wallaeys B, Cornelis R, Mees L, Lameire N. Trace elements in serum, packed cells, and dialysate of CAPD patients. Kidney Int. Oct. 1986;30(4):599-604.
Wang, Xiaomeng, et al. "Type IV collagens regulate BMP signalling in Drosophila." Nature 455.7209 (2008): 72-77.
Weber, G., et al. "Trace element analysis by PIXE in several biomedical fields." Nuclear Instruments and Methods in Physics Research Section B: Beam Interactions with Materials and Atoms 3.1-3 (1984): 326-331.
Weber, Sabine, et al. "Subunit structure and assembly of the globular domain of basement-membrane collagen type IV." European journal of biochemistry 139.2 (1984): 401-410.
Weil J, Gerzer R, Strom T, Lang RE, Dohlemann C, Knorr D, Bidlingmaier F. Increased plasma cyclic guanosine monophosphate concentrations in children with high levels of circulating atrial natriuretic peptide. Pediatrics. Oct. 1987;80(4):545-8.
Willker, Wieland, et al. "Gradient selection in inverse heteronuclear correlation spectroscopy." Magnetic Resonance in Chemistry 31.3 (1993): 287-292.
Wolf RL, Eadie GS. Reabsorption of bromide by the kidney. Am J Physiol. Nov. 1950;163(2):436-41.
Written Opinion of the International Searching Authority, PCT/US17/46415 Oct. 13, 2017.
Yamane, Mototeru, Akihisa Abe, and Isamu Yanagisawa. "Anticholinesterase action of a bromine compound isolated from human cerebrospinal fluid." Journal of neurochemistry 42.6 (1984): 1650-1654.
Yan, Xiaohe, et al. "Peroxidasin is essential for eye development in the mouse." Human molecular genetics 23.21 (2014): 5597-5614.
Yanagisawa, Isamu, and Haruhisa Yoshikawa. "A bromine compound isolated from human cerebrospinal fluid." Biochimica et Biophysica Acta (BBA)—General Subjects 329.2 (1973): 283-294.
Yanagisawa, Isamu, and Shizuo Torii. "A bromine compound existing in blood." The Tohoku journal of experimental medicine 196.3 (2002): 111-121.
Yap WT, Salvay DM, Silliman MA, Zhang X, Bannon ZG, Kaufman DB, Lowe WL Jr, Shea LD. Collagen IV-modified scaffolds improve islet survival and function and reduce time to euglycemia. Tissue Eng Part A. Nov. 2013;19 (21-22):2361-72.
Yates, John R., et al. "Method to correlate tandem mass spectra of modified peptides to amino acid sequences in the protein database." Analytical chemistry 67.8 (1995): 1426-1436.
Yokota et al. "Bromide supplementation exacerbated the renal dysfunction, injury and fibrosis in a mouse model of Alport syndrome" PLoS One 2017, 12, e0183959.
Yunos, Nor'azim Mohd, et al. "Bench-to-bedside review: chloride in critical illness." Critical care 14.4 (2010): 1-10. Yunos et al., Critical Care, 14:226, 2010.
Yurchenco PD, Furthmayr H. Self-assembly of basement membrane collagen. Biochemistry. Apr. 10, 1984;23 (8):1839-50.
Yurchenco PD. Basement membranes: cell scaffoldings and signaling platforms. Cold Spring Harb Perspect Biol. Feb. 1, 2011;3(2):a004911.
Addison, Wr LT. "The use of sodium chloride, potassium chloride, sodium bromide, and potassium bromide in cases of arterial hypertension which are amenable to potassium chloride." Canadian Medical Association Journal 18.3 (1928): 281.
Akomeah, Franklin, et al. "Effect of heat on the percutaneous absorption and skin retention of three model penetrants." European Journal of Pharmaceutical Sciences 21.2-3 (2004): 337-345.
Aouacheria, Abdel, et al. "Insights into early extracellular matrix evolution: spongin short chain collagen-related proteins are homologous to basement membrane type IV collagens and form a novel family widely distributed in invertebrates." Molecular biology and evolution 23.12 (2006): 2288-2302.
Baird-Heinz, Hope E., et al. "A systematic review of the safety of potassium bromide in dogs." Journal of the American Veterinary Medical Association 240.6 (2012): 705-715.
Barratt, T. Martin, and Mackenzie Walser. "Extracellular fluid in individual tissues and in whole animals: the distribution of radiosulfate and radiobromide." The Journal of clinical investigation 48.1 (1969): 56-66.
Baxter, Joy, and Samir Mitragotri. "Jet-induced skin puncture and its impact on needle-free jet injections: experimental studies and a predictive model." Journal of Controlled release 106.3 (2005): 361-373.
Bevc S, Hojs R, Ekart R, Hojs-Fabjan T. Atherosclerosis in hemodialysis patients: traditional and nontraditional risk factors. Acta Dermatovenerol Alp Pannonica Adriat Dec. 2006;15(4):151-7.

(56) References Cited

OTHER PUBLICATIONS

Bhave, Gautam, et al. "Peroxidasin forms sulfilimine chemical bonds using hypohalous acids in tissue genesis." Nature chemical biology 8.9 (2012): 784-790.
Bojanowicz et al., "The mode of the therapeutic action of the mixture of potassium acetate and potassium bromide in essential hypertension" Zschr. Inn. Med.vol. 16 Dec. 1, 1961.
Borza, Dorin-Bogdan, et al. "Goodpasture autoantibodies unmask cryptic epitopes by selectively dissociating autoantigen complexes lacking structural reinforcement: novel mechanisms for immune privilege and autoimmune pathogenesis." Journal of Biological Chemistry 280.29 (2005): 27147-27154.
Bramson, J., et al. "Enabling topical immunization via microporation: a novel method for pain-free and needle-free delivery of adenovirus-based vaccines." Gene therapy 10.3 (2003): 251-260.
Brodie, Bernard B., Elliott Brand, and Seymour Leshin. "The use of bromide as a measure of extracellular fluid." Journal of Biological Chemistry 130.2 (1939): 555-563.
Burnier, J. V., et al. "Type IV collagen-initiated signals provide survival and growth cues required for liver metastasis." Oncogene 30.35 (2011): 3766-3783.
Canavese, Caterina, et al. "A role for bromine deficiency in sleep disturbances of long-term dialysis patients." American journal of kidney diseases 48.6 (2006): 1018-1019.
Cao, Ruihua, et al. "Association between resting heart rate and n-terminal pro-brain natriuretic peptide in a community-based population study in Beijing." Clinical interventions in aging 10 (2015): 55.
Cheng G, Salerno JC, Cao Z, Pagano PJ, Lambeth JD. Identification and characterization of VPO1, a new animal heme-containing peroxidase Free Radic Biol Med. Dec. 15, 2008;45(12):1682-94.
Cho-Chung, Y. S. "DNA drug design for cancer therapy." Current pharmaceutical design 11.22 (2005): 2811-2823.
Chung, Hye Jin, and Jouni Uitto. "Type VII collagen: the anchoring fibril protein at fault in dystrophic epidermolysis bullosa." Dermatologic clinics 28.1 (2010): 93-105.
Cope, Arthur C., et al. "Amine Oxides. VIII. Medium-sized Cyclic Olefins from Amine Oxides and Quaternary Ammonium Hydroxides1, 2." Journal of the American Chemical Society 82.17 (1960): 4663-4669.
Cortez N, Lucero HA, Vallejos RH. Stromal serine protein kinase activity in spinach chloroplasts. Arch Biochem Biophys May 1, 1987;254(2):504-8. doi: 10.1016/0003-9861(87)90130-5.
Cummings, Christopher F., et al. "Extracellular chloride signals collagen IV network assembly during basement membrane formation." Journal of Cell Biology 213.4 (2016): 479-494.
Daley, William P., and Kenneth M. Yamada. "ECM-modulated cellular dynamics as a driving force for tissue morphogenesis." Current opinion in genetics & development 23.4 (2013): 408-414.
Davis, Nicolynn E., et al. "Enhanced function of pancreatic islets co-encapsulated with ECM proteins and mesenchymal stromal cells in a silk hydrogel." Biomaterials 33.28 (2012): 6691-6697.
Dobbie, J. W., J. K. Lloyd, and C. A. Gall. "Categorization of ultrastructural changes in peritoneal mesothelium, stroma and blood vessels in uremia and CAPD patients." Adv Perit Dial 6.3 (1990): 12.
Eli Lilly and Co. Handbook Pharmacy and Therapeutics, 1920.
Estimated Glomerular Filtration Rate (eGFR) www.kidney.org/atoz/content/gfr, Accessed Jul. 3, 2020.
Fidler, Aaron L., et al. "A unique covalent bond in basement membrane is a primordial innovation for tissue evolution." Proceedings of the National Academy of Sciences 111.1 (2014): 331-336.
Fox, Michael A., et al. "Distinct target-derived signals organize formation, maturation, and maintenance of motor nerve terminals" Cell 129.1 (2007): 179-193.
Fu, Hsueh-Liang, et al. "Discoidin domain receptors: unique receptor tyrosine kinases in collagen-mediated signaling." Journal of Biological Chemistry 288.11 (2013): 7430-7437.
Gilchrist, Thomas L., and Christopher J. Moody. "The chemistry of sulfilimines." Chemical Reviews 77.3 (1977) 409-435.
Glass, Richard S., and John R. Duchek. "The structure of dehydromethionine. An azasulfonium salt." Journal of the American Chemical Society 98.4 (1976): 965-969.
Glibowicka M, Winckler B, Aranlbar N, Schuster M, Hanssum H, Ruterjans H, Passow H. Temperature dependence of anion transport in the human red blood cell. Biochim Biophys Acta. Dec. 22, 1988;946(2):345-58.
Gotenstein, Jennifer R., et al. "The C. elegans peroxidasin PXN-2 is essential for embryonic morphogenesis and inhibits adult axon regeneration " Development 137.21 (2010): 3603-3613.
Gould DB, et al. Mutations in Col4a1 cause perinatal cerebral hemorrhage and porencephaly. Science. May 20, 2005;308(5725):1167-71.
Gould DB, et al. Role of COL4A1 in small-vessel disease and hemorrhagic stroke. N Engl J Med. Apr. 6, 2006;354(14):1489-96.
Gupta, Malini C., Patricia L. Graham, and James M. Kramer. "Characterization of a1 (IV) collagen mutations in Caenorhabditis elegans and the effects of a1 and a2 (IV) mutations on type IV collagen distribution." The Journal of cell biology 137.5 (1997): 1185-1196.
Haenlein, G. F. W., and M. Anke. "Mineral and trace element research in goats: A review." Small Ruminant Research 95.1 (2011): 2-19.
Hasuike, Yukiko, et al. "Accumulation of cyanide and thiocyanate in haemodialysis patients." Nephrology Dialysis Transplantation 19.6 (2004): 1474-1479.
He, Jiang, et al. "Urinary sodium and potassium excretion and CKD progression." Journal of the American Society of Nephrology 27.4 (2016): 1202-1212.
Heart Disease Facts www.cdc.gov/dhdsp/data_statistics/fact_sheets/fs_heart_disease.htm, Accessed on Jul. 3, 2020.
Hudson, Billy G., et al. "Alport's syndrome, Goodpasture's syndrome, and type IV collagen." New England Journal of Medicine 348.25 (2003): 2543-2556.
Hynes, Richard O. "Integrins: bidirectional, allosteric signaling machines." Cell 110.6 (2002): 673-687.
International Search Report, PCT/US17/46415 dated Oct. 13, 2017.
Kay, Lewis, Paul Keifer, and Tim Saarinen. "Pure absorption gradient enhanced heteronuclear single quantum correlation spectroscopy with improved sensitivity." Journal of the American Chemical Society 114.26 (1992): 10663-10665.
Kennedy, David J., et al. "Central role for the cardiotonic steroid marinobufagenin in the pathogenesis of experimental uremic cardiomyopathy" Hypertension 47 3 (2006): 488-495.
Khan K, et al. Homozygous mutations in PXDN cause congenital cataract, corneal opacity, and developmental glaucoma. Am J Hum Genet. Sep. 9, 2011;89(3):464-73.
Khoshnoodi, Jamshid, et al. "Mechanism of chain selection in the assembly of collagen IV: a prominent role for the a2 chain." Journal of Biological Chemistry 281.9 (2006): 6058-6069.
Khoshnoodi, Jamshid, Vadim Pedchenko, and Billy G. Hudson. "Mammalian collagen IV." Microscopy research and technique 71.5 (2008): 357-370.
Kivirikko, Kari I., and Taina Pihlajaniemi. "Collagen hydroxylases and the protein disulfide isomerase subunit of prolyl 4-hydroxylases." Advances in enzymology and related areas of molecular biology 72 (1998): 325-398.
Kleinewietfeld M, Manzel A, Titze J, Kvakan H, Yosef N, Linker RA, Muller DN, Hafler DA. Sodium chloride drives autoimmune disease by the induction of pathogenic TH17 cells. Nature. Apr. 25, 2013;496(7446):518 22.
Kubicek-Sutherland, Jessica Z., et al. "Host-dependent induction of transient antibiotic resistance: a prelude to treatment failure." EBioMedicine 2.9 (2015): 1169-1178.
Kuo DS, Labelle-Dumais C, Gould DB. COL4A1 and COL4A2 mutations and disease: insights into pathogenic mechanisms and potential therapeutic targets. Hum Mol Genet. Oct. 15, 2012;21(R1):R97-110.
Lagerwerf, Fija M., et al. "Identification of oxidized methionine in peptides." Rapid Communications in Mass Spectrometry 10.15 (1996): 1905-1910.

(56) References Cited

OTHER PUBLICATIONS

Lambeth and Swank, Federation Proc., 38:830, 1979.
Lee TC, Yang JY, Wang HP, Tsai TJ, Yang Y. Peritoneal thickening is not inevitable in long-term peritoneal dialysis and is associated with peritoneal transport characteristics: a two-centre sonographic study. Nephrol Dial Transplant. Mar. 2008;23(3):1005-10.
Licklider, Lawrence J., et al. "Automation of nanoscale microcapillary liquid chromatography—tandem mass spectrometry with a vented column." Analytical chemistry 74.13 (2002): 3076-3083.
López B, González A, Ravassa S, Beaumont J, Moreno MU, San José G, Querejeta R, Díez J. Circulating Biomarkers of Myocardial Fibrosis: The Need for a Reappraisal. J Am Coll Cardiol. Jun. 9, 2015;65(22):2449-56.
Lourenço P, Araújo JP, Azevedo A, Ferreira A, Bettencourt P. The cyclic guanosine monophosphate/B-type natriuretic peptide ratio and mortality in advanced heart failure. Eur J Heart Fail. Feb. 2009;11(2):185-90.
Malara, Alessandro, et al. "Megakaryocytes contribute to the bone marrow-matrix environment by expressing fibronectin, type IV collagen, and laminin." Stem cells 32.4 (2014): 926-937.
Marcinkiewicz J, Walczewska M, Olszanecki R, Bobek M, Biedron R, Dulak J, Józkowicz A, Kontny E, Maslinski W. Taurine haloamines and heme oxygenase-1 cooperate in the regulation of inflammation and attenuation of oxidative stress. Adv Exp Med Biol. 2009;643:439-50.
Masago K, et al. Association between brain natriuretic peptide and distant metastases in advanced non-small cell lung cancer patients. Oncol Lett. Mar. 2011;2(2):253-256.
Matias, Patricia, et al. "Peritoneal membrane thickness in incident peritoneal dialysis patients is associated with comorbidity, solute transport rate and ultrafiltration failure." Port J Nephrol Hypert 23.2 (2009): 161-166.
Matsue, Yuya, et al. "Carperitide is associated with increased in-hospital mortality in acute heart failure: a propensity score-matched analysis." Journal of cardiac failure 21.11 (2015): 859-864.
Maya, Lisandro, and Francisco J. Villarreal. "Diagnostic approaches for diabetic cardiomyopathy and myocardial fibrosis." Journal of molecular and cellular cardiology 48.3 (2010): 524-529.
McCall, A. Scott, et al. "Bromine is an essential trace element for assembly of collagen IV scaffolds in tissue development and architecture." Cell 157.6 (2014): 1380-1392.
Mertz, Walter. "The essential trace elements." Science 213.4514 (1981): 1332-1338.
Miura, Yoshinori, et al. "Trace elements in renal disease and hemodialysis." Nuclear Instruments and Methods in Physics Research Section B: Beam Interactions with Materials and Atoms 189.1-4 (2002): 443-449.
Moser, Markus, et al. "The tail of integrins, talin, and kindlins." Science 324.5929 (2009): 895-899.
Nambi V, et al. Common carotid artery intima-media thickness is as good as carotid intima-media thickness of all carotid artery segments in improving prediction of coronary heart disease risk in the Atherosclerosis Risk in Communities (ARIC) study. Eur Heart J. Jan. 2012;33(2):183-90.
Nathan, Mewton, et al. "Assessment of myocardial fibrosis with cardiac magnetic resonance." Journal of the American college of cardiology 57.8 (2011): 891-903.
National Chronic Kidney Disease Fact Sheet, 2017 www.cdc.gov/diabetes/pubs/pdf/kidney_factsheet.pdf. Accessed Jul. 3, 2020.
National Institute of Health and Care Excellence. "NICE Guideline CG182 Chronic Kidney Disease in adults: assessment and management." (2014).
Naughton, Cynthia A. "Drug-induced nephrotoxicity." American family physician 78.6 (2008): 743-750.
Nelson, Robert E., et al. "Peroxidasin: a novel enzyme-matrix protein of Drosophila development." The EMBO journal 13.15 (1994): 3438-3447.
Ochi, Akinobu, et al. "Trace elements in the hair of hemodialysis patients." Biological trace element research 143.2 (2011): 825-834.
Ogawa H, Qiu Y, Philo JS, Arakawa T, Ogata CM, Misono KS. Reversibly bound chloride in the atrial natriuretic peptide receptor hormone-binding domain: possible allosteric regulation and a conserved structural motif for the chloride-binding site. Protein Sci. Mar. 2010;19(3):544-57.
Palmer III, Arthur G., et al. "Sensitivity improvement in proton-detected two-dimensional heteronuclear correlation NMR spectroscopy." Journal of Magnetic Resonance (1969) 93.1 (1991): 151-170.
Parkin, J. Des, et al. "Mapping structural landmarks, ligand binding sites, and missense mutations to the collagen IV heterotrimers predicts major functional domains, novel interactions, and variation in phenotypes in inherited diseases affecting basement membranes." Human mutation 32.2 (2011): 127-143.
Pastor-Pareja, José Carlos, and Tian Xu. "Shaping cells and organs in Drosophila by opposing roles of fat body-secreted Collagen IV and perlecan." Developmental cell 21.2 (2011): 245-256.
Pavelka, S., A. Babicky, and M. Vobecky. "Biological half-life of bromide in the rat depends primarily on the magnitude of sodium intake." Physiological research 54.6 (2005): 639.
Pitt, Bertram, and Faiez Zannad. "The detection of myocardial fibrosis: an opportunity to reduce cardiovascular risk in patients with diabetes mellitus?." (2012): 9-11.
Podell, Michael, and William R. Fenner. "Bromide therapy in refractory canine idiopathic epilepsy." Journal of Veterinary Internal Medicine 7.5 (1993): 318-327.
Pöschl, Ernst, et al. "Collagen IV is essential for basement membrane stability but dispensable for initiation of its assembly during early development." Development 131.7 (2004): 1619-1628.
Reid, Gavin E., et al. "Statistical and mechanistic approaches to understanding the gas-phase fragmentation behavior of methionine sulfoxide containing peptides." Journal of proteome research 3.4 (2004): 751-759.
Reule, Scott, and Paul E. Drawz. "Heart rate and blood pressure: any possible implications for management of nypertension?." Current hypertension reports 14.6 (2012): 478-484.
Sackner-Bernstein, Jonathan D., et al. "Short-term risk of death after treatment with nesiritide for decompensated heart failure: a pooled analysis of randomized controlled trials." Jama 293.15 (2005): 1900-1905.
Sackner-Bernstein, Jonathan D., Hal A. Skopicki, and Keith D. Aaronson. "Risk of worsening renal function with nesiritide in patients with acutely decompensated heart failure." Circulation 111.12 (2005): 1487-1491.
Sakaguchi, Yusuke, et al. "Hypomagnesemia is a significant predictor of cardiovascular and non-cardiovascular mortality in patients undergoing hemodialysis." Kidney international 85.1 (2014): 174-181.
Sakaguchi, Yusuke, et al. "Magnesium modifies the cardiovascular mortality risk associated with hyperphosphatemia in patients undergoing hemodialysis: a cohort study." PLoS One 9.12 (2014): e116273.
Saraswat, P., et al. "DNA as therapeutics; an update." Indian journal of pharmaceutical sciences 71.5 (2009): 488.
Sawala, Annick, Catherine Sutcliffe, and Hilary L. Ashe. "Multistep molecular mechanism for bone morphogenetic protein extracellular transport in the Drosophila embryo." Proceedings of the National Academy of Sciences 109.28 (2012): 11222-11227.
Schleucher, Jürgen, et al. "A general enhancement scheme in heteronuclear multidimensional NMR employing pulsed field gradients." Journal of biomolecular NMR 4.2 (1994): 301-306.
Schlueter N, et al. Metabolic actions of natriuretic peptides and therapeutic potential in the metabolic syndrome. Pharmacol Ther Oct. 2014;144(1):12-27.
Senthilmohan R, Kettle AJ. Bromination and chlorination reactions of myeloperoxidase at physiological concentrations of bromide and chloride. Arch Biochem Biophys. Jan. 15, 2006;445(2):235-44.
Serafino A, Pierimarchi P. Atrial natriuretic peptide: a magic bullet for cancer therapy targeting Wnt signaling and cellular pH regulators. Curr Med Chem. 2014;21(21):2401-9.
Shroff, Rukshana C., et al. "Clinical Perspective." Circulation 118.17 (2008): 1748-1757.
Siebold B, Deutzmann R, Kühn K. The arrangement of intra- and intermolecular disulfide bonds in the carboxyterminal, non-

(56) References Cited

OTHER PUBLICATIONS collagenous aggregation and cross-linking domain of basement-membrane type IV collagen. Eur J Biochem. Oct. 1, 1988;176(3):617-24.

Song, Jeremy J., and Harald C. Ott. "Organ engineering based on decellularized matrix scaffolds." Trends in molecular medicine 17.8 (2011): 424-432.

Speight, T. M., and G. S. Avery. "Pancuronium bromide: A review of its pharmacological properties and clinical application." Drugs 4.3 (1972): 163-226.

Springer, Jeremy, et al. "The natriuretic peptides BNP and CNP increase heart rate and electrical conduction by stimulating ionic currents in the sinoatrial node and atrial myocardium following activation of guanylyl cyclase-linked natriuretic peptide receptors." Journal of molecular and cellular cardiology 52.5 (2012): 1122-1134.

* cited by examiner

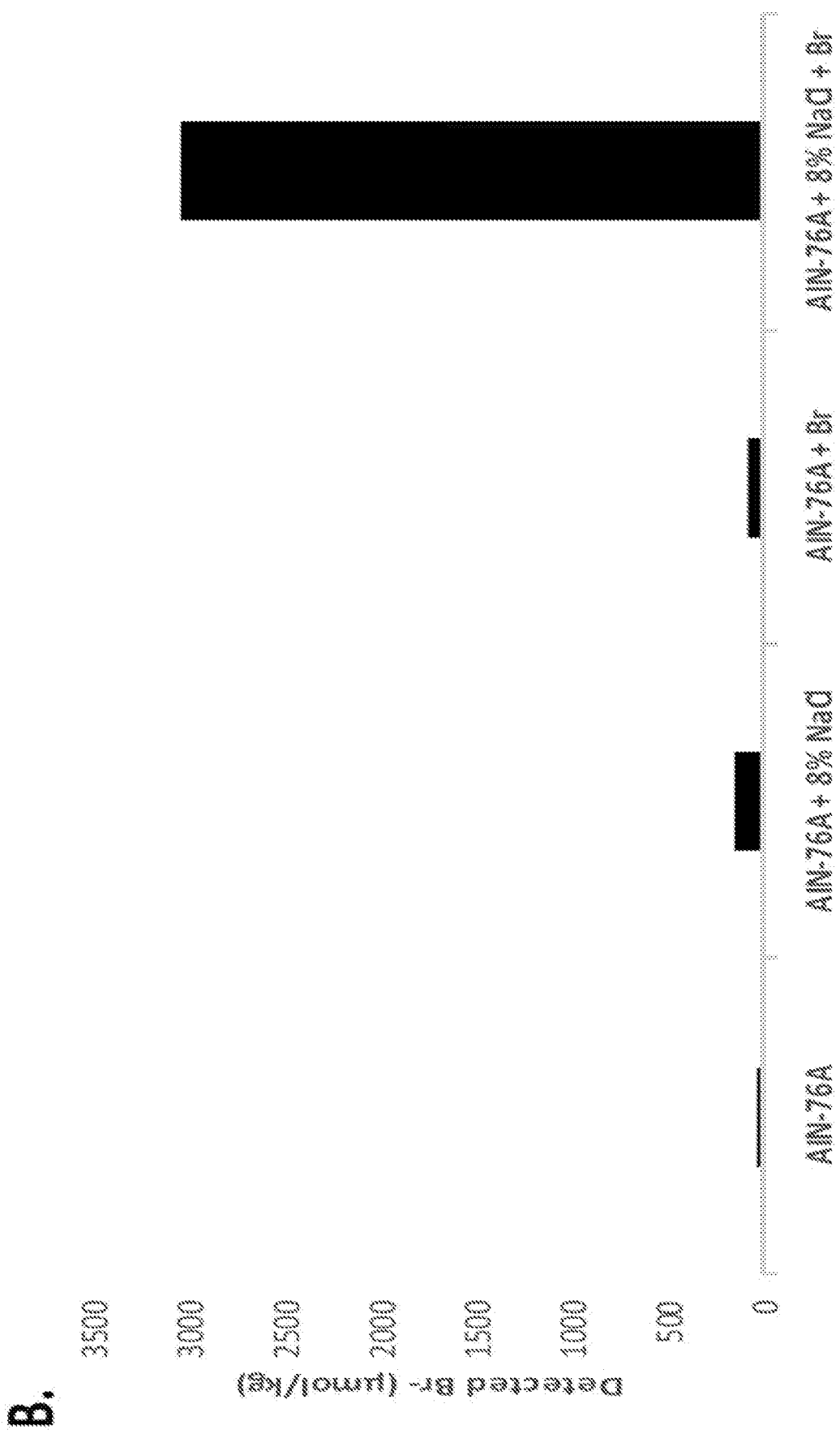
FIGURE 2 - CONT.

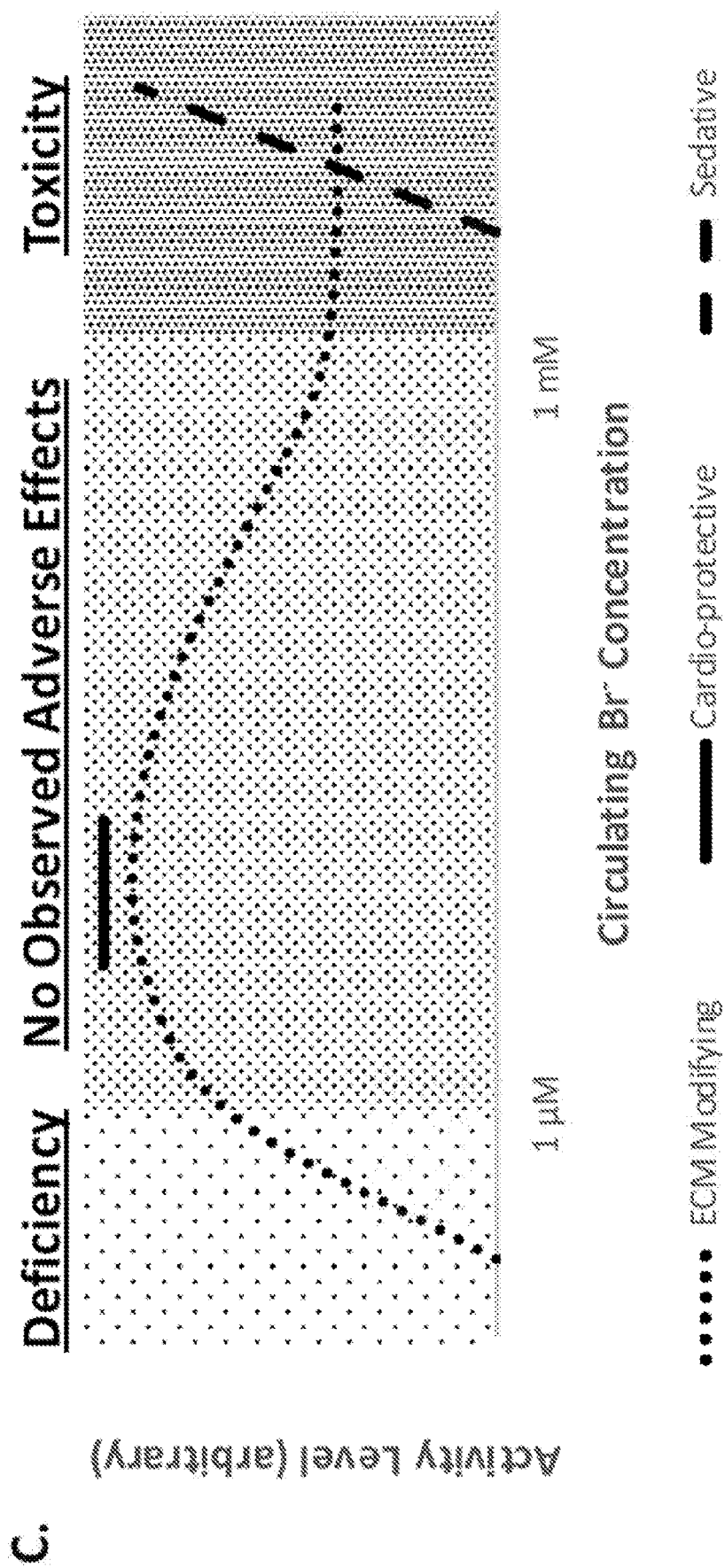
FIGURE 2 - CONT.

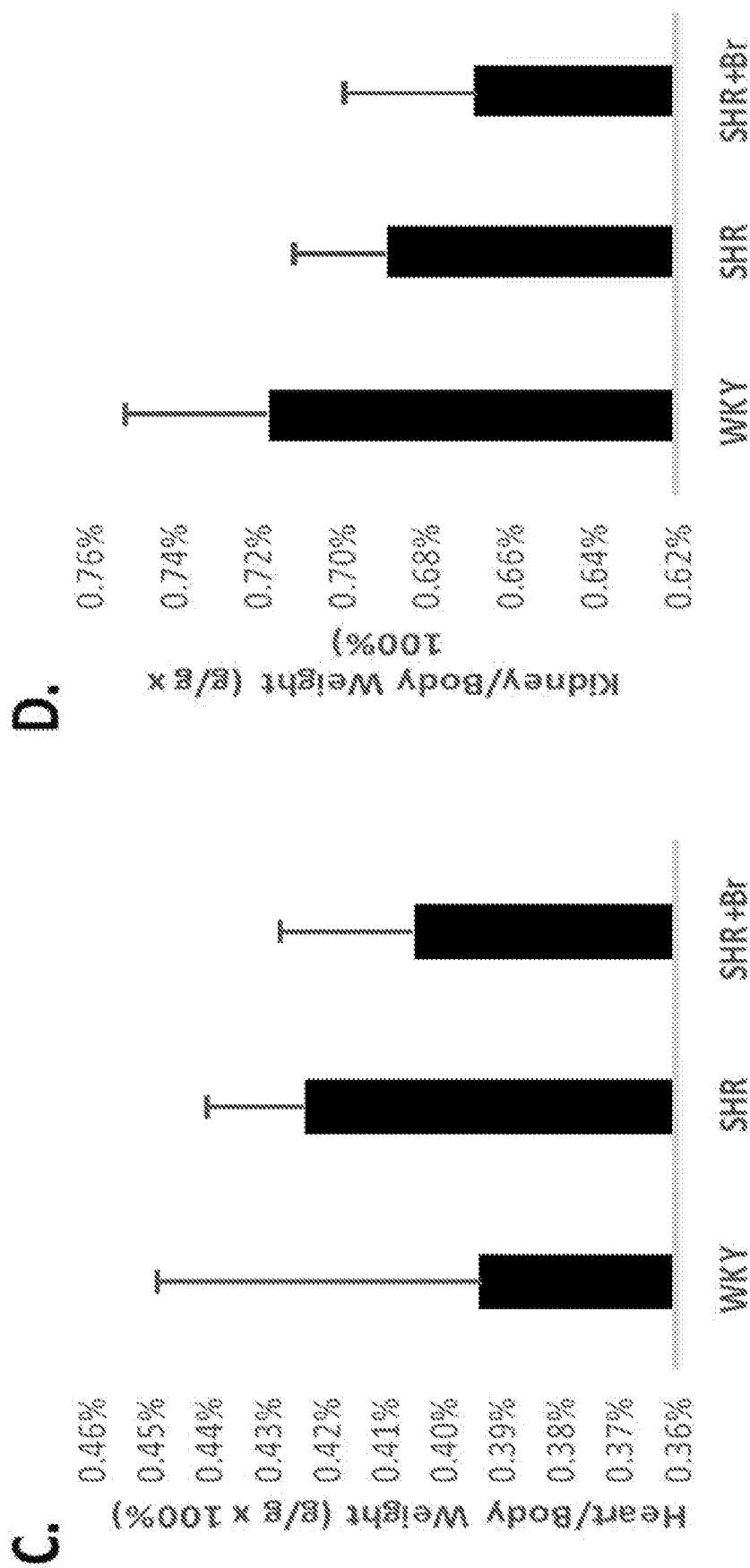
FIGURE 3 - CONT.

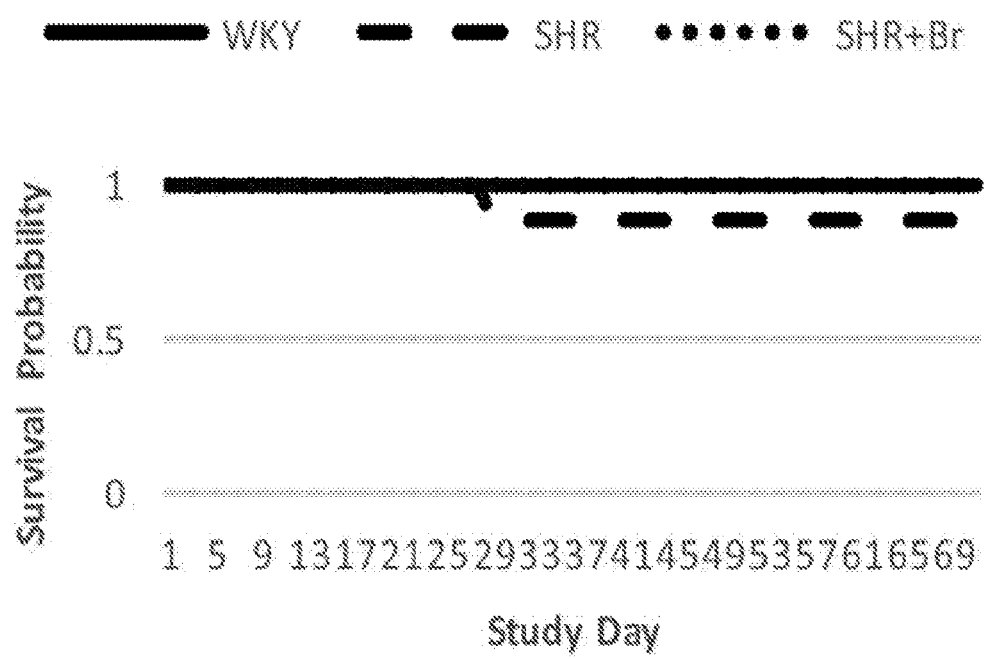
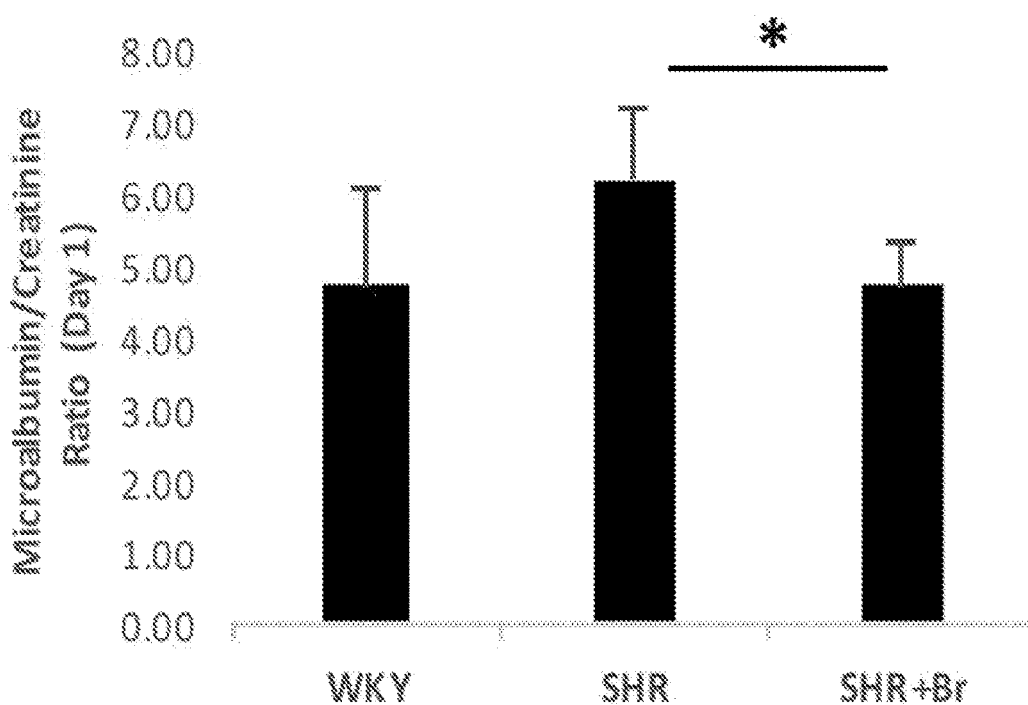
FIGURE 3 - CONT.

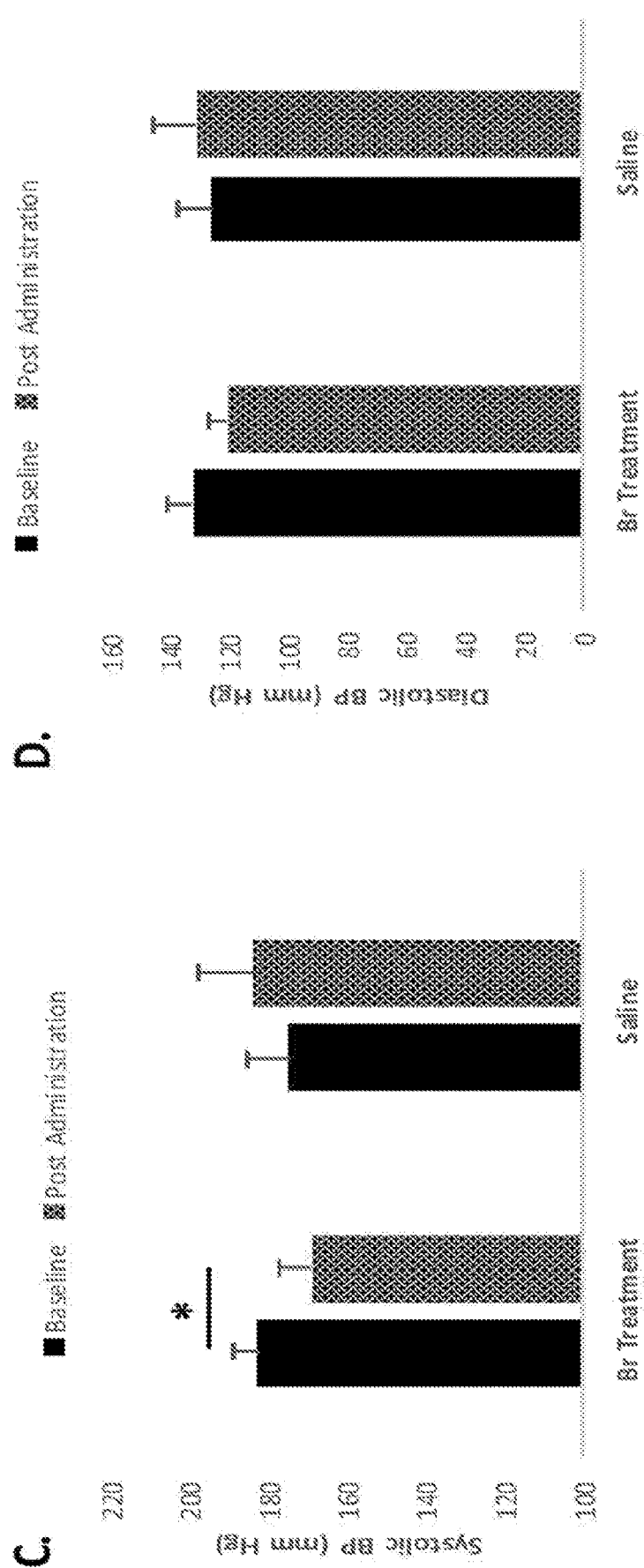
FIGURE 5 - CONT.

COMPOSITIONS AND METHODS FOR TREATING DISEASE

This application is a National Stage Application of PCT/US2017/046415 filed on Aug. 11, 2017, which claims priority from U.S. Provisional Application No. 62/373,656 filed on Aug. 11, 2016, U.S. Provisional Application No. 62/402,291 filed on Sep. 30, 2016, U.S. Provisional Application No. 62/402,309 filed on Sep. 30, 2016, and U.S. Provisional Application No. 62/424,057, filed on Nov. 18, 2016, the entire contents of each which are incorporated herein by reference.

SEQUENCE LISTING

The instant application contains a Sequence Listing which has been submitted electronically in ASCII format and is hereby incorporated by reference in its entirety. Said ASCII copy, created on Apr. 21, 2022, is named 2933438-006US2_SL.txt and is 1,239 bytes in size.

FIELD OF THE INVENTION

The invention concerns compositions and methods for use in the field of medicine. Specifically, the invention provides pharmaceutical compositions and methods for their use in a subject.

BACKGROUND OF THE INVENTION

Cardiovascular disease is a leading cause of mortality in the United States of America. Kidney disease, including chronic kidney disease (CKD) and end-stage renal disease (ESRD), are increasingly prevalent and severely damage the quality of life for patients. Importantly, many forms of cardiovascular disease and kidney disease are chronic diseases that require long-term management. There are acute forms of these diseases as well, such as but not limited to acute kidney injury and acute heart failure. The financial burden imposed by these diseases are enormous. In the United States, 2013 Medicare expenditures for patients with either CKD or ESRD exceeded $80 billion (2015 USRDS Annual Report). The prevalence of these diseases is also quite large. It has been estimated that over 100 million individuals in the United States have some form of cardiovascular disease and/or kidney disease. In summary, there is a significant need for medications that effectively treat cardiovascular disease and/or kidney disease.

SUMMARY OF THE INVENTION

There is a significant need for medications that effectively treat disease, such as cardiovascular disease, cancer, diabetes, metabolic syndrome and/or kidney disease. Embodiments of the invention comprise sterile injectable compositions and methods for treating disease and/or ameliorating symptoms of a disease, such as cardiovascular disease, metabolic syndrome, diabetes, obesity, cancer, and/or kidney disease in a subject. In some embodiments, the invention comprises an injectable drug comprising $Br^-$. In some embodiments, the invention comprises an injectable drug comprising $Br^-$ and less than about 0.1% sodium chloride. Some embodiments comprise sterile injectable drug comprising $Br^-$ and less than about 0.1% sodium chloride. In embodiments, the invention comprises between about 1-50 mg bromide ions ($Br^-$). In embodiments, the invention comprises an amount between about 1-250 mg of bromide ions ($Br^-$) and less than about 0.1% sodium chloride. In embodiments, the invention comprises low doses of $Br^-$ or Br-comprising compositions. In embodiments, the invention comprises compositions comprising only an amount of $Br^-$ sufficient to raise the circulating levels of $Br^-$ above about 20 μM, and said compositions are administered to the subject. In other embodiments, the invention comprises compositions comprising an amount of $Br^-$ sufficient to raise the circulating levels of $Br^-$ to an amount between about 20 μM and 1 mM. Embodiments of the invention can use potassium bromide, sodium bromide, or magnesium bromide as a source of bromide. Embodiments of the invention can use a source of bromide that is of pharmaceutical grade or United States Pharmacopeia (USP) quality.

Embodiments of the invention comprise an orally administered pharmaceutical composition. comprising an amount between about 1 mg and about 250 mg of $Br^-$. In embodiments, the invention comprises low doses of Br— or Br-comprising compositions, such as an amount between about 1 mg and about 25 mg $Br^-$. In embodiments, the invention comprises compositions comprising only an amount of Br— sufficient to raise the circulating levels of Br— above about 20 μM, and said compositions are administered to the subject. In other embodiments, the invention comprises compositions comprising an amount of Br— sufficient to raise the circulating levels of Br— to an amount between about 20 μM and about 1 mM. Embodiments of the invention can use potassium bromide, sodium bromide, or magnesium bromide as a source of bromide. Embodiments of the invention can use a source of bromide that is of pharmaceutical grade or United States Pharmacopeia (USP) quality.

Embodiments of the invention are administered to a subject with cardiovascular disease, kidney disease, diabetes, metabolic syndrome, cancer, or is obese. Embodiments of the invention comprise a pharmaceutical composition for treating or preventing cardiovascular disease in a subject, the composition comprising an amount between about 1 mg and about 250 mg of $Br^-$.

In some embodiments, the invention comprises about 1 mg, 2 mg, 3 mg, 4 mg, 5 mg, 6 mg, 7 mg, 8 mg, 9 mg, 10 mg, 11 mg, 12 mg, 13 mg, 14 mg, 15 mg, 16 mg, 17 mg, 18 mg, 19 mg, 20 mg, 21 mg, 22 mg, 23 mg, 24 mg, 25 mg, 26 mg, 27 mg, 28 mg, 29 mg, 30 mg, 31 mg, 32 mg, 33 mg, 34 mg, 35 mg, 36 mg, 37 mg, 38 mg, 39 mg, 40 mg, 41 mg, 42 mg, 43 mg, 44 mg, 45 mg, 46 mg, 47 mg, 48 mg, 49 mg, 50 mg, 51 mg, 52 mg, 53 mg, 54 mg, 55 mg, 56 mg, 57 mg, 58 mg, 59 mg, 60 mg, 61 mg, 62 mg, 63 mg, 64 mg, 65 mg, 66 mg, 67 mg, 68 mg, 69 mg, 70 mg, 71 mg, 72 mg, 73 mg, 74 mg, 75 mg, 76 mg, 77 mg, 78 mg, 79 mg, 80 mg, 81 mg, 82 mg, 83 mg, 84 mg, 85 mg, 86 mg, 87 mg, 88 mg, 89 mg, 90 mg, 91 mg, 92 mg, 93 mg, 94 mg, 95 mg, 96 mg, 97 mg, 98 mg, 99 mg, 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or about 250 mg of bromide ions ($Br^-$).

In some embodiments, the invention comprises about 0.1%, about 0.09%, about 0.08%, about 0.07%, about 0.06%, about 0.05%, about 0.04%, about 0.03%, about 0.02%, about 0.01%, about 0.009%, about 0.008%, about 0.007%, about 0.006%, about 0.005%, about 0.004%, about 0.003%, about 0.002%, about 0.001%, or nearly undetectable amounts of sodium chloride.

In some embodiments, the invention comprises a method of administering a therapeutically effective amount of a composition comprising $Br^-$ to a subject in need thereof. In embodiments, low doses of $Br^-$ or $Br^-$ comprising compositions are administered. In embodiments, only an amount of $Br^-$ or $Br^-$ comprising composition sufficient to raise the circulating levels of $Br^-$ above 20 µM is administered to the subject. In some embodiments, an amount of $Br^-$ or $Br^-$ comprising composition is administered in order to raise the circulating levels of $Br^-$ to between about 20 µM and about 1 mM in a subject. For example, the invention comprises a method of administering a therapeutically effective amount of a composition comprising $Br^-$ to a patient with cardiovascular disease and/or kidney disease. In embodiments, the therapeutically effective amount of $Br^-$ is administered as an injectable composition. Non-limiting examples of ongoing diseases and symptoms that can be treated by the invention include cancer, diabetes, obesity, metabolic syndrome, cardiovascular disease, vascular disease, kidney disease, chronic kidney disease, end stage renal disease, glomerular disease, tubular disease, kidney injury, acute kidney injury, sepsis-induced kidney injury, drug-induced kidney injury, hypovolemia-induced kidney injury, ischemic kidney injury, fibrosis, vascular disease, hypertension, salt-sensitive hypertension, heart attack, heart failure, cardiac remodeling, cardiac fibrosis, atherosclerosis, stroke, arterial stiffening, vascular wall thickening, thickening of the peritoneal membrane, dyslipidemia, blood clot, anemia, an acid-base imbalance, hypercholemia, infection, sepsis, thrombosis, coronary artery disease, ischemic heart disease, peripheral artery disease, or any combination thereof.

In other embodiments, the invention comprises a method of preventing or delaying the onset of a disease in a subject, the method comprising administering either a therapeutically effective or a nutritionally effective amount of a composition comprising $Br^-$ to a subject who is at risk of developing a disease. In embodiments, the disease is a form of cardiovascular disease, kidney disease, diabetes, obesity, and/or metabolic syndrome. Non-limiting examples of other diseases which can be prevented by embodiments of the invention include infection and sepsis. In some embodiments, the subject is healthy at the time of administration. In some embodiments, the subject is at risk of developing a disease as described herein, such as a cardiovascular disease and/or kidney disease. A risk of developing a diseases as described herein can include, for example, a family history of a disease, such as a cardiovascular disease and/or kidney disease, or a subject who has a history of such a disease as described herein. In some embodiments, the subject has a family history of a disease as described herein, such as a cardiovascular disease and/or kidney disease. In some embodiments, the subject has a disease as described herein, such as cardiovascular disease and is at risk of developing kidney disease. In other embodiments, the subject has kidney disease and is at risk of developing cardiovascular disease. In other embodiments, the subject is receiving dialysis treatments. In other embodiments, the subject is at risk of developing a kidney injury due to sepsis, exposure to a nephrotoxic drug, chronic kidney disease, or a surgical operation. In other embodiments, the subject has an infection or sepsis.

Embodiments of the invention can be administered to a subject at regular intervals. For example, embodiments of the invention may be administered daily, two times per week, three times per week, multiple times per week, weekly, monthly, quarterly, semi-annually, annually, or by another regulator interval.

Embodiments of the invention comprise biomarkers indicating the need for administration of compositions as described herein. For example, low serum $Br^-$ levels can serve as a biomarker indicating the need for administration of compositions as described herein. Low serum $Br^-$ level can be about 20 uM or lower. As another example, blood, serum, or plasma thiocyanate levels above about 10 µM can also indicate the need for administration of compositions as described herein. In embodiments, blood levels of natriuretic peptides, such as ANP and BNP can indicate the need for administration of Br— compositions as described herein, where BNP levels below about 50 pg/ml or above 100 pg/ml or where ANP levels above about 77 pg/ml or below about 22 pg/ml can indicate need for administration of an embodiment of the invention. In some embodiments, BNP levels below about 40 pg/ml, or below about 30 pg/ml, or even below about 20 pg/ml, or even still below about 10 pg/ml can indicate need for administration of an embodiment of the invention. In some embodiments, BNP levels above about 100 pg/ml, or above about 200 pg/ml, or above about 300 pg/ml, or above about 400 pg/ml, or above about 500 pg/ml, or above about 600 pg/ml, or above about 700 pg/ml, or above about 800 pg/ml, or above about 900 pg/ml, or above about 1000 pg/ml, or above about 1100 pg/ml, or above about 1200 pg/ml, or above about 1300 pg/ml, or above about 1400 pg/ml, or above about 1500 pg/ml, or above about 1600 pg/ml, or above about 1700 pg/ml, or above about 1800 pg/ml, or above about 1900 pg/ml, or above about 2000 pg/ml can indicate need for administration of an embodiment of the invention. In some embodiments, ANP levels below about 20 pg/ml, or below about 15 pg/ml, or below about 10 pg/ml, or even below about 5 pg/ml, or even below about 1 pg/ml, or even still undetectable amounts of ANP can indicate need for administration of an embodiment of the invention. In some embodiments, ANP levels above about 77 pg/ml, above about 80 pg/ml, above about 90 pg/ml, above about 100 pg/ml, above about 110 pg/ml, above about 120 pg/ml, above about 130 pg/ml, above about 140 pg/ml, above about 150 pg/ml, above about 160 pg/ml, above about 170 pg/ml, above about 180 pg/ml, above about 190 pg/ml, above about 200 pg/ml, above about 210 pg/ml, above about 220 pg/ml, above about 230 pg/ml, above about 240 pg/ml, above about 250 pg/ml, above about 260 pg/ml, above about 270 pg/ml, above about 280 above about 290 pg/ml, or even above about 300 can indicate need for administration of an embodiment of the invention.

Embodiments of the invention comprise bromine-containing compositions, such as those comprising a bromine and a vitamin or mineral. For example, compositions can comprise $Br^-$ and one or more of magnesium, vitamin $B_1$, vitamin $B_2$, vitamin $B_3$, vitamin $B_5$, vitamin $B_6$, vitamin $B_9$, vitamin $B_{12}$, vitamin C, vitamin E, selenium, zinc, iron, vitamin D. For example, compositions can comprise between about 1 mg to about 50 mg of Br⁻ with one or more of the following:
- about 50 mg to about 600 mg magnesium,
- about 1.2 mg to about 1.5 mg of vitamin $B_1$ (thiamine),
- about 1.3 mg to about 1.7 mg of vitamin $B_2$ (riboflavin),
- about 16 mg to about 20 mg of vitamin $B_3$ (niacin),
- about 10 mg of vitamin $B_5$ (pantothenic acid),
- about 1.7 mg to about 100 mg of vitamin $B_6$ (pyridoxine),
- about 0.4 mg to about 5 mg of vitamin $B_9$ (folic acid),
- about 2.4 µg to about 2 mg of vitamin $B_{12}$ (cobalamin),
- about 60 mg to about 100 mg of vitamin C (ascorbic acid),
- about 30 I.U. of vitamin E (tocopherol),
- about 70 µg of selenium,
- about 11 mg to 25 mg of zinc,
- about 18 mg to 29 mg of iron and/or
- about 400 I.U. to 2000 I.U. of vitamin D.

Embodiments as described herein, such as the combination bromine-containing composition, can be formulated as a sterile injectable solution to be administered to a subject with a disease or at risk of developing a disease. For example, the disease can be cardiovascular disease, kidney disease, a disease as described herein, or a combination thereof.

Embodiments of the invention can comprise a pharmaceutical drug or be formulated to be administered to a subject with a medical device. The subject may be suffering from, or at risk of developing, a disease as described herein, such as cardiovascular disease, kidney disease, cancer, diabetes, obesity, metabolic syndrome, or a combination thereof. Non-limiting examples of drugs that can be combined with compositions as descried herein include blood pressure controlling agents, angiotensin-converting enzyme inhibitors, angiotensin receptor blockers, beta blocking agents, alpha blocking agents, antiarrhythmic agents, blood thinners, alpha agonists, sodium channel blocking agents, calcium channel blocking agents, antiplatelet agent, antihyperlipidemic agents, statin therapies, nonsteroidal anti-inflammatory drugs, loop diuretics, thiazide diuretics, potassium-sparing diuretics, vasodilators, renin inhibitors, dopamine, dopamine receptor agonists, thrombolytic agents, erythropoietin, erythropoietic stimulating agents, vitamins, vitamin analogues, drugs used in the management of ESRD, anti-infective agents, antibiotics, and antifungals. Non-limiting examples of medical devices that can administer to a subject compositions as described herein comprise a collagen-based wound healing device, a bandage, a plug, a patch, a stent, a tube, a dialysis machine, a port, a graft, a fistula, an intravascular balloon, a catheter, a bandage, or a powder.

Embodiments of the invention can be formulated for and distributed in many various types of packaging. Non-limiting examples include pre-filled syringes, vials, bottles, aerosol cans, or packets. The invention can be administered to a subject via a dropper, a syringe, a pre-filled syringe, a needle, a tube, a bag, a can, an aerosol can, a capsule, a vial, or a packet. Packaged forms of the invention are amenable to either room temperature storage or cold storage.

In some embodiments, compositions as described herein are packaged in a format that allows the invention to be conveniently administered to a patient through a dialysis treatment. For example, the packaging may contain a connector that allows the invention to be administered through an access port, fistula, graft, or catheter in a dialysis patient. As another example, the packaging may contain a connector that allows the invention to be administered through dialysis tubing, bag, machine, or container. These various packaging formats are within the scope of the invention, being used to administer compositions comprising a therapeutically effective amount of Br⁻ to a patient.

Some embodiments can be administered to a subject who receives nutrition under the supervision of a doctor. Some embodiments can be administered to a subject who is receiving parenteral nutrition. Some embodiments can administer via injection a nutritionally effective amount of Br⁻ to a subject in need thereof. In some embodiments, the invention is combined with other fluids and the combination is administered to a subject in need of parenteral nutrition.

Embodiments of the invention can be administered to a mammalian subject. In some embodiments, the subject is a human. In other embodiments, the subject is a dog, cat, horse, cow, goat, sheep, or pig.

Embodiments of the invention can be injected into the bloodstream, skin, tissue, peritoneal cavity, orbital socket, heart, muscle, bone marrow, epidural space, spinal theca, joint, genitals, or any other organ of a subject. Other embodiments can be injected through a needle and syringe to a subject, with non-limiting examples of the injection method including intramuscular, intradermal, subcutaneous, intravenous, intraosseous, intraperitoneal, intracardiac, intrathecal, epidural, intraarticular, intracavernous, and intravitreal. Other embodiments are administered to a subject through a tube, such as but not limited to a medical tubing, central line, intravenous (IV) line, catheter, or dialysis tubing. Some embodiments are administered to a subject through extracorporeal administration. A non-limiting example of an extracorporeal administration include administration of an embodiment to the bloodstream a subject undergoing dialysis where the embodiment is injected into the bloodstream either before or after the blood is passed through a dialysis filter or cartridge, and the administration occurs outside the subject's body. Some embodiments of the invention can be administered to a subject via a dropper, a syringe, a needle, a tube, a bag, a can, an aerosol can, a capsule, a vial, or a packet. Some embodiments can be stored in a syringe, vial, bag, bottle, tube, can, packet, or dialysis delivery system.

Some embodiments of the invention can be isotonic. Other embodiments can be hypotonic. Still other embodiments can be hypertonic. Tonicity of the embodiment can be adjusted with an osmotic agent other than sodium chloride, with non-limiting examples that include dextrose, lactose, and sodium bicarbonate.

In some embodiments, the invention comprises an injectable pharmaceutical composition for treating, preventing, or ameliorating a symptom of cardiovascular disease, kidney disease, diabetes, obesity, cancer, metabolic syndrome, or a combination thereof in a subject, the composition comprising an amount between about 1 mg and about 250 mg of bromide ions (Br⁻), such as between about 1 mg and about 50 mg of bromide ions, and less than about 0.1% sodium chloride. In some embodiments of said composition the bromide source comprises sodium bromide, potassium bromide, magnesium bromide, or a combination thereof. In some embodiments, said composition is stored in a syringe, vial, bag, bottle, tube, can, packet, or dialysis delivery system. In some embodiments, said composition is stored in a prefilled syringe. In some embodiments, the symptom is chronic kidney disease; end stage renal disease; glomerular disease; tubular disease; kidney injury; acute kidney injury; sepsis-induced kidney injury; drug-induced kidney injury; hypovolemia-induced kidney injury; ischemic kidney injury; type 1 diabetes; type 2 diabetes; type 3 diabetes; gestational diabetes; juvenile diabetes; latent autoimmune diabetes of adulthood; maturity onset diabetes of the young;

insulin resistance; hyperglycemia; steroid-induced diabetes; brittle diabetes; diabetes insipidus; diabetes mellitus; solid tumor; metastatic tumor; epithelial cancer; circulating cancer cells; eye cancer; kidney cancer; childhood cancer; brain cancer; spinal cord tumor; liver cancer; bone cancer; colorectal cancer; stomach cancer; small intestine cancer; prostate cancer; breast cancer; skin cancer; basal cell cancer; squamous cell skin cancer; melanoma; multiple myeloma; lung cancer; lung tumor; small cell lung cancer; non-small cell lung cancer; blood cancer; leukemia; lymphoma; Hodgkin's lymphoma; non-Hodgkin's lymphoma; bladder cancer; oral cancer; oropharyngeal cancer; pancreatic cancer; thyroid cancer; thymus cancer; uterine cancer; uterine sarcoma; cervical cancer; ovarian cancer; testicular cancer; Wilms tumor; acute lymphocytic leukemia, chronic lymphocyte leukemia; acute myeloid leukemia; chronic myeloid leukemia; chronic myelomonocytic leukemia; adrenal cancer; anal cancer; bile duct cancer; endometrial cancer; esophagus cancer; a Ewing tumor; gallbladder cancer; gastrointestinal tumor; Kaposi sarcoma; laryngeal cancer; hypopharyngeal cancer; malignant mesothelioma; Merkel cell skin cancer; myelodysplastic syndrome; cancer of the nasal cavity; paranasal sinus cancer; nasopharyngeal cancer; neuroblastoma; osteosarcoma; penile cancer; pituitary tumor; retinoblastoma; rhabdomyosarcoma; salivary gland cancer; soft tissue sarcoma; vaginal cancer; vulvar cancer vascular disease; hypertension; salt-sensitive hypertension; heart attack; heart failure; cardiac remodeling; cardiac fibrosis; atherosclerosis; stroke; arterial stiffening; vascular wall thickening; thickening of the peritoneal membrane; blood clot; an acid-base imbalance; hypercholemia; infection; sepsis; thrombosis; coronary artery disease; ischemic heart disease; peripheral artery disease; syndrome x; displaying at least three of the following metabolic risk factors: waist size greater than 40 inches if male subject or greater than 35 inches if female subject, blood tryglyceride levels of at least about 150 mg/dl or higher or currently using a cholesterol medication, blood high-density lipoprotein levels lower than about 40 mg/dl if male subject or lower than about 50 mg/dl if female subject or currently using a cholesterol medication, blood pressure above about 135/85 mm Hg (systolic over diastolic) or using a high blood pressure medication, and fasting blood glucose levels of about 100 mg/dl or higher; or any combination thereof.

In some embodiments, the subject has end stage renal disease or cancer. In some embodiments, the subject is a mammal. In other embodiments, the subject is a human, dog, cat, horse, cow, goat, sheep, or pig.

In some embodiments, the invention comprises an injectable pharmaceutical composition that comprises bromide ions (Br$^-$) and less than about 0.1% sodium chloride, further comprising magnesium, vitamin B1 (thiamine), vitamin B2 (riboflavin), vitamin B3 (niacin), vitamin B5 (pantothenic acid), vitamin B6 (pyridoxine), vitamin B7 (biotin), vitamin B9 (folic acid), vitamin B12 (cobalamin), vitamin C (ascorbic acid), vitamin E (tocopherol), selenium, zinc, iron, vitamin D, or a combination thereof. In some embodiments, the invention is combined with a pharmaceutical drug and administered to a subject. In some embodiments, the drug comprises a blood pressure controlling agent, angiotensin-converting enzyme inhibitor, angiotensin receptor blocker, beta blocking agent, alpha blocking agent, antiarrhythmic agent, blood thinner, alpha agonist, sodium channel blocking agent, calcium channel blocking agent, antiplatelet agent, antihyperlipidemic agent, statin therapy, nonsteroidal anti-inflammatory drug, loop diuretic, thiazide diuretic, potassium-sparing diuretic, vasodilator, renin inhibitor, dopamine, dopamine receptor agonist, thrombolytic agent, erythropoietin, erythropoietic stimulating agent, vitamin, vitamin analogue, drug used in the management of ESRD, anti-infective agent, antibiotic, antifungal, cancer chemotherapy, cancer radiotherapy or combination thereof. Non-limiting examples of drugs comprise captopril, enalapril, fosinopil, lisinopril, perindopril, quinapril, trandolapril, benazepril, ramipril, azilsartan, candesartan, telmisartan, fimasartan eprosartan, irbesartan, losartan, olmesartan, valsartan, doxazosin, phentolamine, indoramin, phenoxybenzamine, tolazoline, bucindolol, carvedilol, labetalol, tamsulosin, terazosin, prazosin, alfuzosin, timolol, betaxolol, propranolol, atenolol, nadolol, nebivolol, oxprenolol, pindolol, propranolol, metoprolol, sodium nitroprusside, hydralazine, adenosine, sildenafil, vardenafil, tadalafil, prostacyclin, nitric oxide, amiodarone, mexiletine, disopryamide, propafenone, diltiazem, dihydropyridines, amlodipine, cilnidipine, felodipine, isradipine, nimodipine, lercanidipine, levamlodipine, nicardipine, nitrendipine, nifedipine, verapamil, spironolactone, bumetanide, ethacrynic acid, epitizide, metolazone, amiloride, triamterene, torsemide, furosemide, indapamide, triamterene, hydrochlorothiazide, chlorothiazide, bendroflumethiazide, chlorthalidone, celecoxib, meloxicam, ibuprofen, naproxen, diclofenac, aspirin, dipyridamole, clopidogrel, cilostazol, ticlopidine, lovastatin, niacin, simvastatin, ezetimibe, warfarin, carperitide (recombinant ANP), nesiritide (recombinant BNP), tinzaparin, enoxaparin, heparin, atorvastatin, fluvastatin, pravastatin, rosuvastatin, aliskiren, alteplase, anistreplase, reteplase, tenecteplase, streptokinase, tissue plasminogen activator, urokinase, recombinant human erythropoietin, epoetin alpha, epoetin beta, darbepoetin alpha, methoxy polyethylene glycol-epoetin beta, Epo, Procrit®, Epogen®, Aranesp, Mircera, vitamin D, rocaltrol, calcitriol, Zemplar®, hectorol, doxercalciferol, carnitor, levocarntine, lepiridun, reteplase, alteplase, peginesatide, iron, sodium ferric gluconate, vitamin B12, Darbepoetin, midazolam hydrochloride, diazepam, calcium gluconate, calcitonin, deferoxamine, doxercalciferol, ibandronate, pamidronate, paricalcitol, methotrexate, paclitaxel, brentuximab, brentuximab vedotin, anthracyclines, doxorubicin, doxorubicin lipid complex, fluorouracil, fluorouracil 5-FU, everolimus, pemetrexed, melphalan, pamidronate, anastrozole, exemestane, nelarabine, ofatumumab, bevacizumab, belinostat, tositumomab, carmustine, bleomycin, blinatumomab, bosutinib, busulfan, alemtuzumab, irinotecan, vandetanib, bicalutamide, lomustine, daunorubicin, daunorubicin lipid complex, clofarabine, cabozantinib, dactinomycin, cobimetinib, ramucirumab, cytarabine, cytarabine lipid complex, cytoxan, cyclophosphamide, decitabine, dexamethasone, docetaxel, hydroxyurea, decarbazine, leuprolide, epirubicin, oxaliplatin, asparaginase, asparaginase *Erwinia chrysanthemi*, estramustine, cetuximab, vismodegib, amifostine, etoposide, flutamide, toremifene, panobinostat, fulvestrant, letrozole, degarelix, fludarabine, pralatrexate, floxuridine, obinutuzumab, gemcitabine, afatinib, imatinib, imatinib mesylate, carmustine, eribulin, trastuzumab, altretamine, topotecan, palbociclib, ponatinib, idarubicin, ifosfamide, ibrutinib, axitinib, interferon alpha-2a, peginterferon alpha-2a, gefitinib, romidepsin, ixabepilone, ruxolitinib, cabazitaxel, ado-trastuzumab emtansine, pembrolizumab, carfilzomib, lenvatinib, chlorambucil, sargramostim, cladribine, trifluridine, tipiracil, leuprolide, olaparid, mitotane, vincristine, vincristine lipid complex, procarbazine, megestrol, trametinib, mesna, strontium-89 chloride, mechlorethamine, mitomycin, mitoantrone, busulfan, gemtuzumab ozogamicin, vinorelbine, filgrastim, pegfilgrastim, sorafenib, nilutamide, pentostatin, tamoxifen, mitoxantrone, sonidegib, pegaspargase, denileukin diftitox, nivolumab, alitretinoin, carboplatin, pertuzumab, cisplatin, pomalidomide, prednisone, aldesleukin, mercaptopurine, zoledronic acid, lenalidomide, rituximab, octreotide, dasatinib, regorafenib, histrelin, sunitinib, siltuximab, omacetaxine, thioguanine, dabrafenib, erlotinib, bexarotene, decarbazine, docetaxel, temozolomide, thiotepa, thalidomide, bacillus calmette-guerin (BCG) vaccine, temsirolimus, bendamustine hydrochloride, triptorelin, arsenic trioxide, lapatinib, dinutuximab, valrubicin, panitumumab, vinblastine, bortezomib, tretinoin, azacitidine, pazopanib, teniposide, leucovorin, crizotinib, capecitabine, enzalutamide, ipilimumab, trabectedin, ziv-afibercept, streptozocin, vemurafenib, ibritumomab tiuxetan, goserelin, vorinostat, everolimus, idelalisib, ceritinib, abiraterone, liposomes, deoxyribonucleic acid agents, ribonucleic acid agents, penicillin, amoxicillin, cephalexin, erythromycin, clarithromycin, azithromycin, ciprofloxacin, levofloxacin, ofloxacin, sulfamethoxazole, trimethoprim, fosfomycin, nitrofurantoin, ceftriaxone, clavulanate, clindamycin, doxycycline, tetracycline, clotrimazole, econazole nitrate, miconazole, terbinafine, fluconazole, ketoconazole, and amphotericin. Non-limiting examples of chemotherapy and radiotherapy comprises methotrexate, paclitaxel, brentuximab, brentuximab vedotin, anthracyclines, doxorubicin, doxorubicin lipid complex, fluorouracil, fluorouracil 5-FU, everolimus, pemetrexed, melphalan, pamidronate, anastrozole, exemestane, nelarabine, ofatumumab, bevacizumab, belinostat, tositumomab, carmustine, bleomycin, blinatumomab, bosutinib, busulfan, alemtuzumab, irinotecan, vandetanib, bicalutamide, lomustine, daunorubicin, daunorubicin lipid complex, clofarabine, cabozantinib, dactinomycin, cobimetinib, ramucirumab, cytarabine, cytarabine lipid complex, cytoxan, cyclophosphamide, decitabine, dexamethasone, docetaxel, hydroxyurea, decarbazine, leuprolide, epirubicin, oxaliplatin, asparaginase, asparaginase *Erwinia chrysanthemi*, estramustine, cetuximab, vismodegib, amifostine, etoposide, flutamide, toremifene, panobinostat, fulvestrant, letrozole, degarelix, fludarabine, pralatrexate, floxuridine, obinutuzumab, gemcitabine, afatinib, imatinib, imatinib mesylate, carmustine, eribulin, trastuzumab, altretamine, topotecan, palbociclib, ponatinib, idarubicin, ifosfamide, ibrutinib, axitinib, interferon alpha-2a, peginterferon alpha-2a, gefitinib, romidepsin, ixabepilone, ruxolitinib, cabazitaxel, ado-trastuzumab emtansine, pembrolizumab, carfilzomib, lenvatinib, chlorambucil, sargramostim, cladribine, trifluridine, tipiracil, leuprolide, olaparid, mitotane, vincristine, vincristine lipid complex, procarbazine, megestrol, trametinib, mesna, strontium-89 chloride, mechlorethamine, mitomycin, mitoantrone, busulfan, gemtuzumab ozogamicin, vinorelbine, filgrastim, pegfilgrastim, sorafenib, nilutamide, pentostatin, tamoxifen, mitoxantrone, sonidegib, pegaspargase, denileukin diftitox, nivolumab, alitretinoin, carboplatin, pertuzumab, cisplatin, pomalidomide, prednisone, aldesleukin, mercaptopurine, zoledronic acid, lenalidomide, rituximab, octreotide, dasatinib, regorafenib, histrelin, sunitinib, siltuximab, omacetaxine, thioguanine, dabrafenib, erlotinib, bexarotene, decarbazine, docetaxel, temozolomide, thiotepa, thalidomide, bacillus calmette-guerin (BCG) vaccine, temsirolimus, bendamustine hydrochloride, triptorelin, arsenic trioxide, lapatinib, dinutuximab, valrubicin, panitumumab, vinblastine, bortezomib, tretinoin, azacitidine, pazopanib, teniposide, leucovorin, crizotinib, capecitabine, enzalutamide, ipilimumab, trabectedin, ziv-afibercept, streptozocin, vemurafenib, ibritumomab tiuxetan, goserelin, vorinostat, everolimus, idelalisib, ceritinib, abiraterone, liposomes, deoxyribonucleic acid agents, ribonucleic acid agents, x-rays, gamma rays, and charged particles.

Embodiments of the invention can be therapeutically administered to a subject with an endocrinopathy, such as diabetes or metabolic syndrome. Non-limiting examples of endocrinopathies comprise insulin resistance, metabolic syndrome, hyperglycemia, cancer-associated diabetes or diabetes mellitus. For example, cancer-associated diabetes can be secondary to pancreatic cancer. Embodiments of the invention can be therapeutically administered to an obese or overweight subject. For example, administering a composition to a subject afflicted with diabetes, metabolic syndrome, obesity, or a combination thereof can increase circulating ANP, BNP, or cGMP, such as increasing blood BNP to above 10 pg/ml or above 20 pg/ml or even above 30 pg/ml or event still above 40 pg/ml; promote ANP or BNP signaling; and/or reduce blood pressure, so as to prevent or treat diabetes, metabolic syndrome, or obesity in the subject. As another example, embodiments of the invention can prevent or treat cardiovascular disease in a subject who is overweight or obese, has diabetes, or has metabolic syndrome.

Embodiments of the invention can be administered to a subject by itself or in combination with another pharmaceutical drug or behavioral treatment, for example as part of treatment regimen. The other pharmaceutical drug can be administered at the same time as an embodiment as described herein, such as a Br— containing composition, or at separate times, e.g., at separate times that are within a specified interval, e.g., within 168, 144, 120, 96, 72, 48, 24, 12, 6, 2, 1 hour or 15 minutes of administration of the Br— containing compositions. In some embodiments, the other pharmaceutical drug is a drug used to treat an endocrinopathy, such as diabetes, metabolic syndrome, or obesity. Non-limiting examples of such pharmaceutical drugs include insulin, amylinomimetic agents, alpha-glucosidase inhibitors, biguanides, dopamine agonists, glucagon-like peptides, meglitinides, sodium glucose transporter 2 inhibitors, sulfonylureas, thiazolidinediones, and dipeptidyl peptidase-4 inhibitors. In some embodiments, the drug comprises regular insulin such as but not limited to Humulin or Novolin, insulin aspart such as but not limited to Novolog or FlexPen; insulin glulisine such as but not limited to Apidra; insulin lispro such as but not limited to Humalog; insulin isophane such as but not limited to Humulin N or Novolin N; insulin degludec such as but not limited to Tresiba; insulin detemir such as but not limited to Levemir; insulin glargine such as but not limited to Lantus; insulin glargine such as but not limited to Toujeo; a combination insulin drug such as but not limited to insulin aspart protamine-insulin aspart, insulin lispro protamine-insulin lispro, human isophane insulin-human insulin regular, insulin dedludec-insulin aspart, NovoLog Mix 70/30, Humalog Mix 75/25, Humalog Mix 50/50, Humalin 70/30, Novolin 70/30, or Ryzodeg; pramlintide such as but not limited to SymlinPen; acarbose such as but not limited to Precose; miglitol such as but not limited to Glyset; metformin such as but not limited to Glucophage, Metformin Hydrochloride ER, Glumetza, Riomet, or Fortamet; a metformin-containing drug such as but not limited to metformin-alogliptin, Kazano, metformin-canagliflozin, Invokamet, metformin-dapagliflozin, Xigduo XR, metformin-empagliflozin, Synjardy, metformin-glipizide, metformin-glyburide, Glucovance, metformin-linagliptin, Jentadueto, metformin-pioglitazone, Actoplus, Actoplus Met, Actoplus Met XR, metformin-repaglinide, PrandiMet, metformin-rosiglitazone, Avandamet, metformin-saxagliptin, Kombiglyze XR, metformin-sitagliptin, Janumet, or Janumet XR; bromocriptine such as but not limited to Parlodel;

alogliptin such as but not limited to Nesina; alogliptin-pioglitazone such as but not limited to Oseni; linagliptin such as but not limited to Tradjenta, linagliptin-empagliflozin such as but not limited to Glyzami; saxagliptin such as but not limited to Onglyza; sitagliptin such as but not limited to Januvia; sitagliptin and simvastatin such as but not limited to Juvisync; albiglutide such as but not limited to Tanzeum; dulaglutide such as but not limited to Trulicity; exenatide such as but not limited to Byetta; exenatide extended-release such as but not limited to Bydureon; liraglutide such as but not limited to Victoza; nateglinide such as but not limited to Starlix; repaglinide such as but not limited to Prandin; dapagliflozin such as but not limited to Farxiga; canaglifoxin such as but not limited to Invokana; empaglifozin such as but not limited to Jardiance; empagliflozin-linagliptin such as but not limited to Glyxambi; glimepiride such as but not limited to Amaryl; glimepiride-pioglitazone such as but not limited to Duetact; glimepiride-rosiglitazone such as but not limited to Avandaryl; gliclazide, glipizide such as but not limited to Glucotrol; glyburide such as but not limited to DiaBeta, Glynase, or Micronase; chlorpropamide such as but not limited to Diabinese; tolazamide such as but not limited to Tolinase; tolbutamide such as but not limited to Orinase or TolTab; rosiglitazone such as but not limited to Avandia; or pioglitazone such as but not limited to Actos. In some embodiments, the treatment regimen includes administration of one or more pharmaceutical drugs, each administered separately to a subject; behavioral modification such as dietary changes and increased daily exercise; or surgery such as bariatric surgery.

Some embodiments of the invention comprise a method of preventing a disease in a subject, such as preventing cardiovascular disease or kidney disease in a subject, the method comprising measuring the $Br^-$ concentration in the blood or serum of a subject and/or measuring natriuretic peptides in the blood or serum of a subject; determining the subject to be at risk of developing cardiovascular disease or kidney disease if the $Br^-$ serum concentration is below about 20 μM, the blood ANP is below about 22 pg/ml or above about 77 pg/ml, and/or the blood BNP is below about 50 pg/ml or above about 100 pg/ml; and administering a therapeutically effective amount of an injectable pharmaceutical composition that comprises bromide ions ($Br^-$) and less than about 0.1% sodium chloride to the subject to prevent cardiovascular disease or kidney disease.

In some embodiments, the invention comprises a method for the treatment of disease in a subject, said method comprising administering to a subject in need of such treatment a therapeutically effective amount of an injectable pharmaceutical composition that comprises bromide ions ($Br^-$) and less than about 0.1% sodium chloride in an amount no greater than that required to result in a body fluid concentration no greater than 500 μM. In some embodiments, the disease comprises a cardiovascular disease, a kidney disease, diabetes, obesity, cancer, metabolic syndrome, or a combination thereof. In some embodiments, the $Br^-$ is administered at a dose no greater than 250 mg.

Some embodiments of the invention comprise an injectable pharmaceutical composition comprising a $Br^-$ dose no greater than that required to result in a body fluid concentration no greater than 500 μM in a subject. In some embodiments, the subject has or is at risk of developing a symptom of cardiovascular disease, kidney disease, diabetes, obesity, metabolic syndrome, cancer, or a combination thereof. In some embodiments, the symptom is chronic kidney disease, end stage renal disease, glomerular disease, tubular disease, kidney injury, acute kidney injury, sepsis-induced kidney injury, drug-induced kidney injury, hypovolemia-induced kidney injury, ischemic kidney injury, fibrosis, vascular disease, hypertension, salt-sensitive hypertension, heart attack, heart failure, cardiac remodeling, cardiac fibrosis, atherosclerosis, stroke, arterial stiffening, vascular wall thickening, thickening of the peritoneal membrane, dyslipidemia, blood clot, anemia, an acid-base imbalance, hypercholemia, infection, sepsis, thrombosis, coronary artery disease, ischemic heart disease, peripheral artery disease, or any combination thereof. In some embodiments, the composition comprises $Br^-$ and a pharmaceutically acceptable carrier or salt thereof.

The inventors have discovered and developed an invention that comprises compositions and methods for treating disease, such as cardiovascular disease, kidney disease, an endocrinopathy (such as diabetes, obesity, metabolic syndrome), or cancer. Embodiments of the invention are designed to enable patients with one or more of these chronic diseases to better manage their health, to reduce the occurrence of acute manifestations of one or more of these diseases, to improve the quality of life for patients, and to reduce the financial burden imposed by these diseases.

Embodiments of the invention provide compositions and methods for preventing, treating and detecting cardiovascular disease or kidney disease in a subject. The subject can include humans, cats, dogs, or any other mammalian animal.

An embodiment of the invention provides for compositions and methods of treating cardiovascular disease or kidney disease in a subject, such as an animal or human. Embodiments also provide for compositions and methods of treating diseases of the circulatory system. Some embodiments provide for effectively administering $Br^-$ ions to a subject. In some embodiments, a low dose of $Br^-$, less than 1 mg $Br^-$, or between 1 and 250 mg of $Br^-$ ions can be administered to a subject such as a human subject. In another embodiment, between 26 μg and 1.76 mg $Br^-$ per kg body weight can be administered to a subject, such as an animal patient. In other embodiments, less than 26 μg can be administered to a subject.

Embodiments of the invention comprise a pharmaceutical composition for preventing or treating cardiovascular disease in a subject, the composition comprising an amount between 1-250 mg of $Br^-$ ions. In embodiments, the subject is a human. In embodiments, the subject is a non-human mammal such as but not limited to a dog, cat, horse, cow, goat, or sheep. In embodiments, the composition is a drug, medical device, or dietary supplement. In embodiments, the composition is formulated as a pill, a patch, a liquid, an injectable liquid, a powder, a lozenge, a food, a drink, a candy, or a gum. In embodiments, the composition is administered to a subject. In embodiments, the composition is administered with at least one additional drug, medical device, food, drink, or dietary supplement to a subject. In embodiments, the additional drug is administered to treat or prevent a symptom of heart disease, kidney disease, obesity, metabolic syndrome, diabetes, or cancer.

Embodiments of the invention provide for methods and compositions suitable for preventing a disease of the circulatory system, a cardiovascular disease or a kidney disease. Embodiments of the invention provide for methods and compositions suitable for preventing a disease of the circulatory system, a cardiovascular disease or a kidney disease in certain populations who are at high risk for developing said diseases. Non-limiting examples of such populations include dialysis patients, subjects with diabetes or metabolic syndrome, subjects with kidney disease, subjects who are obese and/or overweight, subjects with cancer, smokers, and subjects consuming a high salt diet. In another embodiment, the invention comprises administering a low dose of $Br^-$, less than 1 mg $Br^-$, or an amount between 1 and 250 mg of $Br^-$ to a subject who is at risk of developing a disease of the circulatory system, a cardiovascular disease, or a kidney disease. In another embodiment, the invention comprises administering less than 1 mg of $Br^-$ to a subject who is at risk of developing a disease of the circulatory system, a cardiovascular disease, or a kidney disease. Such preventative practices are within the scope of the invention. In another embodiment, the invention comprises administering $Br^-$ to ameliorate the symptoms of a disease of the circulatory system, a cardiovascular disease, or a kidney disease. Described herein are compositions and methods which enable one skilled in the art to effectively perform this method.

Embodiments of the invention provide for methods and compositions for treating or preventing symptoms of a disease of the circulatory system, a cardiovascular disease or a kidney disease in a subject. Non-limiting examples of diseases and symptoms that can be treated by the invention include cardiovascular disease; vascular disease; kidney disease, including chronic kidney disease, glomerular disease, and tubular disease; kidney injury, including acute kidney injury, sepsis-induced kidney injury, drug-induced kidney injury, hypovolemia-induced kidney injury, and ischemic kidney injury; fibrosis; hypertension, including salt-sensitive hypertension; heart attack; heart failure; cardiac remodeling; atherosclerosis; stroke; arterial stiffening; vascular wall thickening; thickening of the peritoneal membrane; dyslipidema; blood clot; anemia; an acid-base imbalance; or hypercholemia.

In another embodiment, the invention comprises a method for the diagnostic identification of those subjects would best respond to the treatment embodiments of the invention. In some embodiments, the subject can benefit if $Br^-$ levels in blood or serum are at or below 20 μM, or if urinary excretion rates of $Na^+$ and/or $Cl^-$ are elevated above normal value for that patient or above what is otherwise considered a healthy range.

In other embodiments, the invention comprises methods for identifying a subject at risk of developing a disease of the circulatory system, a cardiovascular disease, or a kidney disease. In some embodiments, the subject can be at risk (1) if serum or blood $Br^-$ levels are between 20 μM and 40 μM; (2) if the subject is being treated with dialysis; (3) if the subject is being treated with a diuretic; (4) if dietary $Na^+$ consumption is above 2300 mg per day; (5) if dietary consumption is above 3545 mg per day.

As used herein, "biomarker(s)" and "bio-indicator(s)" are interchangeable. In embodiments of the invention, bio-indicators as described herein, such as levels of $Br^-$ and/or levels of natriuretic peptides (such as ANP and/or BNP), can be measured in biological samples, such as biological fluids. Non-limiting examples of biological fluids include saliva, blood, serum, plasma, spent or used dialysate, sweat, or urine. Such measurements can be made using techniques known to the art, non-limiting examples of such standard clinical chemistry techniques include column chromatography, inductively coupled plasma mass spectrometry, x-ray florescence, and neutron activation analysis. Alternatively, the effects of Br-deficiency can be monitored using techniques that detect changes in collagen IV-rich extracellular matrices, such as using ultrasonography to monitor thickness of carotid vessel wall, or other appropriate vessel walls.

In yet another embodiment of the invention, the invention comprises a composition that is a parenteral admixture or parenteral nutrition, for parenteral administration to a subject, that is supplemented with $Br^-$. In embodiments, the composition can provide subjects with low doses of $Br^-$. The composition can comprise a therapeutically effective amount of $Br^-$. In one embodiment, the parenteral composition is supplemented with $Br^-$ to provide a subject with a sufficient amount of $Br^-$ to treat or prevent $Br^-$ deficiency. In still other embodiments, the parenteral composition is supplemented with $Br^-$ to provide a subject with a sufficient amount of $Br^-$ to treat or prevent a disease, such as a disease of the circulatory system, a cardiovascular disease, cancer, an endocrinopathy (e.g., diabetes, obesity, metabolic syndrome), or a kidney disease. For example, the parenteral composition is supplemented with a low dose of $Br^-$, less than 1 mg $Br^-$, between 1 mg and 250 mg $Br^-$, less than 30 μM $Br^-$ or between 30 μM and 300 μM of $Br^-$. The parenteral composition can be used as a total or partial source of nutrition for patients who are unable to obtain adequate nutrition from alternative routes. Parenteral admixtures or parenteral nutrition can be used for administering embodiments of the invention to patients with renal failure, other forms of kidney disease, or cardiovascular disease.

Examples of subjects who can benefit from embodiments of the invention include subjects, such as human patients, receiving enteral or parental nutrition. Such subjects, for example, can benefit from a nutritionally effective amount of a composition as described herein. For example, such subjects can receive purified diets as their sole source of nutrition. Other examples of such subjects that can benefit from embodiments of the invention include human patients receiving total parental nutrition. Additional subjects who can benefit from embodiments of the invention include those who receive their formulated meals under the supervision of a nutrition specialist, who can also be a physician. Moreover, subjects that can benefit from embodiments of the invention are often suffering from other medical conditions and can benefit from maintaining adequate amounts of dietary $Br^-$.

In another embodiment, the invention is administered to the patient as a medical device. The device can be readily prepared from standard or existing medical devices by simply increasing the amount of $Br^-$ to a final concentration that is within the scope of the invention. For example, each device can contain a low dose of $Br^-$, less than 1 mg $Br^-$, or between 1 mg and 250 mg $Br^-$. For example, the device can be a collagen-based wound healing device, a plug, a patch, a stent, an intravascular balloon, a catheter, a bandage, a powder, or another device that contains a low dose of $Br^-$, less than 1 mg $Br^-$, or between 1 mg and 250 mg of $Br^-$ In yet another embodiment, the invention comprises a drug that provides a therapeutically effective amount of $Br^-$ to a subject, such as a subject with cardiovascular disease or kidney disease. In one example, the invention provides a therapeutically or nutritionally effective amount of a $Br^-$ salt to a subject. In another embodiment, the invention provides an effective amount of a $Br^-$ salt in combination with another drug or device to a subject. In yet another embodiment, the invention is useful for counteracting, reversing, or minimizing the side effects of another drug in a patient. For example, the invention can be used to treat a disease of the circulatory system, a cardiovascular disease, a vascular disease, kidney injury, or a kidney disease that develops as a side effect of another drug, such as a nonsteroidal anti-inflammatory drug or a cancer chemotherapeutic drug. As another example, the invention can be used to counteract, reverse, or minimize the side effects of another drug used to treat a symptom of cardiovascular disease or kidney disease, such as a medication used to treat hypertension including a thiazide diuretic, thiazide-like diuretic, or loop diuretic. Embodiments of the invention can be administered to such subjects, for example, and can enhance the overall effectiveness of the treatments, lower treatment-associated risk, and improve the overall prognosis for the patient.

In yet another embodiment, the invention comprises a therapeutic animal drug for use in preventing or treating diseases in an animal, such as cardiovascular disease or kidney disease in animals. In embodiments, the drug can be used for veterinary purposes. The therapeutic animal drug can comprise a therapeutically effective amount of $Br^-$, such as a low dose of $Br^-$. Non-limiting examples of veterinary uses comprise treating feline heart disease, feline cardiomyopathy, feline kidney disease, canine heart disease, or canine kidney disease.

One skilled in the art will appreciate that a fundamental advantageous utility of the invention comprises the method of preventing or treating a disease, such as a disease of the circulatory system, a cardiovascular disease or a kidney disease with an appropriate amount of $Br^-$ ions, such as low doses of $Br^-$, as defined herein. Consequently, this method can be practiced through various compositions that are formulated and/or purposefully manufactured to contain an appropriate amount of $Br^-$ ions. Non-limiting examples of compositions including solutions, washes, rinses, creams, tonics, shampoos, toothpastes, lotions, ointments, pills, powders, dialysates, dissolvable strips, patches, and other formulations that are well-suited for addressing a symptom of Br-deficiency. These various compositions are within the scope of the invention since they are unified by the common method of administering an appropriate amount of $Br^-$ to subjects with or at risk of developing cardiovascular disease or kidney disease.

In yet another embodiment, the invention comprises a method for treating or preventing one or more symptoms of a disease, such as cardiovascular disease or kidney disease. Non-limiting examples of diseases and symptoms of cardiovascular disease include vascular disease, hypertension, salt-sensitive hypertension, heart attack, stroke, thrombosis, coronary artery disease, ischemic heart disease, peripheral artery disease, arterial stiffening, atherosclerosis, vascular wall thickening, dyslipidema, blood clot, and anemia. Non-limiting examples of diseases and symptoms of kidney disease include acute kidney injury, chronic kidney disease, end stage renal disease glomerular disease, tubular disease, hyperchlolemia, and an acid-base imbalance.

In one embodiment, the subject being treated with the invention is also being treated with a renal replacement therapy. In another embodiment, said subject being treated with the invention is also being treated with dialysis. In yet another embodiment, the symptom that indicates practice of the invention is thickening of the peritoneal membrane.

In one embodiment, one or more disease symptoms of cardiovascular disease or kidney disease appear after the appearance of a preceding medical condition. Non-limiting examples of a preceding medical condition include sepsis or hypovolemia. In yet another embodiment, one or more disease symptoms of cardiovascular disease and kidney disease appear after the subject is administered a drug.

By practicing the invention, these symptoms can be treated by administering an effective amount of $Br^-$ to the subject. In practicing the invention, the subject can require administration of low doses of $Br^-$, less than 1 mg of $Br^-$, between 1-5 mg of $Br^-$, or between 5 and 250 mg $Br^-$. Alternatively, in practicing the invention, some subjects can benefit from being administered between 6-7 mg of $Br^-$. Even still other subjects can be treated with 8-10 mg of $Br^-$ during practice of the invention. Yet other subjects can be treated with 11-15 mg of $Br^-$ during practice of the invention. Yet other subjects can be treated with 16-25 mg of $Br^-$ during practice of the invention. Embodiments of the invention enable said subject to be treated with any concentration of $Br^-$ between 1-250 mg.

In one embodiment, the invention comprises administered $Br^-$ in the form of NaBr. In yet another embodiment, the invention comprises administering $Br^-$ in the form of KBr. In yet another embodiment, the invention comprises administering $Br^-$ in the form of $MgBr_2$. In yet another embodiment, the invention comprises administering $Br^-$ in any ionic salt of $Br^-$ that is acceptable for dietary consumption or pharmaceutical use.

In yet another embodiment, the invention comprises formulating $Br^-$ as a medical device for use in preventing or treating cardiovascular disease or kidney disease. In yet another embodiment, the invention comprises formulating $Br^-$ as a pharmaceutical drug or drug ingredient for use in preventing or treating cardiovascular disease or kidney disease.

In one embodiment, the invention comprises treating a disease of the circulatory system, a cardiovascular disease or a kidney disease in a mammal subject, including but not limited to a human, an animal, a dog, or a cat.

In yet another embodiment, the invention comprises administering an effective amount of $Br^-$ to treat or prevent a disease of the circulatory system, a cardiovascular disease or a kidney disease in a subject who is also being treated with dialysis, including maintenance dialysis, hemodialysis, home hemodialysis, peritoneal dialysis, or continuous renal replacement therapy.

In one embodiment, the invention comprises administering a $Br^-$ salt to a subject who has or is at risk of developing a disease of the circulatory system, a cardiovascular disease or a kidney disease. In another embodiment, the invention comprises administering a $Br^-$ salt in combination with another pharmaceutical agent. Non-limiting examples of pharmaceutical agents include a loop diuretic, thiazide diuretic, thiazide-like diuretic, vasodilator, renin inhibitor, dopamine, dopamine receptor agonist, angiotensin converting enzyme inhibitor, angiotensin receptor blocking agent, beta-adrenergic blocking agent, alpha blocking agent, alpha agonist, sodium channel blocking agent, calcium channel blocking agent, statin therapy, nonsteroidal anti-inflammatory drug, thrombolytic agent, or cancer chemotherapy.

In another embodiment, the invention comprises a method of preventing a disease of the circulatory system, a cardiovascular disease or a kidney disease in a subject. In embodiments, the method comprises obtaining a sample from a subject, measuring the $Br^-$ concentration in the sample from the subject, comparing the measured concentration to that of a control sample, and determining the subject to be at risk of developing cardiovascular disease or kidney disease if the $Br^-$ serum concentration is below 20 μM. The method can further comprise administering a therapeutically effective amount of $Br^-$ to the subject to prevent a disease of the circulatory system, a cardiovascular disease or a kidney disease. In embodiments, the sample can be a biological sample, such a biological fluid. Non-limiting examples of such biological fluids comprise whole blood, serum plasma urine, saliva, or sweat. $Br^-$ concentration in the biological sample can be measured by techniques known in the art. Non-limiting example of such techniques include column chromatography, mass spectrometry, or mass spectrometry. For example, the serum $Br^-$ concentration can be measured using commonly employed diagnostic techniques, including column chromatography or mass spectrometry. In yet another embodiment, the serum Br⁻ concentration is measured using inductively coupled plasma mass spectrometry. In yet another embodiment, the Br⁻ concentration is directly measured from a body fluid other than serum, and a conversion factor is used to obtain the serum Br⁻ concentration. In still another embodiment, the concentration of Br⁻ is directly measured in a biological sample other than serum, and the clinically actionable threshold for administering Br⁻ to a subject is determined directly from the amount of Br⁻ in the non-serum biological sample. In an embodiment, a clinically actionable threshold is based on the biological ratio of the amount of Br⁻ in the non-serum biological sample and the amount of Br⁻ in serum. For example, the clinically actionable threshold is 20 µM serum Br⁻ or the measurement in the biological sample that is equivalent to 20 µM serum Br⁻.

In embodiments, the serum Br⁻ concentration can be calculated from a non-serum biologic sample using the equations below:

$$k = \frac{\text{serum}[Br-]}{\text{non-serum}[Br-]}$$

Which can be solved to give:

Serum [Br—]=$k$(non-serum[Br—])

Where serum [Br⁻] is the molar concentration of Br⁻ in serum; non-serum [Br⁻] is the molar concentration of Br⁻ in a specific non-serum biologic sample, where nonlimiting examples include saliva, urine, and/or sweat; and k the normal ratio between serum [Br⁻] and said non-serum [Br⁻] in healthy adults.

Embodiments comprise a method for treatment of disease in a subject comprising administering to the subject a therapeutically effective amount of Br⁻ in an amount no greater than that require to result in a body fluid concentration no greater than 300-500 µM Br⁻. In embodiments, Br⁻ is administered in a pharmaceutically acceptable carrier or salt thereof. In embodiments, the disease comprises a disease of the circulatory system, a cardiovascular disease, a kidney disease, or a combination thereof. In embodiments, Br⁻ is administered at a dose no greater than about 100 mg Br⁻ to about 250 mg Br⁻. In some embodiments, Br— is administered at a dose of 100 mg, 101 mg, 102 mg, 103 mg, 104 mg, 105 mg, 106 mg, 107 mg, 108 mg, 109 mg, 110 mg, 111 mg, 112 mg, 113 mg, 114 mg, 115 mg, 116 mg, 117 mg, 118 mg, 119 mg, 120 mg, 121 mg, 122 mg, 123 mg, 124 mg, 125 mg, 126 mg, 127 mg, 128 mg, 129 mg, 130 mg, 131 mg, 132 mg, 133 mg, 134 mg, 135 mg, 136 mg, 137 mg, 138 mg, 139 mg, 140 mg, 141 mg, 142 mg, 143 mg, 144 mg, 145 mg, 146 mg, 147 mg, 148 mg, 149 mg, 150 mg, 151 mg, 152 mg, 153 mg, 154 mg, 155 mg, 156 mg, 157 mg, 158 mg, 159 mg, 160 mg, 161 mg, 162 mg, 163 mg, 164 mg, 165 mg, 166 mg, 167 mg, 168 mg, 169 mg, 170 mg, 171 mg, 172 mg, 173 mg, 174 mg, 175 mg, 176 mg, 177 mg, 178 mg, 179 mg, 180 mg, 181 mg, 182 mg, 183 mg, 184 mg, 185 mg, 186 mg, 187 mg, 188 mg, 189 mg, 190 mg, 191 mg, 192 mg, 193 mg, 194 mg, 195 mg, 196 mg, 197 mg, 198 mg, 199 mg, 200 mg, 201 mg, 202 mg, 203 mg, 204 mg, 205 mg, 206 mg, 207 mg, 208 mg, 209 mg, 210 mg, 211 mg, 212 mg, 213 mg, 214 mg, 215 mg, 216 mg, 217 mg, 218 mg, 219 mg, 220 mg, 221 mg, 222 mg, 223 mg, 224 mg, 225 mg, 226 mg, 227 mg, 228 mg, 229 mg, 230 mg, 231 mg, 232 mg, 233 mg, 234 mg, 235 mg, 236 mg, 237 mg, 238 mg, 239 mg, 240 mg, 241 mg, 242 mg, 243 mg, 244 mg, 245 mg, 246 mg, 247 mg, 248 mg, 249 mg, or 250 mg Br⁻.

Embodiments comprise a pharmaceutical composition comprising a dose of Br⁻ in an amount no greater than that required to result in a body fluid concentration no greater than 300-500 µM Br⁻. In embodiments, Br⁻ is administered in a pharmaceutically acceptable carrier or salt thereof. In embodiments, the composition comprises an amount of Br⁻ no greater than 100-250 mg Br⁻. Embodiments comprise methods of administering Br⁻ to a subject for a period of time, and further comprising a daily dose of about 0.3 mg to about 25 mg. In embodiments, a dose of 0.3 mg, 0.4 mg, 0.5 mg, 0.6 mg, 0.7 mg, 0.8 mg, 0.9 mg, 1.0 mg, 1.1 mg, 1.2 mg, 1.3 mg, 1.4 mg, 1.5 mg, 1.6 mg, 1.7 mg, 1.8 mg, 1.9 mg, 2.0 mg, 2.1 mg, 2.2 mg, 2.3 mg, 2.4 mg, 2.5 mg, 2.6 mg, 2.7 mg, 2.8 mg, 2.9 mg, 3.0 mg, 3.1 mg, 3.2 mg, 3.3 mg, 3.4 mg, 3.5 mg, 3.6 mg, 3.7 mg, 3.8 mg, 3.9 mg, 4.0 mg, 4.1 mg, 4.2 mg, 4.3 mg, 4.4 mg, 4.5 mg, 4.6 mg, 4.7 mg, 4.8 mg, 4.9 mg, 5.0 mg, 5.1 mg, 5.2 mg, 5.3 mg, 5.4 mg, 5.5 mg, 5.6 mg, 5.7 mg, 5.8 mg, 5.9 mg, 6.0 mg, 6.1 mg, 6.2 mg, 6.3 mg, 6.4 mg, 6.5 mg, 6.6 mg, 6.7 mg, 6.8 mg, 6.9 mg, 7.0 mg, 7.1 mg, 7.2 mg, 7.3 mg, 7.4 mg, 7.5 mg, 7.6 mg, 7.7 mg, 7.8 mg, 7.9 mg, 8.0 mg, 8.1 mg, 8.2 mg, 8.3 mg, 8.4 mg, 8.5 mg, 8.6 mg, 8.7 mg, 8.8 mg, 8.9 mg, 9.0 mg, 9.1 mg, 9.2 mg, 9.3 mg, 9.4 mg, 9.5 mg, 9.6 mg, 9.7 mg, 9.8 mg, 9.9 mg, 10.0 mg, 10.1 mg, 10.2 mg, 10.3 mg, 10.4 mg, 10.5 mg, 10.6 mg, 10.7 mg, 10.8 mg, 10.9 mg, 11.0 mg, 11.1 mg, 11.2 mg, 11.3 mg, 11.4 mg, 11.5 mg, 11.6 mg, 11.7 mg, 11.8 mg, 11.9 mg, 12.0 mg, 12.1 mg, 12.2 mg, 12.3 mg, 12.4 mg, 12.5 mg, 12.6 mg, 12.7 mg, 12.8 mg, 12.9 mg, 13.0 mg, 13.1 mg, 13.2 mg, 13.3 mg, 13.4 mg, 13.5 mg, 13.6 mg, 13.7 mg, 13.8 mg, 13.9 mg, 14.0 mg, 14.1 mg, 14.2 mg, 14.3 mg, 14.4 mg, 14.5 mg, 14.6 mg, 14.7 mg, 14.8 mg, 14.9 mg, 15.0 mg, 15.1 mg, 15.2 mg, 15.3 mg, 15.4 mg, 15.5 mg, 15.6 mg, 15.7 mg, 15.8 mg, 15.9 mg, 16.0 mg, 16.1 mg, 16.2 mg, 16.3 mg, 16.4 mg, 16.5 mg, 16.6 mg, 16.7 mg, 16.8 mg, 16.9 mg, 17.0 mg, 17.1 mg, 17.2 mg, 17.3 mg, 17.4 mg, 17.5 mg, 17.6 mg, 17.7 mg, 17.8 mg, 17.9 mg, 18.0 mg, 18.1 mg, 18.2 mg, 18.3 mg, 18.4 mg, 18.5 mg, 18.6 mg, 18.7 mg, 18.8 mg, 18.9 mg, 19.0 mg, 19.1 mg, 19.2 mg, 19.3 mg, 19.4 mg, 19.5 mg, 19.6 mg, 19.7 mg, 19.8 mg, 19.9 mg, 20.0 mg, 20.1 mg, 20.2 mg, 20.3 mg, 20.4 mg, 20.5 mg, 20.6 mg, 20.7 mg, 20.8 mg, 20.9 mg, 21.0 mg, 21.1 mg, 21.2 mg, 21.3 mg, 21.4 mg, 21.5 mg, 21.6 mg, 21.7 mg, 21.8 mg, 21.9 mg, 22.0 mg, 22.1 mg, 22.2 mg, 22.3 mg, 22.4 mg, 22.5 mg, 22.6 mg, 22.7 mg, 22.8 mg, 22.9 mg, 23.0 mg, 23.1 mg, 23.2 mg, 23.3 mg, 23.4 mg, 23.5 mg, 23.6 mg, 23.7 mg, 23.8 mg, 23.9 mg, 24.0 mg, 24.1 mg, 24.2 mg, 24.3 mg, 24.4 mg, 24.5 mg, 24.6 mg, 24.7 mg, 24.8 mg, 24.9 mg, or 25.0 mg Br⁻ is administered to a subject, for example every 2 hours, 4 hours, 8 hours, 10 hours, 12 hours or 24 hours.

In embodiments, the period of time is 1 to 5 days, 5 to 10 days, 10 to 30 days, 1 month, 2 to 12 months, or greater than 1 year. In embodiments, the daily dose is about 2-5 mg Br⁻. In other embodiments, the daily dose is about 6-10 mg Br⁻. In embodiments, the daily dose does not exceed 25 mg Br⁻.

Embodiments of the invention comprise treating a subject that is suffering from cardiovascular disease, kidney disease, diabetes, obesity, metabolic syndrome, cancer, or a combination thereof with a therapeutically effective amount of a pharmaceutical composition comprising a dose of Br⁻ in an amount no greater than that required to result in a body fluid concentration no greater than 300-500 µM Br⁻. In embodiments, administration of the composition results in a body fluid concentration of no greater than 50, 100, 200, 300, 400 or 500 µM Br⁻. In some embodiments, the cardiovascular disease comprises one or more symptoms of vascular disease, hypertension, heart attack, stroke, thrombosis, coronary artery disease, ischemic heart disease, heart failure, cardiac remodeling, cardiac fibrosis, peripheral artery disease, arterial stiffening, atherosclerosis, vascular wall thickening, dyslipidemia, blood clot, anemia, or any combination thereof. In other embodiments, the kidney disease comprises one or more symptoms of acute kidney injury, chronic kidney disease, end stage renal disease, glomerular disease, tubular disease, hyperchlolemia, an acid-base imbalance, or any combination thereof. In yet another embodiment, the composition comprises Br$^-$ and a pharmaceutically acceptable carrier or salt thereof. In yet another embodiment, the composition comprises an amount of Br$^-$ no greater than 250 mg.

Embodiments of the invention comprise administering Br$^-$ to a subject for a period of time. In some embodiments, the period of time comprises 1 to 5 days, 5 to 10 days, 10 to 30 days, 1 month, 2 to 12 months, or greater than 1 year.

Embodiments of the invention comprise administering Br$^-$ as a daily dose. In some embodiments, the daily dose comprises about 0.2 mg Br$^-$ to about 18 mg Br$^-$. In other embodiments, the daily dose is no more than about 25 mg Br$^-$.

Embodiments of the invention comprise a method that can be used to identify a subject who would benefit from administration of a therapeutically effective amount of Br$^-$ or Br-comprising composition, such as an amount sufficient to maintain the serum Br$^-$ level to an amount between about 50 μM and about 1 mM. In some embodiments, said subject displays one or more of the following: systolic blood pressure that displays a clinically meaningful difference compared to baseline levels, healthy levels, normal levels, or medically acceptable systolic blood pressure reference values; diastolic blood pressure that displays clinically meaningful difference compared to baseline levels, healthy levels, normal levels, or medically acceptable diastolic blood pressure reference values; heart rate that displays a clinically meaningful difference compared to baseline levels, healthy levels, normal levels, or medically acceptable heart rate reference values; cardiac fibrosis; salt sensitive hypertension; glomerular filtration rate less than 60 ml/min/1.73 m2; urine albumin levels that display a clinically meaningful elevation over baseline levels, healthy levels, normal levels, or medically acceptable reference values; serum levels of BNP, ANP, or pro-BNP that display a clinically meaningful difference compared to baseline levels, healthy levels, normal levels, or medically acceptable reference values; or urinary or plasma cyclic guanosine monophosphate (cGMP) levels that display a clinically meaningful difference compared to baseline levels, healthy levels, normal levels, or medically acceptable reference values. In some embodiments, after said subject has been identified using methods as described herein, a Br$^-$ or Br-comprising composition is administered to the subject, such as an amount of Br$^-$ or Br-comprising composition sufficient to maintain the serum Br$^-$ level to an amount between about 50 μM and about 1 mM.

Embodiments of the invention comprise a method for identifying a subject who is in need of a treatment as described herein, such as administration of between about 1 mg and about 250 mg of Br$^-$. In an embodiment, the method comprises monitoring a biomarker of cardiovascular disease or kidney disease in a subject and administering a composition as described herein to the subject if the subject displays a biomarker or biomarker signature of cardiovascular disease or kidney disease. Some embodiments comprise administering to the subject a therapeutically effective amount of a composition as described herein, such as an amount of Br$^-$ sufficient to maintain the serum Br$^-$ level to an amount between about 50 μM and about 1 mM. Non-limiting examples of such biomarkers of cardiovascular disease and/or kidney disease comprise one or more of systolic blood pressure that is higher than 120 mm Hg, diastolic blood pressure that is higher than 80 mm Hg, average resting heart rate that higher than 100 beats per minute; glomerular filtration rate less than 60 ml/min/1.73 m2, or urine albumin levels over 30 mg/g.

The Br$^-$ or Br-comprising composition can be provided in a kit. In one embodiment, the kit includes (a) a container that contains the Br$^-$ or Br-comprising composition, and optionally (b) informational material. The informational material can be descriptive, instructional, marketing or other material that relates to the methods described herein and/or the use of the agents for therapeutic benefit. In an embodiment, the kit includes also includes a second agent, such as a pharmaceutical drug as described herein. For example, the kit includes a first container that contains the Br$^-$ composition, and a second container that includes the pharmaceutical drug. As another example, the kit includes a container that contains the Br$^-$ composition in combination with the pharmaceutical drug.

The informational material of the kits is not limited in its form. In one embodiment, the informational material can include information about production of the compound, molecular weight of the compound, concentration, date of expiration, batch or production site information, and so forth. In one embodiment, the informational material relates to methods of administering the Br$^-$ composition, e.g., in a suitable dose, dosage form, or mode of administration (e.g., a dose, dosage form, or mode of administration described herein), to treat a subject. The information can be provided in a variety of formats, include printed text, computer readable material, video recording, or audio recording, or an information that provides a link or address to substantive material.

In addition to the Br$^-$, the composition in the kit can include other ingredients, such as a solvent or buffer, a stabilizer, or a preservative. When the composition is provided in a liquid solution, the liquid solution preferably is an aqueous solution. When the composition is provided as a dried form, reconstitution generally is by the addition of a suitable solvent. The solvent, e.g., sterile water or buffer, can optionally be provided in the kit.

The kit can include one or more containers for the Br$^-$ composition or compositions containing Br$^-$. In some embodiments, the kit contains separate containers, dividers or compartments for the composition and informational material. For example, the composition can be contained in a bottle, vial, or syringe, and the informational material can be contained in a plastic sleeve or packet. In other embodiments, the separate elements of the kit are contained within a single, undivided container. For example, the composition is contained in a bottle, vial or syringe that has attached thereto the informational material in the form of a label. In some embodiments, the kit includes a plurality (e.g., a pack) of individual containers, each containing one or more unit dosage forms (e.g., a dosage form described herein) of the agents. The containers can include a combination unit dosage in a desired ratio. For example, the kit includes a plurality of syringes, ampules, foil packets, blister packs, or medical devices, e.g., each containing a single combination unit dose. The containers of the kits can be air tight, waterproof (e.g., impermeable to changes in moisture or evaporation), and/or light-tight. The kit optionally includes a device suitable for administration of the composition, e.g., a syringe or other suitable delivery device. The device can be provided pre-loaded with one or both of the agents or can be empty, but suitable for loading.

Embodiments of the invention are amenable to a variety of formulations, non-limiting examples of which comprise a pill, a patch, a liquid, an injectable liquid, a powder, a lozenge, a food, a drink, a candy, or a gum. Certain embodiments are not formulated for inhalation. Further, certain embodiments are not formulated with thiocyanate. Liquid embodiments are not formulated with greater than 1% sodium chloride. Certain embodiments are not formulated as eye drops. Embodiments can be formulated for systemic administration to a subject, such as but not limited to injection or oral administration.

Some embodiments of the invention are combined into a combination formulation with another pharmaceutical drug, such as those to treat cardiovascular disease, diabetes, cancer, or obesity. For example, an embodiment comprises manufacturing and packaging a combination drug product that comprises an embodiment of the invention and a drug for treating diabetes. Some embodiments are manufactured separately but combined with another pharmaceutical drug prior to administration to a subject, where a non-limited example is combining a liquid embodiment and a liquid diuretic for administration as a single treatment to a subject. Embodiments of the invention can be combined with another other drug listed herein.

Embodiments of the invention can be packed for single dose administration to a subject, such as not but limited to a single injection of an embodiment to a hospitalized subject. Some embodiments can be packaged for repeated dosing of a subject, such as but not limited to a pill bottle containing a multi-day supply of embodiments or a bubble strip containing a multi-day supply of embodiments.

Embodiments can be administered through one or more formulations and packaging formats. A non-limiting example comprises administering embodiments as a daily pill to a subject, where the pill is self-administered at home, and administering injection embodiments to the same subject during regular office visits.

Some embodiments comprise administering doses of $Br^-$ at differing concentrations over a period of time in order to achieve the desired circulating $Br^-$ level in the blood, serum, or plasma of a subject. For example, a subject can be administered a composition comprising a high dose of $Br^-$, such as but not limited to 15-25 mg $Br^-$, followed by subsequent administration of lower doses of $Br^-$, such as but not limited to 1-5 mg $Br^-$ a period time thereafter. This approach can benefit a subject who has serum $Br^-$ levels below 20 μM, where the initial large dose serves to restore serum $Br^-$ levels to between about 50 μM and about 500 μM while the subsequently administered lower doses of $Br^-$ serve to maintain the serum $Br^-$ levels in this range. Another non-limiting example includes administering compositions comprising increasing doses of $Br^-$ to a subject until a desired maintenance dosing is achieved, such as but not limited to increasing dosing from 1 mg $Br^-$ to 3 mg $Br^-$ to 5 mg $Br^-$ and so on until a maintenance dose of 10 mg $Br^-$ is achieved. Still another non-limiting example includes administering a daily maintenance dose of 5 mg $Br^-$ with periodic injections of larger doses such as but not limited to 10 mg $Br^-$, 15 mg $Br^-$, 20 mg $Br^-$, or 25 mg $Br^-$.

Importantly, in order to prevent toxicity, embodiments as described herein do not provide for administering sufficient amounts of $Br^-$ to raise the circulating $Br^-$ concentration above 1 mM in a subject, particularly if two or more separate compositions, each comprising Br—, are administered to the same subject. As a non-limiting example, if a subject is administered a combination of two or more drug formulations each containing Br—, for example a first drug for controlling diabetes combined with a second drug for controlling hypertension, it would be out of scope of the invention for the subject's blood concentration of $Br^-$ to rise above 1 mM. Thus, embodiments as described herein comprise only administering sufficient $Br^-$ to raise and maintain circulating $Br^-$ concentration above at least 20 μM $Br^-$ but not more than 1 mM. Further embodiments administer sufficient $Br^-$ to achieve circulating $Br^-$ concentrations above 50 μM but below 500 μM $Br^-$.

DETAILED DESCRIPTIONS OF THE INVENTION

Abbreviations and Definitions

Figure 1:
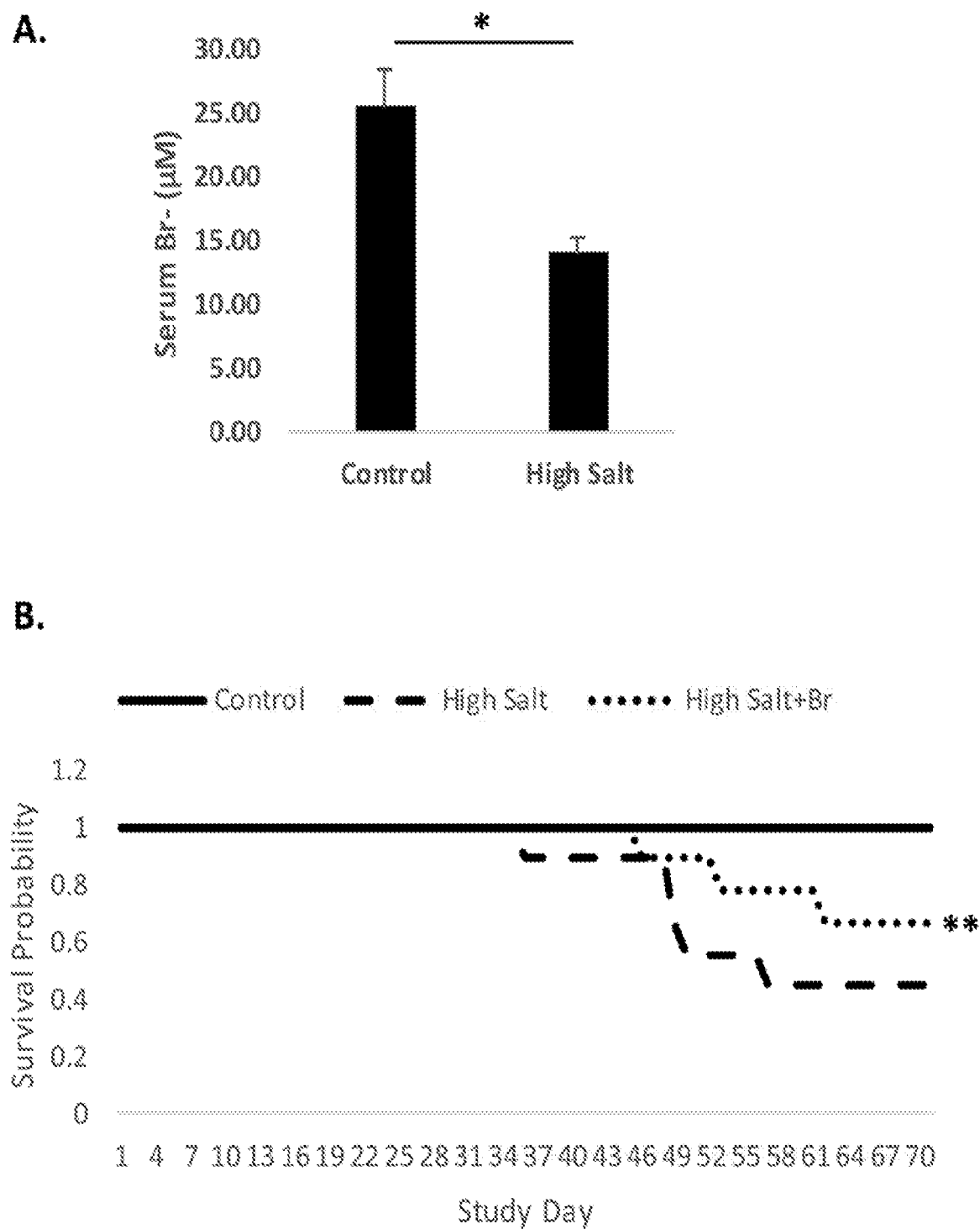
FIG. 1 shows $Br^-$ significantly increases survival in salt sensitive Dahl Rats. (A) Dahl rats on AIN76A+8% NaCl display significantly lower serum $Br^-$ levels compared to Dahl rats on AIN76A diet (mean: 14.14 μM vs. 25.54 μM, respectively; *, p<0.001, T-test), indicating that an important threshold for inducing symptoms of Br-deficiency occurs at or near 20 μM. High salt is known to induce symptoms of cardiovascular disease and kidney disease in Dahl rats. In this study, mortality events appeared after rats were on a high salt diet for approximately one month. *:p=0.0001, T-test. (B) Rats were administered a diet of AIN76A+8% NaCl with or without 300 mg NaBr per kg feed ("High Salt+Br" and "High Salt" study arms, respectively). Control rats received AIN76A without supplemental chloride or bromide. 9 rats per study arm. Significantly greater survival probability need in High Salt+Br compared to High Salt alone (log rank test), demonstrating ability of $Br^-$ to improve preclinical mortality rates caused by high salt diet. **:p<0.001, Log-Rank.

Detailed descriptions of one or more embodiments are provided herein. It is to be understood, however, that the invention can be embodied in various forms. Therefore, specific details disclosed herein are not to be interpreted as limiting, but rather as a basis for the claims and as a representative basis for teaching one skilled in the art to employ the invention in any appropriate manner.

The terms for "bromine" and "bromide" are often used interchangeably, even in some scientific or medical publications, and can be a source of confusion with respect to the invention. The term "bromine" is used herein in reference to the element; the term "bromide" refers to the ionic specie (Br⁻). "Bromide", when used herein by itself, does not refer to a molecule that contains a bromine atom that is covalently bound to the parent molecule. An example of such covalently-bound molecules is methyl bromide. Alternatively, the term "brominated" molecule can refer to a molecule that contains a covalently-bound bromine atom.

As used herein, a therapeutically effective amount of Br⁻ can be, for example, the amount of Br⁻ or Br-comprising composition, needed to raise the circulating levels of Br⁻ to those concentrations that are required for eliciting the desired biological response following administration. For example, in a subject with cardiovascular disease and with a serum Br⁻ concentration of about 15 μM, the desired biological response can be treating cardiovascular disease and a therapeutically effective amount of Br⁻ can be the amount of Br⁻ needed to raise the serum Br⁻ to an amount above about 20 μM but below about 1 mM, for example to an amount between about 50 μM to about 1 mM.

As used herein, a nutritionally effective amount of Br⁻ can be, for example, the amount of Br⁻ or Br-comprising composition needed to maintain the circulating levels of Br⁻ to those concentrations that are required for eliciting the desired biological response following administration. For example, the desired biological response can be preventing cardiovascular disease in a subject and a nutritionally effective amount of Br⁻ can be the amount of Br⁻ needed to maintain the serum Br⁻ levels in the subject between 50 μM and 1 mM.

In embodiments, low doses of Br⁻ or Br-comprising compositions are administered. In embodiments, only an amount of Br⁻ or Br-comprising composition sufficient to raise the circulating levels of Br⁻ above 20 μM is administered to the subject. In other embodiments, the invention comprises compositions comprising an amount of Br⁻ sufficient to raise the circulating levels of Br⁻ to an amount between about 20 μM and 1 mM. In embodiments, the amount of Br⁻ administered to a subject can be between about 0.1 mg and 250 mg Br⁻. For example, the amount can be between about 1 and 50 mg of Br⁻ that is administered to a human subject within a single 24 hour period. The composition comprising Br⁻ may be administered as a single dose or as multiple smaller doses that collectively administer a therapeutically effective amount of Br⁻ to the human subject. For application to non-human subjects, a nutritionally effective amount of Br⁻ shall comprise administering an amount of Br⁻ that is between 0.0008% and 0.5556% mg Br⁻ per kg body weight of the human or non-human subject.

Serum Br⁻ measurements provide a convenient bodily fluid for determining the amount of Br⁻ present in a subject. Br⁻ is also found in many other places within the body, including but not limited to whole blood, urine, plasma, saliva, sweat, hair, nails, and some cells including buccal cells. The Br⁻ concentration in many of these can be diagnostically measured, such as determining urinary or plasma Br⁻ concentrations. The term "serum Br⁻" used herein refers the amount of Br⁻ that was either (1) identified from a test performed on serum or (2) identified in a non-serum sample and converted into the equivalent serum Br⁻ value using a conversion factor.

The singular forms "a", "an" and "the" include plural reference unless the context clearly dictates otherwise. The use of the word "a" or "an" when used in conjunction with the term "comprising" in the claims and/or the specification can mean "one," but it is also consistent with the meaning of "one or more," "at least one," and "one or more than one."

Wherever any of the phrases "for example," "such as," "including" and the like are used herein, the phrase "and without limitation" is understood to follow unless explicitly stated otherwise. Similarly, "an example," "exemplary" and the like are understood to be non-limiting.

The term "substantially" allows for deviations from the descriptor that do not negatively impact the intended purpose. Descriptive terms are understood to be modified by the term "substantially" even if the word "substantially" is not explicitly recited.

The terms "comprising" and "including" and "having" and "involving" (and similarly "comprises", "includes," "has," and "involves") and the like are used interchangeably and have the same meaning. Specifically, each of the terms is defined consistent with the common United States patent law definition of "comprising" and is therefore interpreted to be an open term meaning "at least the following," and is also interpreted not to exclude additional features, limitations, aspects, etc. Thus, for example, "a process involving steps a, b, and c" means that the process includes at least steps a, b and c. Wherever the terms "a" or "an" are used, "one or more" is understood, unless such interpretation is nonsensical in context.

As used herein, the term "about" can refer to approximately, roughly, around, or in the region of. When the term "about" is used in conjunction with a numerical range, it modifies that range by extending the boundaries above and below the numerical values set forth. In general, the term "about" is used herein to modify a numerical value above and below the stated value by a variance of 20 percent up or down (higher or lower).

When used in reference to a particular disease, the term "with" refers to patients that currently have the disease, are at risk of developing the disease, or have recently recovered from the disease. For example, the phrase "patients with cardiovascular disease" can be used here in to reference patients with ongoing cardiovascular disease or patients with a risk factor of cardiovascular disease, such as but not limited to consuming a high salt diet. This phrase can also refer to a patient who has recently recovered from a form of cardiovascular disease, such as but not limited to recovering from a heart attack. As another example, the phrase "subjects with acute kidney injury" can be used here in to reference subjects with an ongoing kidney injury or subjects with a risk factor of acute kidney injury, such as but not limited to subjects with sepsis. This phrase can also refer to a subject who has recently recovered from an acute kidney injury.

Need for Therapeutic Administration of $Br^-$

Figure 4:
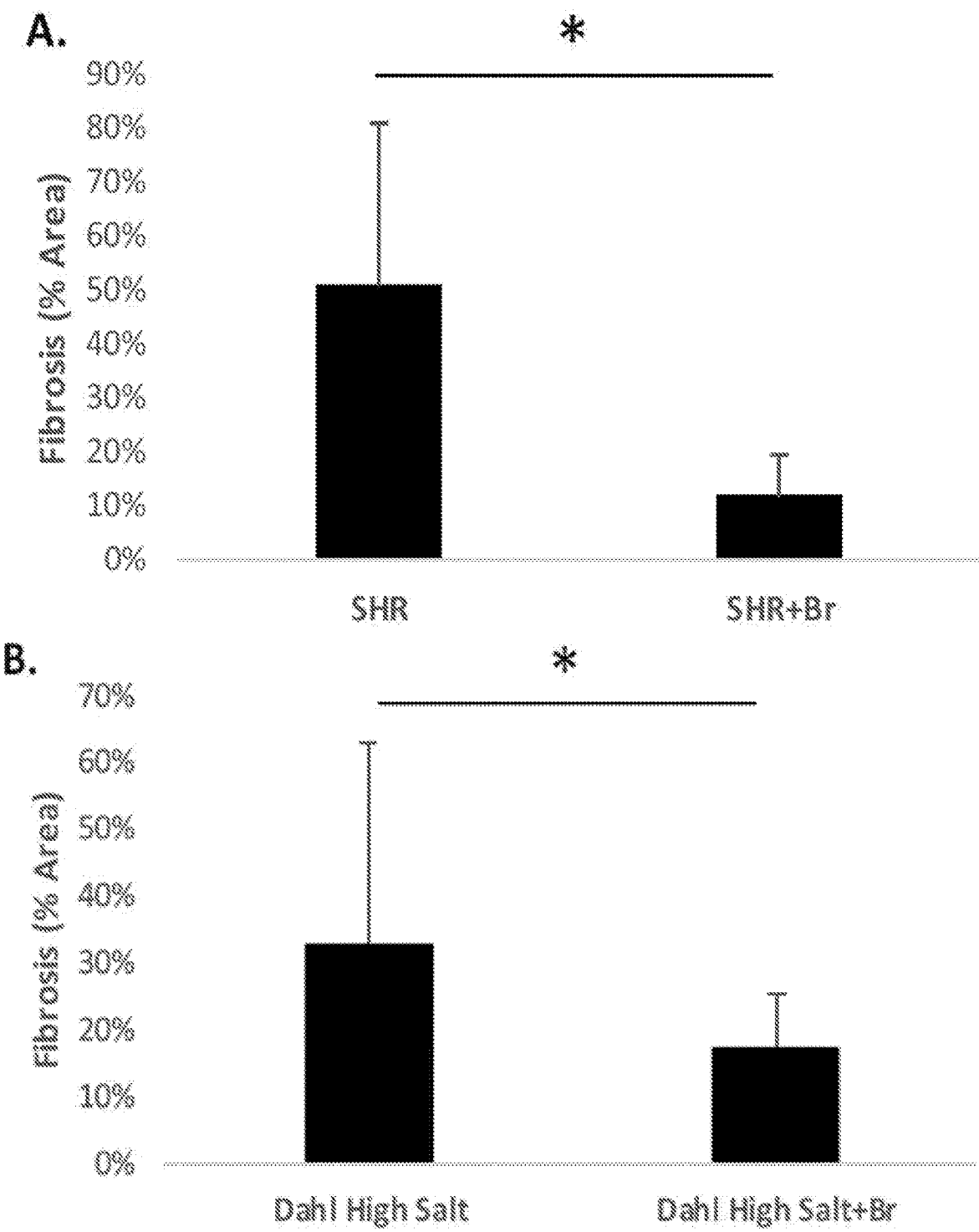
FIG. 4 shows daily Br⁻ administration reduces cardiac interstitial fibrosis staining. (A) Male Spontaneously Hypertensive Rats (SHR) and (B) salt sensitive Dahl rats on a high salt diet (8% NaCl) receiving daily orally-administered Br⁻ for 10 weeks exhibited less cardiac fibrosis compared to age- and sex-matched SHR controls. AIN-76A was base diet for all animals. Br-supplemented diets formulated as 10 mg NaBr per kg AIN-76a (SHR+Br) and 300 mg NaBr per kg AIN-76a+8% NaCl (Dahl High Salt+Br). Fibrosis determined from 5 μm tissue sections stained with Masson's Trichrome. Fibrotic area per high powered field (40×) quantified using an ImageJ macro (Kennedy et al, Hypertension, 2006, 47:488-495) that calculates the percent area where blue staining (collagen) is at least 120% compared to the amount of red staining. Approximately 25-30 images were collected and processed per animal. In total, n=206 images (SHR), 226 images (SHR+Br), 85 images (Dahl High Salt), and 108 images (Dahl High Salt+Br). *p<0.0001, t test.

A central distinguishing feature of the invention is the administration of a therapeutically effective amount of $Br^-$ to a patient. Without wishing to be bound by theory, the inventor has discovered that $Br^-$ is an important active ingredient for therapeutically altering the course of cardiovascular disease and kidney disease (FIGS. 1,4).

Subjects with certain diseases, such as kidney disease and cardiovascular disease, can experience chronically low levels of $Br^-$. Other subjects that are known to possess chronically low $Br^-$ levels include subjects taking diuretic medications, subjects with elevated levels of thiocyanate, subjects with cancer, and subjects receiving intravenous sources of nutrition such as total parenteral nutrition. For example, subjects with end stage renal disease (ESRD) on maintenance dialysis experience treatment-induced loss of $Br^-$, as the dialysis treatment actively removes $Br^-$ from the bloodstream. Without wishing to be bound by theory, the inventor has demonstrated that high salt diet can induce $Br^-$ deficiency in rats. In the clinic, high salt diets are associated with the development of heart disease, and depletion of $Br^-$ may occur in these patients that consume a high salt diet. While certain low $Br^-$ has been recognized in some subjects, such as in ESRD patients on dialysis, the importance of maintaining proper $Br^-$ levels to prevent heart disease and kidney disease has been unrecognized. Consequently, the invention is designed to meet this clinical need for therapeutic compositions and methods that treat cardiovascular disease and/or kidney disease.

When treating dialysis subjects, embodiments of the invention can be administered to subjects before, during, or after a dialysis treatment session in order to administer a therapeutically effective amount of $Br^-$ to these subjects. For example, the administration of compositions to a subject before a dialysis treatment can enable the subject's serum $Br^-$ levels to be elevated at the onset of dialysis, and thereby prevent the subject from becoming Br— deficient after treatment. Alternatively, compositions of the invention can be administered to a subject during a dialysis treatment, in order to offset the immediate transfer of $Br^-$ from the serum to the dialysate. Still yet another option, compositions of the invention can be administered to a subject immediately following dialysis in order to replace serum $Br^-$ that was lost during the dialysis treatment. A physician, veterinarian, or other health care professional could prescribe an appropriate timing of administration for an individual subject.

When treating a subject with a disease, such as but not limited to cardiovascular disease, kidney disease, sepsis, or infection, embodiments of the invention can be administered to the subject at regular intervals. For example, embodiments can be administered to a subject every day, two or more times per week, weekly, multiple times per month, monthly, every other month, quarterly, semi-annually, or annually. Alternatively, embodiments of the invention can be administered to a subject when the results of a diagnostic test, such as measurement of a specific biomarker as discussed herein, indicate that the subject is either in need of a therapeutically effective amount of $Br^-$ or at risk of developing a symptom of disease. As another option, embodiments of the invention can be administered to a subject before, during, or after the subject is administered another drug or undergoes a medical test, surgery, office visit, or other medical procedure. A physician, veterinarian, or other health care professional could prescribe an appropriate timing of administration for an individual subject.

Embodiments as described herein comprise biomarkers for identifying a subject in need of methods and compositions as described herein. An important biomarker for identifying a subject in need of administration of $Br^-$ or Br-comprising compositions is the absolute amount of $Br^-$ in a biological fluid. The biological fluid can be blood, serum, plasma, saliva, sweat, or urine of a subject. Serum $Br^-$ levels below 20 μM imply that the patient is deficient in $Br^-$. In embodiments, only an amount of $Br^-$ or $Br^-$ comprising composition sufficient to raise the circulating levels of $Br^-$ above 2004 is administered to the subject. In other embodiments, the invention comprises compositions comprising an amount of $Br^-$ sufficient to raise the circulating levels of $Br^-$ to an amount between about 20 μM and 1 mM.

In some embodiments, the invention comprises compositions comprising an amount of Br— sufficient to raise the circulating levels of Br— to an amount between 20 μM and 1 mM. In some embodiments, the invention comprises a composition comprising an amount of Br— sufficient to raise the circulating level of Br— to 20 µM, 25 µM, 30 µM, 35 µM, 40 µM, 45 µM, 50 µM, 55 µM, 60 µM, 65 µM, 70 µM, 75 µM, 80 µM, 85 µM, 90 µM, 95 µM, 100 µM, 105 µM, 110 µM, 115 µM, 120 µM, 125 µM, 130 µM, 135 µM, 140 µM, 145 µM, 150 µM, 155 µM, 160 µM, 165 µM, 170 µM, 175 µM, 180 µM, 185 µM, 190 µM, 195 µM, 200 µM, 210 µM, 220 µM, 230 µM, 240 µM, 250 µM, 260 µM, 270 µM, 280 µM, 290 µM, 300 µM, 310 µM, 320 µM, 330 µM, 340 µM, 350 µM, 360 µM, 370 µM, 380 µM, 390 µM, 400 µM, 410 µM, 420 µM, 430 µM, 440 µM, 450 µM, 460 µM, 470 µM, 480 µM, 490 µM, 500 µM, 510 µM, 520 µM, 530 µM, 540 µM, 550 µM, 560 µM, 570 µM, 580 µM, 590 µM, 600 µM, 610 µM, 620 µM, 630 µM, 640 µM, 650 µM, 660 µM, 670 µM, 680 µM, 690 µM, 700 µM, 710 µM, 720 µM, 730 µM, 740 µM, 750 µM, 760 µM, 770 µM, 780 µM, 790 µM, 800 µM, 810 µM, 820 µM, 830 µM, 840 µM, 850 µM, 860 µM, 870 µM, 880 µM, 890 µM, 900 µM, 910 µM, 920 µM, 930 µM, 940 µM, 950 µM, 960 µM, 970 µM, 980 µM, 990 µM, 1 mM, or any other amount between 20 µM and 1 mM.

Preferred serum Br⁻ levels targeted through practice of the invention are amounts between 30 µM and 1 mM Br⁻. In some populations, such as individuals who regularly consume a high salt diet, preferred serum Br⁻ levels are amounts between 100 µM and 500 µM Br⁻ due to the increased renal excretion of Br⁻ in the presence of high salt. In other populations, such as kidney disease patients, preferred serum Br⁻ levels are amounts between 50 µM and 250 µM Br⁻ due to the potentially decreased renal excretion rates of Br⁻. A physician, veterinarian, or other health care professional could determine the preferred target serum Br⁻ levels in a specific subject.

Rather than administer an oral Br-containing vitamin to a patient, which can lead to questions regarding bioavailability and patient compliance, embodiments of the invention comprise administration of Br⁻ and Br-comprising compositions via injection to a subject. Injections as described herein can be administered by a medical professional in a hospital, office, clinic, or in the field. This allows medical oversight of the total amount of Br⁻ administered through the invention, which is an important feature that enables greater control over the serum Br⁻ levels in the patient after treatment with the invention. For example, patient compliance is ensured when the invention is administered by a medical professional. Moreover, the potential issue of bioavailability is negated when the invention is injected into the patient.

In humans, Br⁻ is primarily found in the extracellular space and embodiments of the invention are suitable for elevating the extracellular concentrations of Br⁻ in subjects who are in need thereof. Consequently, the ability of the invention to be injected into a subject provides a rapid means of modulating said extracellular Br⁻ concentrations. Embodiments of the invention can be injected into the bloodstream, skin, tissue, peritoneal cavity, orbital socket, heart, muscle, bone marrow, epidural space, spinal theca, joint, bladder, genitals, or any other organ of a subject. In some embodiments, the invention is injected through a needle into a subject. For example, embodiments can be injected from a syringe into a subject using a needle. In some embodiments, the invention is injected through a tube. For example, the invention can be injected into a subject through a catheter. In some embodiments, the invention is injected through a tube into the blood of a subject. For example, for subjects that are receiving extracorporeal blood purification therapy, such as hemodialysis, embodiments can be injected through a tube into the subject's bloodstream while the blood is outside the body. As another example, some subjects may be administered embodiments through a central line, where the embodiment is stored in a bag with a connected tube that transfers fluid from the bag to the subject. In this case, the tube may inject the embodiment through a connector that allows fluid to be directly injected into a subject's bloodstream. Non-limiting examples of connectors include vascular assess ports, implanted ports, intravenous lines, peripheral intravenous lines, and dialysis assess ports.

Some embodiments of the invention can be isotonic. Other embodiments may be hypotonic. Still other embodiments may be hypertonic. Tonicity of the embodiment may be adjusted with an osmotic agent other than sodium chloride, with non-limiting examples that include dextrose, lactose, and sodium bicarbonate. The tonicity may be controlled during manufacturing of the embodiment. Alternatively, an osmotic diluent may be added to the embodiment in a hospital or pharmacy prior to administration to a subject. Embodiments that are injected into an interstitial tissue, such as intramuscular injection, or eye injection may require the final composition to be isotonic prior to injection. In summary, the invention provides advanced compositions and methods for treating diseases, such as cardiovascular disease, kidney disease, and/or subjects that display low bodily Br⁻ levels. Furthermore, the invention utilizes pharmacologic methods and compositions to administer to a subject therapeutically effective amounts of Br⁻.

Chemical Distinctions

In biology, small differences can yield disproportional effects, such as single point mutations that cause genetic diseases. Similarly, the invention is chemically distinguished by the addition of an effective amount of Br⁻, which is sufficient for achieving the unexpected activity of the invention. In some embodiments, the invention is distinguished by the singular addition of an effective amount of Br⁻. This administration of Br⁻ can be performed in parallel with the administration of other drugs or treatments without impeding this therapeutic activity of Br⁻. Likewise, various salt forms of Br⁻ can be used, with non-limiting examples including sodium bromide, potassium bromide, and magnesium bromide. In fact, any pharmaceutically-acceptable salt of Br⁻ is suitable for manufacture of the invention. In embodiments, compounds that contain a bromine atom as a covalently-bound substituent are not suitable for the invention since they are not salts.

In embodiments, the invention can be manufactured through methods and procedures that are known to one skilled in the art of manufacturing pharmaceutical and/or nutritional compositions. For example, for manufacturing a 1 ml injectable pharmaceutical solution containing 5 mg Br⁻ in prefilled syringe, 6.438 g of NaBr can be dissolved in a total volume of 1 L of water or aqueous solution. Then, 1 ml aliquots can be placed inside a syringe for storage and distribution. The water can be pharmaceutical grade, United States Pharmacopeia (USP) grade, or equivalent. The final solution can be sterilized through terminal sterilization or by the use of aseptic manufacturing methods.

In certain embodiments, the composition comprises bromide and one or more additional compositions. Appropriate amounts of such additional compositions can be added to the solution as desired. Non-limiting examples of additional compositions that can be added to a bromide-containing composition comprise a medical device or drug.

To ensure quality of a composition as described herein, various tests can be performed during the manufacturing. For example, mass spectrometry can be used to determine the amount of Br⁻ in the invention. The element bromine is found as two isotopes with nearly equal proportion in nature, $Br^{79}$ and $Br^{81}$, which assists in identifying $Br^-$ by mass spectrometry. Other non-limiting examples of useful techniques for measuring $Br^-$ include column chromatography, inductively coupled plasma mass spectrometry, x-ray florescence, and neutron activation analysis.

Embodiments of the invention are amenable to many various types of packaging. Non-limiting examples include pre-filled syringes, vials, bottles, aerosol cans, or packets. For example, embodiments of the invention can be administered to a subject via a dropper, a syringe, a needle, a tube, a bag, a can, an aerosol can, a capsule, a vial, or a packet. Embodiments may be packaged as to be amenable certain storage conditions, such as room temperature storage or cold storage, or short term storage or long term storage.

In some embodiments, compositions as described herein are packaged in a format suitable for the convenient administration of the composition to a subject undergoing dialysis treatment. For example, the packaging may contain a connector that allows the invention to be administered through an access port, fistula, graft, or catheter in a dialysis subject. As another example, the packaging may contain a connector that allows the invention to be administered through dialysis tubing, bag, machine, or container. These various packaging formats are within the scope of the invention, being used to administer an effective amount of $Br^-$ to a subject. Embodiments of the invention comprise administering a therapeutically effective amount of $Br^-$ to patients with or at risk of developing cardiovascular disease and/or kidney disease. Bromide is not currently administered to these patients due to a knowledge gap regarding the importance of $Br^-$ in heart and kidney physiology.

Historically, large doses of bromide, such as approximately 0.8-1.6 g $Br^-$ administered every 3-4 hours, were previously used as an early pharmaceutical sedative, anti-libido, and anti-epileptic treatment. Early references, such as the 1920 Handbook of Pharmacy and Therapeutics by Eli Lilly and Co., describe such products comprising high concentrations of bromine. These products relied on the ability of high concentrations of $Br^-$ to suppress neural activity. These high physiological concentrations of $Br^-$ can result in unwanted side effects, including chronic toxicity.

Over time, the historical sedative usage of $Br^-$ was discontinued due the combination of (1) the risk of developing bromism and/or bromoderma and (2) the development of barbiturates and other modern sedatives. Van Leeuwen and Sanger (1987) published a comprehensive review of $Br^-$ toxicity, where the medical usage of $Br^-$ had been largely discontinued by publication of this review. Unfortunately, the historical usage of $Br^-$ salts has mistakenly branded $Br^-$ as a crude sedative treatment.

While $Br^-$ has historically served as an effective sedative, albeit with elevated risk of toxicity, such historical usage qualifies as palliative, non-curative care rather than a disease treatment.

KBr is used as a sedative for refractory pediatric cases of seizures and veterinary treatment of epilepsy (Baird-Heinz, 2012). Additionally, bromide ions are used as counter ions in certain compounds, most of which are used in anesthesiology or pain indications where the drug mechanism of action involves modulating a neurotransmitter receptor. Certain homeopathic drugs also contain bromide for psychological and/or neurologic disorders.

Notably, the anti-epilepsy effect of $Br^-$ occurs when circulating $Br^-$ levels are above approximately 6 mM. In dogs, for example, the reported therapeutic range of serum $Br^-$ levels that are targeted for eliciting a sedative effect is between 12.5 mM and 37.5 mM for subjects beginning treatment with $Br^-$ alone, above 25 mM for dogs that do not response to an initial course of $Br^-$ treatment, and between 12.5 mM-31 mM when $Br^-$ is used in addition to a phenobarbital (Trepanier et al., 1998; Podell et al., 1993). As another example, in humans the targeted therapeutic range to elicit a sedative effect is reported to be between 6 mM-12 mM plasma Br— (Van Leeuwen & Sangster, 1987).

On the other hand, embodiments as described herein comprise administration of low doses of $Br^-$ and Br-comprising compositions to treat kidney disease and heart disease, only targeting serum $Br^-$ levels between about 20 µM and 1 mM after practice of the invention as taught herein. This stands in sharp contrast to the high administered doses of $Br^-$ and the elevated therapeutic range (e.g. >6 mM) targeted in use of $Br^-$ to treat neurological and psychological diseases. For example, the highest serum $Br^-$ concentration achieved through practice of the invention (FIG. 2) was about 40-fold lower than the excessive $Br^-$ concentrations achieved during the previous sedative and toxic administration of $Br^-$. Other non-limiting examples of diseases that can be treated by embodiments of the invention are described herein. In embodiments, the disease to be treated or prevented is not a neurological disease. In embodiments, the disease to be treated or prevented is not a psychological disease. Embodiments apply therapeutically effective amounts of $Br^-$ towards the pharmaceutical treatment and prevention of cardiovascular disease and kidney disease. In some embodiments, therapeutically effective amounts of $Br^-$ comprise low doses of $Br^-$. In embodiments, only an amount of $Br^-$ or Br-comprising composition sufficient to raise the circulating levels of $Br^-$ above 2004 is administered to the subject. In other embodiments, the invention comprises compositions comprising an amount of $Br^-$ sufficient to raise the circulating levels of $Br^-$ to an amount between about 20 µM and 1 mM.

Embodiments of the invention are designed to administer a therapeutic amount of $Br^-$ sufficient to accomplish the desired activity, while at the same time prevent the onset of unwanted side effects and toxicity associated with the overdosing of $Br^-$ to the subject. In humans, $Br^-$ toxicity can develop when serum $Br^-$ levels approach 12 mM or higher while healthy adults typically display about 67 µM plasma Br— levels (Van Leeuwen and Sangster, 1987). Critically, there has not been any understanding of the threshold, with respect to the levels of $Br^-$ in a body fluid, at which the symptoms of Br-deficiency may appear. Moreover, the inventor has shown herein (FIG. 1) that the symptoms of Br-deficiency can develop when serum $Br^-$ levels are below 20 µM. Thus, a serum $Br^-$ concentration of 20 µM appears to approximate an important threshold for inducing Br-deficiency, where subjects who experience serum $Br^-$ levels at or below 20 µM may be at risk of developing a symptom of Br-deficiency. These low levels of $Br^-$ may be achieved in subjects with certain diseases or diets, such as but limited to individuals receiving dialysis treatments or individuals who regularly consume a high salt diet. For such subjects who are Br-deficient or at risk of becoming Br-deficient, the invention can administer therapeutically effective amounts of $Br^-$ to either correct the deficiency or reduce the subject's risk of developing Br-deficiency. For example, some embodiments of the invention can administer only the amount of $Br^-$ or Br— comprising compositions needed to raise a subject's serum $Br^-$ level to about 50 µM. In another example, an embodiment can administer only the amount of $Br^-$ or Br-comprising compositions needed to raise a subject's serum $Br^-$ level to about 100 µM. In still another example, an embodiment can administer only the amount of Br⁻ or Br-comprising compositions needed to raise a subject's serum Br⁻ level to about 250 µM. In yet another example, an embodiment can administer only the amount of Br⁻ or Br-comprising compositions needed to raise a subject's serum Br⁻ level to about 500 µM. In yet another example, an embodiment can administer only the amount of Br⁻ or Br-comprising compositions needed to raise a subject's serum Br⁻ level to about 750 µM. Embodiments can administer only the amount of Br⁻ or Br-comprising compositions needed to raise a subject's serum Br⁻ level to above about 20 µM yet below about 1 mM. Thus, the invention can provide a safe yet effective amount of Br⁻ to a subject.

Extracellular Matrix (ECM) in Cardiovascular Disease and Kidney Disease

Extracellular matrices (ECM) are found throughout tissues and provide essential mechanical and signaling support for tissues. An example of an ECM is the basement membrane (BM). These matrices can exhibit a perturbed structural appearance during disease. For example, structural changes within the vasculature walls can be seen in patients with end-stage renal disease who are at risk of developing cardiovascular disease (Bevc et al., 2006). Embodiments of the invention can be useful in modulating the ECM structure as a mechanism of treating or preventing cardiovascular disease and kidney disease.

Diseases of the Circulatory System, Cardiovascular Disease, and Kidney Disease

Without being bound by theory, there is a significant medical need for new therapeutics that can safely and effectively prevent or treat cardiovascular disease and kidney disease. These are leading causes of global mortality. Heart disease is the leading cause of death in the United States (http://www.cdc.gov/dhdsp/data_statistics/fact_sheets/fs_heart_disease.htm, accessed Aug. 1, 2016), while over 10% of the US population are estimated to have some form of chronic kidney disease (National Chronic Kidney Fact Sheet, 2014, http://www.cdc.gov/diabetes/pubs/pdf/kidney_factsheet.pdf). The invention provides teachings, compositions, and methods to therapeutically prevent and treat cardiovascular disease and kidney disease. As discussed herein, embodiments of the invention address these unmet needs.

Technologically, the invention involves harnessing the ability of bromide ions (Br⁻) to therapeutically treat cardiovascular disease and kidney disease. This represents an advancement over the prior art concerning medical uses of Br⁻, which has been ignored with respect to its therapeutic potential in these two diseases. Consequently, embodiments of the invention are useful for treating various forms of cardiovascular disease and kidney disease, including but not limited to vascular disease, hypertension, heart attack, stroke, thrombosis, coronary artery disease, ischemic heart disease, peripheral artery disease, arterial stiffening, atherosclerosis, heart failure, cardiac remodeling, cardiac fibrosis, vascular wall thickening, dyslipidema, blood clot, anemia, salt-sensitive hypertension, acute kidney injury, chronic kidney disease, end stage renal disease glomerular disease, tubular disease, hyperchlolemia, or an acid-base imbalance.

The circulatory system is responsible for moving blood, nutrients, and gases to and from cells to keep the body in proper balance. The blood vessels transport blood to and from the heart, and the heart pumps oxygenated blood to the body, and the oxygen, gases, and nutrients exchange in the capillaries. Disrupting the integrity of the tubing of the circulatory system can impair the health of the circulatory system, and of the subject. Non-limiting examples of diseases of the circulatory system comprise arteriosclerosis, hypertension, aortic aneurysm, heart disease, varicose veins, chronic venous insufficiency, angina, peripheral vascular disease, or arrhythmia. A central feature of certain embodiments of the invention is the administration of low doses of Br⁻ to a subject with a disease of the circulatory system, a cardiovascular disease, or a kidney disease. For example, embodiments comprise administering to a subject an amount less than 1 mg Br⁻, or between 1 and 250 mg Br⁻ to a subject with a disease of the circulatory system, a cardiovascular disease or a kidney disease. In embodiments, bromide may be administered as a salt (Br⁻) rather than brominated molecule, such as methyl bromide. The cation specie of the Br⁻ salt can be changed to meet the needs of the subject. For example, a subject with heart disease without renal manifestations may be administered KBr in practice of the invention, since potassium is beneficial to heart health while sodium is detrimental to heart health. Alternatively, a subject with end-stage renal disease on maintenance dialysis must diligently monitor their potassium intake, since dialysis is associated with hyperkalemia (elevated potassium levels). As such, practice of the invention in said dialysis patient may administer sodium bromide or magnesium bromide to the patient.

In humans and animals, bromide is nearly exclusively found in the extracellular environment, and has been used as a marker of extracellular volume. Blood Br⁻ levels appear to be tightly regulated by the kidneys, with average concentration of 65-70 µM in reportedly healthy adults (van Leeuwen and Sangster, 1987). Renal excretion of Br⁻ is tied to the excretion rates of sodium and/or salt. Thus, increased salt consumption can lead to depletion of Br⁻ from a subject. Low Br⁻ levels can predispose a subject to developing cardiovascular disease and/or kidney disease. Embodiments of the invention can be used to correct low Br⁻ levels in a subject as a means of preventing or treating cardiovascular disease and kidney disease. Other embodiments of the invention can be used to diagnose someone who is at risk of developing cardiovascular disease or kidney disease by measuring Br⁻ levels in a sample from a subject, such as serum Br⁻ levels, comparing the levels to that of a control sample, determining whether the Br⁻ level is below a threshold, such as 20 µM serum Br⁻, and administering a therapeutically effective amount of Br⁻ to a subject when the Br⁻ level is below said threshold.

Br⁻ levels have been shown to be altered in some patient populations, such as in subjects undergoing dialysis. There, dialysate fluids actively remove Br⁻ from the patient's bloodstream during the dialysis treatment due to low concentrations of Br⁻ in the dialysate (Miura et al., 2004). It was previously speculated that low Br⁻ levels in dialysis patients can cause insomnia (Canavese et al., 2006), owing to the identification of a sleep-inducing brominated compound in cerebral spinal fluid (Yamane et al., 1984; Yanagisawa and Torii, 2002).

Figure 3:
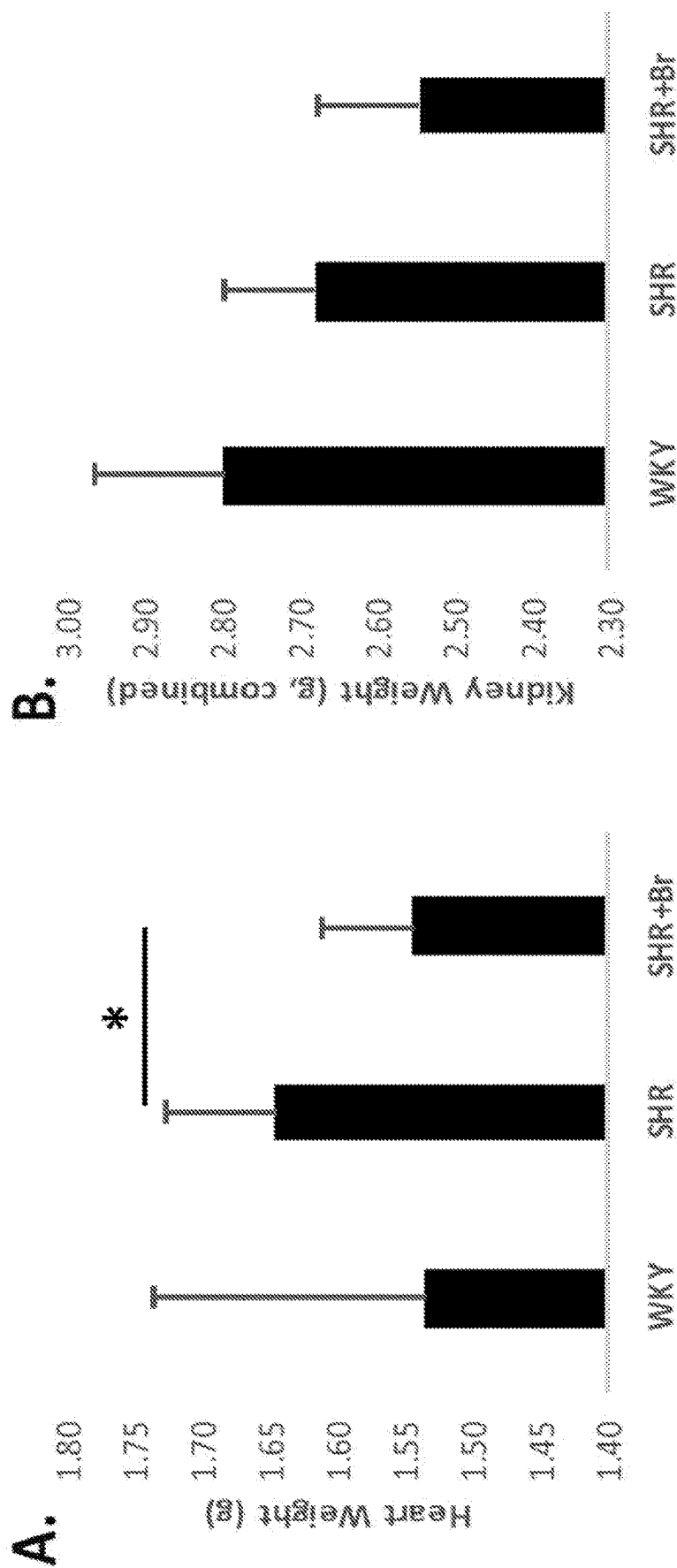
FIG. 3 shows daily $Br^-$ administration in 10 week preclinical study using SHR disease model. (A-B) Heart and kidney weights from 10 week repeat dosing study in SHR model. $Br^-$ administered daily via diet, with AIN-76a as base diet. WKY served as genetic control. Both kidneys per animal weighed together. Statistically significant reduction in heart weight noted in SHR receiving $Br^-$ compared to SHR on AIN-76a alone. *:p<0.05, T-test. (C-D) Heart and kidney weights from panels A-B normalized to body weight. Trends observed in absolute weights are preserved in normalized organ weights. (E) Rats were administered a diet of AIN76A with or without 10 mg NaBr per kg feed ("SHR" and "SHR+Br" study arms, respectively). Survival probability was calculated between SHR rats receiving dietary Br⁻ and SHR rats receiving AIN76A control diet over a 10 week study period. As a second control, Wistar Kyoto (WKY) rats were fed AIN76A control diet over the same period. 8 rats per study arm. One SHR control rat died during a surgical procedure. However, no statistical difference in survival was detected among the groups. (F) After one day on study diet, Br⁻ administered rats displayed significantly reduced urinary microprotein/creatinine ratio.

Clinically, when levels of Br⁻ in a subject are at or near the levels seen in healthy adults, Br⁻ likely fulfils a required structural activity within the extracellular matrices of human tissues. Conversely, Br⁻ is not able to satisfy its structural activity when levels in a subject are below normal, and the risk of developing cardiovascular disease and kidney disease stem from these structural deficiencies occurring at a molecular level within tissues. Owing to the near-ubiquitous distribution of collagen IV in organisms, aspects of the invention can be used to treat vascular disease, hypertension, heart attack, stroke, thrombosis, coronary artery disease, ischemic heart disease, peripheral artery disease, arterial stiffening, atherosclerosis, heart failure, cardiac remodeling, cardiac fibrosis, vascular wall thickening, dyslipidema, blood clot, anemia, salt-sensitive hypertension, acute kidney injury, chronic kidney disease, end stage renal disease glomerular disease, tubular disease, hyperchlolemia, or an acid-base imbalance. Mechanistically, all of these diseases are unified, at a tissue level, by their reliance on the activity of $Br^-$. Moreover, $Br^-$ likely fulfils an important extracellular function in animals, enabling the disclosed invention to be useful in preventing and treating cardiovascular disease and kidney disease in humans as well as animals, such as dogs, cats, and rodents. For example, the invention has been successfully used to treat heart and kidney disease in rats (FIGS. 1,3).

Embodiments of the invention can use many different means to detect or measure $Br^-$ in a subject. Non-limiting examples of means to detect or measure $Br^-$ in a subject include column chromatography, inductively coupled plasma mass spectrometry, x-ray florescence, and neutron activation analysis. Such tools can be utilized in embodiments of the invention. Each technique offers various advantages and disadvantages, such as cost, detection limits, and the amount of sample required. For example, mass spectrometry and column chromatography can be used in methods as described herein for quantifying the levels of bromide from patient samples, including blood and urine samples. Preferred embodiments of the invention utilize inductively coupled mass spectrometry for measuring urinary $Br^-$ as well as column chromatography for measuring $Br^-$ in blood. Mass spectrometry offers a lower detection limit than column chromatography, allowing a clinician to more accurately measure $Br^-$ in a patient who may be deficient in $Br^-$.

Clinical tests for measuring $Br^-$ in patient samples were developed in response to the widespread yet mistaken belief that $Br^-$ is inherently unsafe in humans. Consequently, many of the methods are designed to detect Br-toxicity rather than Br-deficiency. Nonetheless, the existence of these methods better enables the practice of the invention by providing readily-available diagnostic methods for measuring $Br^-$ in patient samples. As stated above, mass spectrometry provides suitable sensitivity for detecting low levels of $Br^-$ in patient samples.

Large doses of bromide, such as approximately 0.8-1.6 g $Br^-$ administered every 3-4 hours, were previously used as an early pharmaceutical sedative, anti-libido, and anti-epileptic treatment. Historical references, such as the 1920 Handbook of Pharmacy and Therapeutics by Eli Lilly and Co., describe such products comprising high concentrations of bromine. Unlike embodiments of the invention, these products relied on the ability of high concentrations of $Br^-$ to suppress neural activity. As described herein, high physiological concentrations of $Br^-$ can result in unwanted side effects, including chronic toxicity. Importantly, these sedative and toxic $Br^-$ concentrations approximately 10-fold higher than the highest demonstrated in vivo $Br^-$ level achieved through practicing embodiments of the invention. Furthermore, the invention is neither designed for treating neurologic symptoms nor acts through neurologic-based mechanisms. The invention was developed as a therapeutic strategy to prevent or treat cardiovascular disease or kidney disease, without treating or preventing forms of neurologic disease. The invention relies on new medical understanding of $Br^-$, which enables the compositions and methods disclosed here that are entirely distinct from the historical use of $Br^-$ as a sedative and palliative treatment.

The ability of $Br^-$ to effectively modulate neural activity is only known to occur when the systemic concentrations of $Br^-$ are greatly elevated above their normal concentrations. Furthermore, the high target concentrations for achieving a sedative effect are close to those concentrations where $Br^-$ causes unwanted side effects in patients. Indeed, when used for these early sedative purposes, therapeutic concentrations were often 6 mM and higher, while side effects can occur over 12 mM (van Leeuwen and Sangster, 1987). Chronic toxicity occurs above this higher threshold, manifesting as a set of neurologic and/or dermatologic symptoms termed bromism and bromoderma, respectively. With respect to the invention, these elevated levels of $Br^-$ are far beyond (1) the normal $Br^-$ concentrations seen in healthy adults, (2) the $Br^-$ concentrations found in the compositions and methods disclosed here, and (3) the final $Br^-$ concentrations to be circulating in patients after treatment with the invention. For example, embodiments of the invention, when practiced on a patient receiving maintenance dialysis, may be designed to therapeutically raise the serum $Br^-$ concentration to between 50-100 μM. This concentration range is 60-120× lower than the neurologic activity threshold of 6 mM.

Historically, administering high doses of bromide was indeed an effective sedative treatment. Over time, however, this medical usage was discontinued due the combination of (1) the risk of developing bromism and/or bromoderma and (2) the development of barbiturates and other modern sedatives. Van Leeuwen and Sanger (1987) published a comprehensive review of $Br^-$ toxicity, where the medical usage of $Br^-$ had been largely discontinued by publication of this review. Unfortunately, the historical usage of $Br^-$ salts has mistakenly branded $Br^-$ as a crude sedative treatment.

While $Br^-$ has historically served as an effective sedative, albeit with elevated risk of toxicity, such historical usage qualifies as palliative, non-curative care rather than a disease treatment. In contrast, embodiments of the invention are suitable for therapeutic use with curative intent in treating or preventing cardiovascular disease or kidney disease.

Currently, KBr is only used as a sedative for refractory pediatric cases of seizures and in canine epilepsy (Baird-Heinz, 2012). Significantly, the anti-epilepsy effect of $Br^-$ occurs when serum $Br^-$ levels are approximately 6-12 mM, which is far above the in vivo $Br^-$ levels that are targeted during practice of the invention. Additionally, bromide ions are occasionally used as counter ions in modern pharmaceutical treatments. Most of these current pharmaceutical formulations of $Br^-$ are used in anesthesiology or pain indications, where the mechanism of action involves modulating a neurotransmitter receptor. Importantly, none of these drugs are used to treat or prevent cardiovascular disease or kidney disease. Certain homeopathic drugs also contain bromide for psychological and/or neurologic disorders.

Notably, all of the current medical uses of $Br^-$ fall outside the scope of the symptoms which the invention is useful in treating. Furthermore, they demonstrate that, outside this invention, the ability to harness the therapeutic potential of $Br^-$ has not progressed beyond the historical neurologic indications.

Cardiovascular Disease and Kidney Disease

There is much evidence that cardiovascular disease and kidney disease are related. Patients with kidney disease have an elevated risk of developing various forms of cardiovascular disease. Conversely, for example, hypertension sure is a leading cause of kidney failure. Fundamentally, the heart and kidneys are both physically connected by the vasculature and both functionally interact with the bloodstream, where the heart pumps blood while the kidneys filter blood.

This close relationship provides rationale for the observed clinical relationship between cardiovascular disease and kidney disease.

With respect to the invention, an additional commonality is that both types of disease impact tissues that rely strongly on collagen IV, a potential site of $Br^-$ activity in mammals. In the vasculature, collagen IV scaffolds underlie endothelial cells and surround smooth muscle cells. Moreover, collagen IV is found throughout heart tissue. In kidneys, collagen IV is central to glomerular architecture and function, evidenced in Goodpasture's Disease and Alport's Syndrome where disruption of collagen IV is a causal disease factor (Hudson et al., 2003), and is also present elsewhere in kidneys including the tubules. Moreover, collagen IV is located within the vascular wall, which is where vascular thickening can occur during cardiovascular disease or kidney disease. By modulating the structure of collagen IV, the invention is thus capable of therapeutically acting on a pathogenic mechanism of cardiovascular disease or kidney disease.

A particular benefit of the invention is that it uses a single effective agent, $Br^-$, to act on either cardiovascular disease or kidney disease. Examples of specific conditions that the invention can be useful for treating include but are not limited to vascular disease, hypertension, heart attack, stroke, thrombosis, coronary artery disease, ischemic heart disease, peripheral artery disease, arterial stiffening, atherosclerosis, heart failure, cardiac remodeling, cardiac fibrosis, vascular wall thickening, dyslipidema, blood clot, anemia, salt-sensitive hypertension, acute kidney injury, chronic kidney disease, end stage renal disease glomerular disease, tubular disease, hyperchlolemia, or an acid-base imbalance.

Elevated dietary salt (e.g. NaCl, sodium chloride) intake is associated with many different diseases, including the classes of diseases described herein. As a result, patients with these diseases or at risk of these diseases are often advised to consume a low-sodium or low-salt diet. Based on the data described in FIG. 1, the invention provides an unexpected advance to this long-held medical wisdom about the health dangers of too much salt. Specifically, embodiments of the invention use $Br^-$ ions to reduce the medical risks that are known to be associated with a high-salt or high-sodium diet. Importantly, this effect of $Br^-$ can be accomplished while the subject continues to consume a high-salt diet. For example, in one embodiment of the invention, a therapeutically effective amount of $Br^-$ is be administered to a patient with salt-sensitive hypertension who regularly consumes a high sodium diet. In this case, practice of the invention could therapeutically mitigate some of the health risks that stem from the patient's unhealthy diet without actually requiring any changes to the diet. While it would of course be desirable for said patient to adopt a low salt diet, it can be challenging for patients with cardiovascular or kidney disease to successfully modify their diet. With this in mind, the ability of $Br^-$ to treat disease in the presence of a high salt diet enables the invention to work even when patients do not adopt healthy dietary modifications.

In rats, the excretion rate of $Br^-$ has been shown to be dependent on sodium $Na^+$ excretion (Pavelka et al., 2005). Moreover, it is widely known that $Na^+$ excretion rates are enhanced when excess $Na^+$ is consumed. Thus, rats that consume elevated amounts of $Na^+$ will begin excreting greater amounts of $Na^+$ and $Br^-$, resulting in a lowering of circulating levels of $Na^+$ and $Br^-$. In humans, excess consumption of NaCl will cause circulating $Br^-$ levels to fall. Thus, consumption of a high-salt diet can deplete a subject of adequate circulating $Br^-$. There is an observed clinical association between elevated sodium consumption and risk of developing hypertension, vascular disease, other forms of cardiovascular disease, chronic kidney disease, and other forms kidney disease. Embodiments of the invention can be used to treat or prevent these diseases, where the invention acts to maintain a desirable amount of $Br^-$ within the bloodstream of a treated subject.

An aspect of the invention is that there is a certain minimal threshold amount of bromide that is required in order to prevent symptoms of Br-deficiency. This threshold has been determined by the inventor to be approximately 20 µM serum $Br^-$ concentration. This threshold can be reached via (1) malnutrition; (2) certain medical treatments, such as dialysis; (3) certain drugs, such as diuretics or cancer chemotherapies; (4) dietary $Na^+$ consumption above 2300 mg per day; (5) dietary consumption is above 3545 mg per day. Subjects with one or more of these features may be treated with embodiments of the invention.

Certain drugs are known to cause damage to a patient's cardiovascular system and/or kidneys. Additionally, some drugs can cause these side effects as well as lower the serum $Br^-$ concentration in a patient, including but not limited to diuretic agents and cancer chemotherapeutic agent. Embodiments of the invention can be administered in combination with a diuretic agent or cancer chemotherapeutic agent. In other embodiments, the invention can be administered to a subject in order counteract, reverse, or otherwise improve the side effect profile of a diuretic agent or cancer chemotherapeutic agent. In still other embodiments, the invention can be administered to a subject in order to counteract, reverse, or otherwise improve the cardiovascular and/or renal side effects of a drug.

The following is provided as an example of the potential pathologic mechanisms induced by low $Br^-$ levels and how they can present in a clinical setting. Such mechanisms can be treated or prevented by embodiments of the invention.

Hypertension, cardiovascular and vascular diseases disease are associated with high dietary salt consumption. Mechanistically, a high salt diet can deplete a subject of $Br^-$ in the patient. At a molecular level, $Br^-$ acts on the collagen IV scaffolds that are found throughout vascular and heart tissue. Patients who regularly consume a high-salt diet can maintain chronically low $Br^-$ levels, a form of malnutrition induced by a high-salt diet, which can result in a reduction of sulfilimine crosslinking in the collagen IV scaffolds in the heart and vasculature. This can predispose such tissues to thickening of collagen IV scaffolds, enlargement of myocytes, and extracellular remodeling (eg. cardiac fibrosis) events that collectively reduce the ability of these tissues to function properly. From a clinical perspective, these molecular, cellular, and tissue responses can coalesce into the symptoms of hypertension, cardiovascular and vascular diseases. For such patients, embodiments of the invention can be used to restore desirable levels of $Br^-$ in the bloodstream of said patients in order to prevent or treat cardiovascular disease.

Embodiments of the invention can also be used to treat or prevent kidney disease. In support of this, it has been reported that high urinary $Na^+$ levels are associated with increased risk of disease progression in patients with chronic kidney disease (He et al., 2015). In healthy adults, urinary $Na^+$ levels are influenced in part by $Na^+$ consumption, where a high-salt diet leads to elevated blood pressure, which causes kidneys to excrete more $Na^+$ in effort to lower blood pressure. As such, the results of this study can be interpreted as further evidence that chronic kidney disease patients on a high-salt diet have poor long-term outcomes. Alternatively, considering that the patients had unhealthy kidneys, sodium dysregulation can be considered. In this case, a patient's kidneys can be unable to properly regulate $Na^+$ resulting in elevated $Na^+$ excretion rates even while consuming a normal-salt or low-salt diet. Simultaneous measurements of blood and urinary $Na^+$ can provide a strategy for determining whether the fundamental problem was dietary or renal.

With respect to $Br^-$, since $Br^-$ excretion is tied to salt excretion, it stands to reason that elevated $Br^-$ excretion rates may be an undesirable prognostic indicator in chronic kidney disease patients. Regardless of whether the enhanced salt excretion (and therefore $Br^-$ excretion) is caused by dietary or renal factors, such a patient can simultaneously experience Br-deficiency. As a result, administering supplemental $Br^-$, such as administering embodiments of the invention, to such patients can correct the deficiency and lower the long-term risk profile.

For patients treated with maintenance dialysis, dialysis fluids contain lower amounts of $Br^-$ than is found in a patient's bloodstream, causing bloodstream $Br^-$ to transfer to the dialysis fluid (from high to low concentrations) during the dialysis treatment and effectively removing dietary-derived $Br^-$ from the patient. Thus, dialysis patients are exposed to chronically low $Br^-$ levels. Such patients are at high risk of developing cardiovascular disease, anemia, stroke, peripheral artery disease, and other co-morbidities. Embodiment of the invention can be used to treat or prevent these diseases and pathogenic mechanisms that are associated with dialysis. For example, in order to preventively address the risk that a patient on maintenance dialysis will develop cardiovascular disease, said patient may be administered a therapeutic dose of $Br^-$. Said dose may comprise 100 mg of $Br^-$. Said dose may comprise any amount between 1 and 250 mg $Br^-$.

These disease mechanisms apply to human as well as animal health, and specifically mammalian animals. Similar to humans, the pathologic effects of low $Br^-$ can be experienced by dogs, cats, cattle, and other mammalian animals. For example, cats are prone to develop heart disease, specifically feline hypertrophic cardiomyopathy, that can be treated with embodiments of the invention. Moreover, dogs are prone to kidney disease, specifically canine chronic kidney disease, that can be treated with embodiments of the invention. In animals, low $Br^-$ levels is a putative cause of disease in animals, acting through a collagen IV-based mechanism to cause disease. Embodiments of the invention can be useful in preventing, treating, or otherwise addressing cardiovascular disease or kidney disease in mammalian animals.

Collagen IV biosynthesis requires ascorbic acid (vitamin C), and as such, individuals with combined deficiency of vitamin C and $Br^-$, or at least chronically low levels of both, can exhibit widespread defects in their tissues. For such an individual, the invention can be combined with effectively administering an appropriate amount of vitamin C. Since orally administered vitamin C is poorly adsorbed in humans, a large amount can need to be administered orally or the vitamin C can need to be administered intravenously or through another appropriate route.

Br-deficiency can occur in combination with magnesium ($Mg^{2+}$) deficiency. Dialysis patients can be susceptible to this combination deficiency, owing to the nutritional imbalances created by dialysis treatments. Mg-deficiency is associated with increased risk of mortality, both cardiovascular and non-cardiovascular, in dialysis patients (Sakaguchi et al., 2013). Patients with serum $Mg^{2+}$ levels between 2.5 and 3.0 mg/dl have shown the lowest risk of developing cardiovascular disease (Sakaguchi et al., 2013). In some patients with hyperphosphatemia, low $Mg^{2+}$ levels can promote risk of calcification, including vascular calcification (Sakaguchi et al., 2014). The occurrence of low $Br^-$ and Mg-deficiency in the same patient, such as a dialysis patient, can further elevate the patient's risk of mortality, cardiovascular disease, or vascular calcification.

Anemia is a symptom of iron deficiency and can also occur in subjects who are in need of $Br^-$ administration through practice of the invention. For example, dialysis can lower the $Br^-$ levels in a patient as well as increase risk of developing anemia. Embodiments of the invention can be combined with iron supplementation, administration, and/or monitoring in order to prevent and treat anemia.

B vitamins are import for kidney and heart health as well as numerous cellular and metabolic functions. This vitamin class is comprised of many different chemical species, including thiamine, riboflavin, niacin, pantothenic acid, pyridoxine, pyridoxal, pyridoxamine, biotin, folic acid, and cobalamin. Thus, embodiments of the invention can be combined with administration of one or more B vitamins, or B vitamin derivatives, in order to prevent and/or treat any heart disease, kidney disease, or the effects of B vitamin deficiency.

Biomarkers of Cardiovascular Disease and Kidney Disease

Embodiments of the invention can be used to identify a subject who would benefit from administration of an amount of $Br^-$ or Br-comprising composition sufficient to maintain the serum $Br^-$ level to an amount between about 20 μM and about 1 mM, for example between about 50 μM and about 1 mM. In some embodiments, said subject displays one or more of the following: systolic blood pressure that displays a clinically meaningful difference compared to baseline levels, healthy levels, normal levels, or medically acceptable systolic blood pressure reference values; diastolic blood pressure that displays clinically meaningful difference compared to baseline levels, healthy levels, normal levels, or medically acceptable diastolic blood pressure reference values; heart rate that displays a clinically meaningful difference compared to baseline levels, healthy levels, normal levels, or medically acceptable heart rate reference values; cardiac fibrosis; salt sensitive hypertension; glomerular filtration rate less than 60 ml/min/1.73 m2; urine albumin levels that display a clinically meaningful elevation over baseline levels, healthy levels, normal levels, or medically acceptable reference values; serum levels of BNP, ANP, or pro-BNP that display a clinically meaningful difference compared to baseline levels, healthy levels, normal levels, or medically acceptable reference values; or urinary or plasma cyclic guanosine monophosphate (cGMP) levels that display a clinically meaningful difference compared to baseline levels, healthy levels, normal levels, or medically acceptable reference values.

Hypertension is a well-known cause of many forms of cardiovascular and kidney diseases, including but not limited to heart attack, heart failure, atherosclerosis, chronic kidney disease, and end stage renal disease. For patients presenting with elevated blood pressure, a key clinical objective is achieving sustained reduction of blood pressure through lifestyle modifications, dietary modifications, and/or the prescription of hypertensive medications. Non-limiting examples of lifestyle and dietary modifications include adopting a daily exercise routine; avoiding caffeine; avoiding alcohol; and increasing dietary intake of fiber, nuts, and fresh fruits and vegetables. Non-limiting examples of hypertensive medications include thiazide diuretics, potassium sparing diuretics, loop diuretics, angiotensin converting enzyme inhibitors, angiotensin receptor blockers, β-blockers, vasodilators, calcium channel blockers, α-blockers, renin inhibitors, aldosterone antagonists, alpha2-agonists, and adrenergic agents. Embodiments of the invention can be used as food items or medical foods that may assist in controlling a subject's blood pressure. Other embodiments of the invention can be used as hypertensive medications that therapeutically maintain reduced blood pressure levels in a subject. Embodiments of the invention can be used in isolation or in combination with lifestyle modifications, dietary modifications, and/or other hypertensive medications.

The American Heart Association (AHA) recommends that normal blood pressure values comprise a systolic blood pressure below 120 mm Hg and a diastolic blood pressure below 80 mm Hg. The AHA defines prehypertension as either a systolic blood pressure between 120-139 mm Hg or a diastolic blood pressure between 80 and 89 mm Hg. Further, the AHA defines Stage 1 Hypertension as either a systolic blood pressure between 140-159 mm Hg or a diastolic blood pressure between 90 and 99 mm Hg. The AHA defines Stage 2 Hypertension as either a systolic blood pressure of at least 160 mm Hg or a diastolic blood pressure of at least 100 mm Hg. Finally, the AHA defines a hypertensive emergency as either a systolic blood pressure of above 180 mm Hg or a diastolic blood pressure of above 110 mm Hg (http://www.heart.org/HEARTORG/Conditions/HighBloodPressure/KnowYourNumbers/Understanding-Blood-Pressure-Readings_UCM_301764_Article.jsp). These numbers are reference values to be used by a medical professional, such a nurse, doctor, physician, or physician assistant, in the clinical evaluation of a subject. For example, a doctor, physician, physician assistant, or other qualified medical professional may determine that a patient has stage 1 hypertension if the patient displays a systolic blood pressure of 145 mm Hg and a diastolic blood pressure of 95 mm Hg. As another example, a subject may be at risk of developing hypertension if the subject's blood pressure rises from 110 over 75 (systolic over diastolic) mm Hg to 140 over 90 mm Hg over a 3 month period and the subject's blood pressure is continuously elevated for the next 3 months. Embodiments of the invention can be used to lower blood pressure in a subject.

Importantly, embodiments of the invention only use small amounts of Br⁻ to achieve significant reductions in blood pressure. Specifically, embodiments of the invention only administer an amount of Br⁻ or Br-comprising composition sufficient to maintain the serum Br⁻ level to an amount between about 50 µM and about 1 mM in the subject. This distinguishes embodiments of the invention from the historical pharmacologic administration of Br⁻ that suggested large doses of Br⁻ are capable of lowering arterial blood pressure (Addison, *Can. Med. Assoc. J.,* 18(3): 281-285, 1928). The historical reference used excessive amounts Br⁻ to achieve the reported reduction in blood pressure, thereby placing the patient at risk of developing a Br-related toxicity. As a result, the therapeutic potential of Br⁻ as a blood pressure treatment has been ignored. Embodiments of the invention enable Br⁻ to be safely administered as a blood pressure lowering treatment to a subject, overcoming the toxicity risks that limited prior pharmacologic use of Br⁻.

Embodiments of the invention may reduce blood pressure in a subject by triggering slowing of the subject's heart rate. Elevated peripheral heart rate is associated with hypertension and the development of cardiovascular disease (Reule & Drawz, *Curr. Hypertens. Rep.* 2012). The AHA recommends an average resting heart rate of between 60-100 beats per minute for individuals age 10 years old and older (http://www.heart.org/HEARTORG/HealthyLiving/PhysicalActivity/FitnessBasics/Target-Heart-Rates_UCM_434341_Article.jsp). However, while heart rate is routinely monitored in various emergency medicine, clinical, and hospital settings, heart rate reducing medications are not associated with reducing adverse events in hypertensive patients. In contrast, embodiments of the invention can reduce adverse events in a hypertensive subject as demonstrated by the reduced morbidity experienced by salt sensitive Dahl rats receiving Br⁻ administration (FIG. 1).

Kidney function is commonly assessed using the glomerular filtration rate (GFR). Moreover, the staging of kidney disease is determined by the GFR of a patient where, in broad terms, a GFR between 120 to 60 is normal, a GFR between 60 and 15 represents kidney disease, while a GFR below 15 represents kidney failure. More specifically, stage 1 chronic kidney disease (CKD) can be defined as a GFR of 90 or above, stage 2 CKD can be defined as a GFR between 89-60, stage 3a CKD can be defined as a GFR between 59-44, stage 3b CKD can be defined as a GFR between 44-30, stage 4 CKD can be defined as a GFR between 29-15, and stage 5 CKD ("kidney failure") can be defined as a GFR below 15 (https://www.kidney.org/atoz/content/gfr). Subjects with kidney disease, as determined by a GFR of 60 or below, have an increased risk of cardiovascular disease. Conversely, subjects with cardiovascular disease, such as but not limited to hypertension, are at increased risk of developing kidney disease that is evidenced by a decline in their GFR. Embodiments of the invention can be administered to a subject with a GFR of 60 or below. Some embodiments of the invention can be administered to a subject with a GFR of 60 or above and who are at risk of developing kidney disease such as individuals with diabetes, existing cardiovascular disease, hypertension, a family history of kidney disease, or who display concurrent albuminuria.

The presence of albumin in urine can indicate a decline in kidney function. Within the tubules of healthy kidneys, most of the albumin that is filtered through the glomerulus is actively removed from filtrate. As a result, the presence of albumin in urine can indicate pathologic disruption of either glomerular or tubular activity. Urinary albumin levels are often expressed as the ratio of albumin to creatinine in urine, where a normal or healthy ratio is 30 mg albumin per gram of creatinine (30 mg/g). A ratio between 30-299 mg/g can represent moderately increased albuminuria. A ratio above 300 mg/g can represent severely increased albuminuria.

Natriuretic peptide (NP) signaling is involved with cardiovascular and renal diseases. Elevated serum levels of brain natriuretic peptide (BNP) can be a diagnostic marker of acute decompensated heart failure. In patients with acute dyspnea, BNP levels over 400 pg/ml indicate heart failure, levels below 100 pg/ml indicating heart failure is unlikely, and levels between 100-400 pg/ml require the clinical judgement of the attending physician or doctor in order to be correctly diagnosed as heart failure. Additional diagnostic value can be found in the N-terminal of proBNP (NT-proBNP), which is precursor protein of BNP. In patients younger than 50 years of age with acute dyspnea, NT-proBNP levels over 450 pg/ml are indicative of heart failure. In patients between 50 and 75 years with acute dyspnea, NT-proBNP levels over 900 are indicative of heart failure. In patients older than 75 years with acute dyspnea, NT-proBNP levels over 1800 are indicative of heart failure. Moreover, elevated levels of BNP and atrial natriuretic peptide (ANP)

can be seen in patients with chronic kidney disease. Healthy individuals can display blood ANP levels between 22-77 pg/ml. In embodiments, blood levels of natriuretic peptides, such as ANP and BNP can indicate the need for administration of Br-compositions as described herein, where BNP levels below about 50 pg/ml or above 100 pg/ml or where ANP levels above about 77 pg/ml or below about 22 pg/ml can indicate need for administration of a Br-composition as described herein. In some embodiments, BNP levels below about 40 pg/ml, or below about 30 pg/ml, or even below about 20 pg/ml, or even still below about 10 pg/ml can indicate need for administration of a Br-composition as described herein. In some embodiments, BNP levels above about 100 pg/ml, or above about 200 pg/ml, or above about 300 pg/ml, or above about 400 pg/ml, or above about 500 pg/ml, or above about 600 pg/ml, or above about 700 pg/ml, or above about 800 pg/ml, or above about 900 pg/ml, or above about 1000 pg/ml, or above about 1100 pg/ml, or above about 1200 pg/ml, or above about 1300 pg/ml, or above about 1400 pg/ml, or above about 1500 pg/ml, or above about 1600 pg/ml, or above about 1700 pg/ml, or above about 1800 pg/ml, or above about 1900 pg/ml, or above about 2000 pg/ml can indicate need for administration of a Br-composition as described herein. In some embodiments, ANP levels below about 20 pg/ml, or below about 15 pg/ml, or below about 10 pg/ml, or even below about 5 pg/ml, or even below about 1 pg/ml, or even still undetectable amounts of ANP can indicate need for administration of a Br-composition as described herein. In some embodiments, ANP levels above about 77 pg/ml, above about 80 pg/ml, above about 90 pg/ml, above about 100 pg/ml, above about 110 pg/ml, above about 120 pg/ml, above about 130 pg/ml, above about 140 pg/ml, above about 150 pg/ml, above about 160 pg/ml, above about 170 pg/ml, above about 180 pg/ml, above about 190 pg/ml, above about 200 pg/ml, above about 210 pg/ml, above about 220 pg/ml, above about 230 pg/ml, above about 240 pg/ml, above about 250 pg/ml, above about 260 pg/ml, above about 270 pg/ml, above about 280 above about 290 pg/ml, or even above about 300 can indicate need for administration of a Br-composition as described herein.

Without being bound by theory, NP's can be therapeutic, for example, certain recombinant forms of ANP and BNP have been developed as drugs such as carperitide (recombinant ANP) and nesiritide (recombinant BNP). However, the clinical performance of these NP-derived pharmaceuticals has not matched their hypothesized potential. For example, carperitide administration is associated with increased in-hospital mortality in acute heart failure patients in Japan (Matsue et al., *J. Card. Fail.*, 21(11):859-864, 2015). As another example, nesiritide administration has been associated with worsening renal function and increased mortality in patients with acute decompensated heart failure (Sackner-Bernstein et al., *Circulation*, 111(12):1487-1491, 2005; Sackner-Berstein et al., *JAMA*, 293(15):1900-1905, 2005). Without being bound by theory, the field of heart failure has been long plagued by therapeutics that improve one or more biomarkers of disease, or surrogate end points, while not significantly improving long-term clinical outcomes such as survival or hospitalization rates. As discussed herein, Br$^-$ is an important component of NP signaling (FIGS. 5-6), and Br-serves along with ANP as well as BNP as improved biomarkers of disease as well as clinical outcomes. Specifically, embodiments of the invention can modulate NP expression, reduce blood pressure, reduce cardiac fibrosis, and increase survival by way of regulating Br— levels (FIGS. 1,4-6).

Figure 5:
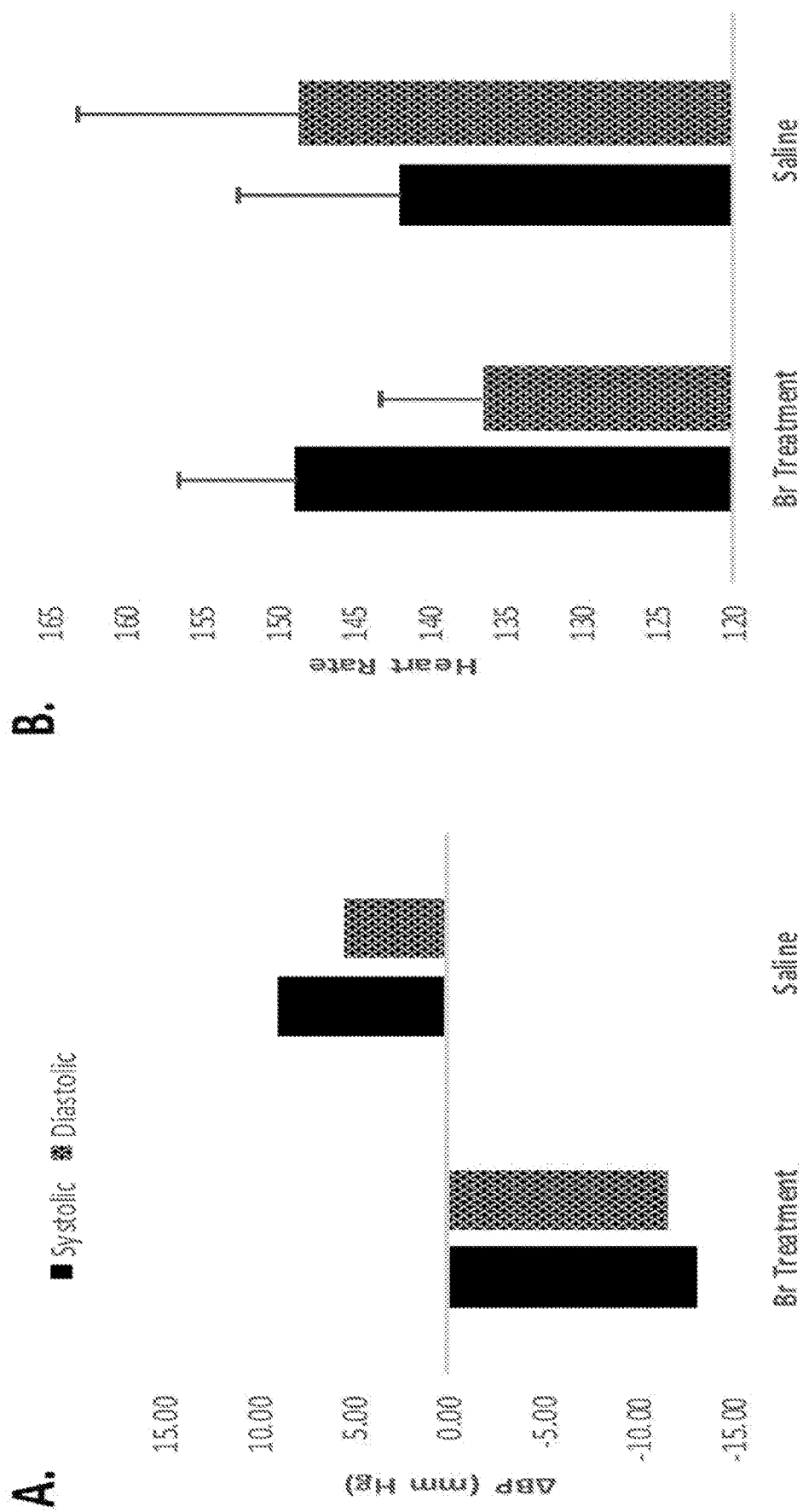
FIG. 5 shows Br⁻ rapidly reduced blood pressure in SHR. (A) In 10 week-old male SHR, single administration of Br⁻ reduced systolic and diastolic blood pressures compared to saline control. (B) Br⁻ induced a possible reduction of heart rate, but the change did not cross a key threshold for statistical significance (p=0.052, T test). (C-D) Measured values for systolic (C) and diastolic (D) blood pressure, denoting statistical significance where achieved. 154.5 μg NaBr per kg rat body weight injected via IP. All "Post Administration" data collected one day following administration. n=8 in Br Treatment group, =5 in saline control. BP & HR measured via tail cuff. *:p<0.05, t test.
Figure 6:
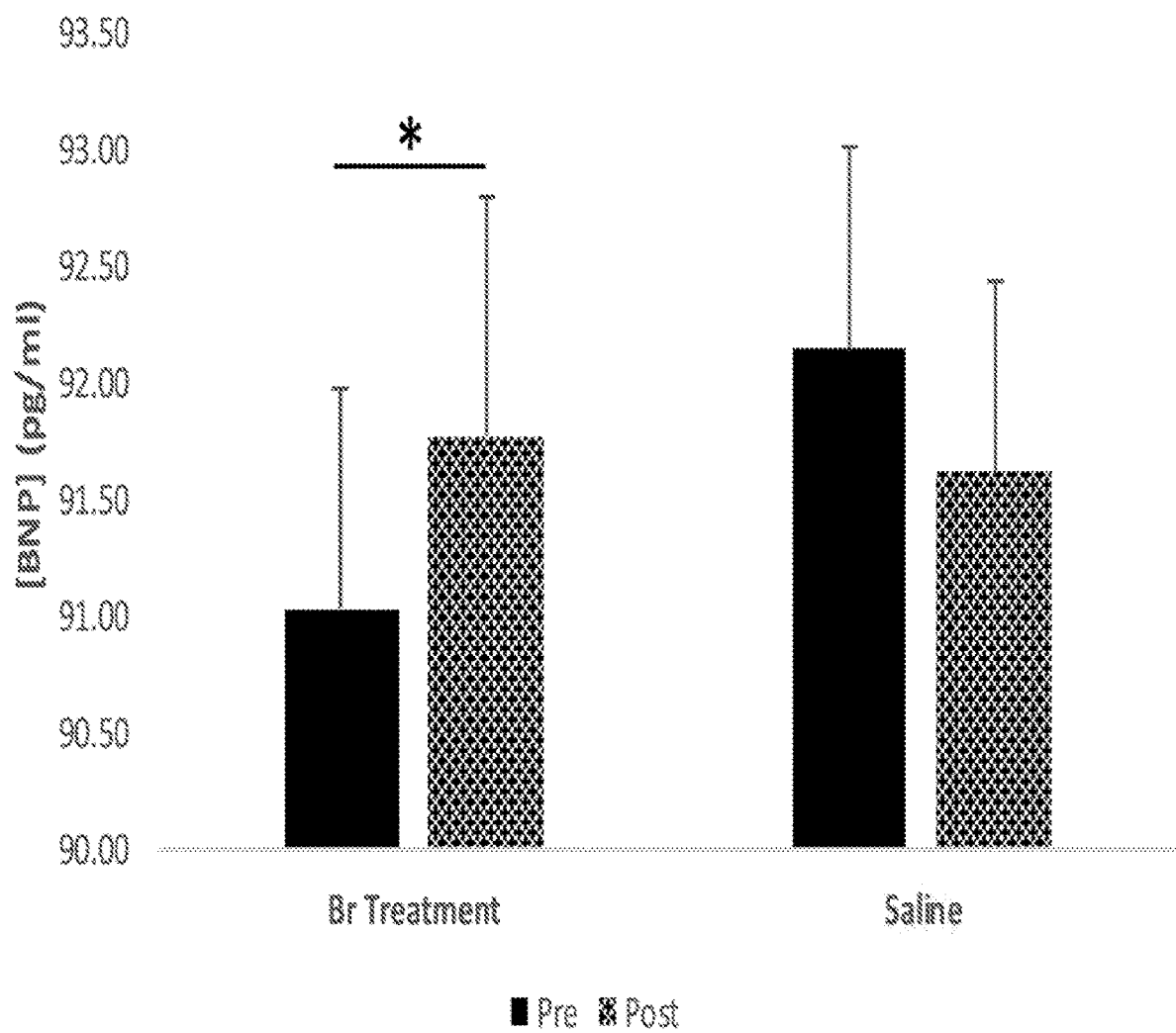
FIG. 6 shows Br⁻ increases BNP concentration. In 10 week-old male SHR, single administration of Br⁻ significantly modulated the serum concentration of BNP peptide, as measured by ELISA assay. 154.5 μg NaBr per kg rat body weight injected via IP. n=8 in Br Treatment group, =5 in saline control. All "Post" administration data collected one day following administration. Baseline serum collection occurred two days prior to treatment. *: p<0.05, t test.

ANP and BNP both utilize cyclic guanosine monophosphate (cGMP) as a second messenger molecule. Healthy individuals can display plasma cGMP levels ranging from 0.1-3.0 pg/ml. Thus, when compared to healthy individuals, increased concentrations of cGMP in plasma or urine can indicate ongoing activity of natriuretic peptide signaling. Moreover, patients with heart failure are reported to display decreased ratios of cGNP to BNP in plasma and urine (Lourenco et al., *Eur. J. Heart Fail.*, 2009), suggesting that there is a critical blockage of signal transduction from BNP to active cGMP. BNP signaling is known to trigger natriuresis and reduce blood pressure, in agreement with the inventors data (FIGS. 5,6). Without wishing to be bound by theory, when practiced as taught herein, embodiments of the invention can modulate the natriuretic peptide signaling system so as to achieve therapeutic reductions in blood pressure. Thus, embodiments as described herein comprise natriuretic peptides, such as ANP and BNP, as bio-indicators for the effectiveness of Br— containing compositions as described herein. Further, natriuretic indicators, such as ANP and BNP, can serve as prognostic and/or diagnostic indicators of a subject in need of a Br— containing composition. For example, ANP and/or BNP levels in a subject can be measured, such as an obese subject or a subject with diabetes, and the subject can be identified as one in need of a Br— containing composition if such levels of ANP and/or BNP are suppressed when compared to physiologically normal levels.

Cardiac fibrosis can develop in a subject as a consequence of cardiovascular disease, such as but not limited to hypertension and myocardial infarction. During fibrosis, cardiac tissue accumulates an excessive amount of collagen fibers. This is sometimes referred to as developing "scar tissue" inside the heart, effectively stiffening the tissue and increasing a subject's risk of developing heart failure. Types I, III, and VI collagen are frequently associated with cardiac fibrosis, and in particular collagens VI and III are suggested by some to be involved with the development of cardiac fibrosis. Collagen IV is also found in cardiac tissue and is reportedly disrupted in some heart failure patients, although collagen IV is present as a minor collagen component in heart tissue. The "gold standard" for diagnosing fibrosis is a biopsy. Other techniques for evaluating cardiac fibrosis include but are not limited to echocardiography; cardiac magnetic resonance; and measuring serum biomarkers such as but not limited to N-terminal collagen I propeptide, serum N-terminal collagen III propeptide, and C-terminal collagen I telopeptide where increases in these biomarkers is correlated with remodeling or fibrosis. Embodiments of the invention can prevent or treat cardiac fibrosis in a subject.

Clinically meaningful changes in a biomarker such as but not limited to blood pressure, heart rate, eGFR, or albuminuria can be readily determined by a doctor or physician who monitors a subject over a period of time, such as but not limited to 1 month, 3 months, 6 months, 9 months, 1 year, or longer. In some instances, a change may be associated with another event in the subject's life, such as but not limited to the development of hypertension during pregnancy or the decline in eGFR in a subject with a history of hypertension. In some instances, a change may be transitory such as but not limited to a temporary increase in urinary albumin levels followed by a return to normal urine albumin levels. In other instances, changes may occur in two or more biomarkers such as but not limited to a subject to develops hypertension and an elevated resting heart rate. Medical societies and authorities such as but not limited to the American Heart Association, the Center for Disease Control, the Blood Pressure Association, the National Kidney Foundation, and the National Institute for Health, can issue recommendations or guidelines for determining ideal, healthy, or normal biomarker levels. The clinical judgement of a doctor or physician can determine whether a particular change in one or more biomarkers is clinically meaningful.

Upon administration to a subject, various biomarkers can be used to monitor the safety, activity, and efficacy of embodiments of the invention. Safety of embodiments can be directly assessed through monitoring the amount of Br— in a subject, such as but not limited to monitoring the amount of Br— in blood, plasma, serum, urine, hair, nails, saliva, sweat, spent or used dialysate, or cells; determining the average concentration of Br— in circulation, such as from blood, serum, or plasma; and determining that the use of the embodiment is safe if the average concentration of Br— is below 1 mM. Activity of the embodiments can be monitored by examining disease biomarkers associated with NP signaling, such as but not limited to blood pressure, heart rate, BNP levels, ANP levels, or cGMP levels. Activity of the embodiment would be evidenced by reductions in blood pressure or heart rate or elevations in BNP, ANP, or cGMP in blood or urine. At the level of an individual subject, efficacy of embodiments of the invention can be evaluated by monitoring the degree of fibrosis in a subject who is treated with an embodiment. In a population, such as in a clinical trial, efficacy of embodiments of the invention can be evaluated by monitoring mortality rates or hospitalization rates.

Use of the Invention in Diabetes, Metabolic Syndrome, and Obesity

Risk of cardiovascular disease is increased if a subject is obese or has diabetes or metabolic syndrome. Embodiments of the invention can be administered to subjects who are obese or who have diabetes or metabolic syndrome. Some embodiments can prevent or treat cardiovascular disease in an obese subject or in a subject with diabetes or metabolic syndrome.

Pathologically, NP expression and signaling is suppressed in obesity, diabetes, and metabolic syndrome. In addition to controlling natriuresis and blood pressure, NP signaling activates hormonal pathways that influence metabolism including converting white adipose tissue to brown adipose tissue, triggering lipolysis in adipose tissue, increasing glucose-stimulated insulin secretion, and promoting lipid oxidation in skeletal muscle (Schlueter et al., Pharmacol. Ther., 144(1):12-27, 2014). Indeed, circulating levels of NPs are reduced in patients with obesity, diabetes, and metabolic syndrome (Schlueter et al., Pharmacol. Ther., 144(1):12-27, 2014). Interestingly, this reduction of NP levels may explain the association of hypertension with obesity, diabetes, and metabolic syndrome.

Embodiments of the invention can therapeutically administered to a subject with diabetes or metabolic syndrome. Embodiments of the invention can be therapeutically administered to an obese subject. Embodiments of the invention can be used to increase circulating ANP, BNP, or cGMP; promote ANP or BNP signaling; reduce blood pressure; prevent or treat diabetes, metabolic syndrome, or obesity in a subject. Embodiments of the invention can prevent or treat cardiovascular disease in a subject who is obese or who has diabetes or metabolic syndrome.

Embodiments of the invention can be administered alone to a subject, in combination with another pharmaceutical drug, as part of treatment regimen, or a component of a kit. In some embodiments, the other pharmaceutical drug is a drug used to treat diabetes, metabolic syndrome, or obesity, such as but not limited to insulin, amylinomimetic agents, alpha-glucosidase inhibitors, biguanides, dopamine agonists, glucagon-like peptides, meglitinides, sodium glucose transporter 2 inhibitors, sulfonylureas, thiazolidinediones, and dipeptidyl peptidase-4 inhibitors. In some embodiments, the drug comprises regular insulin such as but not limited to Humulin or Novolin, insulin aspart such as but not limited to Novolog or FlexPen; insulin glulisine such as but not limited to Apidra; insulin lispro such as but not limited to Humalog; insulin isophane such as but not limited to Humulin N or Novolin N; insulin degludec such as but not limited to Tresiba; insulin detemir such as but not limited to Levemir; insulin glargine such as but not limited to Lantus; insulin glargine such as but not limited to Toujeo; a combination insulin drug such as but not limited to insulin aspart protamine-insulin aspart, insulin lispro protamine-insulin lispro, human isophane insulin-human insulin regular, insulin dedludec-insulin aspart, NovoLog Mix 70/30, Humalog Mix 75/25, Humalog Mix 50/50, Humalin 70/30, Novolin 70/30, or Ryzodeg; pramlintide such as but not limited to SymlinPen; acarbose such as but not limited to Precose; miglitol such as but not limited to Glyset; metformin such as but not limited to Glucophage, Metformin Hydrochloride ER, Glumetza, Riomet, or Fortamet; a metformin-containing drug such as but not limited to metformin-alogliptin, Kazano, metformin-canagliflozin, Invokamet, metformin-dapagliflozin, Xigduo XR, metformin-empagliflozin, Synjardy, metformin-glipizide, metformin-glyburide, Glucovance, metformin-linagliptin, Jentadueto, metformin-pioglitazone, Actoplus, Actoplus Met, Actoplus Met XR, metformin-repaglinide, PrandiMet, metformin-rosiglitazone, Avandamet, metformin-saxagliptin, Kombiglyze XR, metformin-sitagliptin, Janumet, or Janumet XR; bromocriptine such as but not limited to Parlodel; alogliptin such as but not limited to Nesina; alogliptin-pioglitazone such as but not limited to Oseni; linagliptin such as but not limited to Tradjenta, linagliptin-empagliflozin such as but not limited to Glyzami; saxagliptin such as but not limited to Onglyza; sitagliptin such as but not limited to Januvia; sitagliptin and simvastatin such as but not limited to Juvisync; albiglutide such as but not limited to Tanzeum; dulaglutide such as but not limited to Trulicity; exenatide such as but not limited to Byetta; exenatide extended-release such as but not limited to Bydureon; liraglutide such as but not limited to Victoza; nateglinide such as but not limited to Starlix; repaglinide such as but not limited to Prandin; dapagliflozin such as but not limited to Farxiga; canaglifoxin such as but not limited to Invokana; empaglifozin such as but not limited to Jardiance; empagliflozin-linagliptin such as but not limited to Glyxambi; glimepiride such as but not limited to Amaryl; glimepiride-pioglitazone such as but not limited to Duetact; glimepiride-rosiglitazone such as but not limited to Avandaryl; gliclazide, glipizide such as but not limited to Glucotrol; glyburide such as but not limited to DiaBeta, Glynase, or Micronase; chlorpropamide such as but not limited to Diabinese; tolazamide such as but not limited to Tolinase; tolbutamide such as but not limited to Orinase or TolTab; rosiglitazone such as but not limited to Avandia; or pioglitazone such as but not limited to Actos. In some embodiments, the treatment regimen includes administration of one or more pharmaceutical drugs, each administered separately to a subject; behavioral modification such as dietary changes and increased daily exercise; or surgery such as bariatric surgery.

Embodiments of the invention can be a component of a kit. In one embodiment, the kit includes (a) a container that contains the Br⁻ or Br-comprising composition, and optionally (b) informational material. The informational material can be descriptive, instructional, marketing or other material that relates to the methods described herein and/or the use of the agents for therapeutic benefit. In an embodiment, the kit includes also includes a second agent, such as a pharmaceutical drug as described herein. For example, the kit includes a first container that contains the Br⁻ composition, and a second container that includes the pharmaceutical drug. As another example, the kit includes a container that contains the Br⁻ composition in combination with the pharmaceutical drug.

Use of the Invention in Cancer

Patients with cancer receiving chemotherapeutic or radiation treatment experience an elevated risk of developing cardiovascular disease due to the cancer treatment. Non-limiting examples of the forms of these diseases that can be triggered by cancer treatments comprise Q-T prolongation, hypertension, heart failure, cardiomyopathy, thromboembolism, edema, ischemia, atrial fibrillation, cardiac shock, bradycardia, and kidney injury. Non-limiting examples of specific chemotherapeutics that can cause these forms of disease comprise arsenic trioxide, bevacizumab, bortezomib, cisplatin, anthracyclines, doxorubicin, fluorouracil 5-FU, imatinib, interleukin alpha-2b, lapatinib, lenalidomide, melphalan, mitomycin, mitoantrone, pazopanib, sorafenib, sunitinib, thalidomide, trastuzumab, carmustine, and methotrexate.

Natriuretic peptides can inhibit metastasis, or spreading, of cancerous cells. Increased concentrations of BNP and ANP are associated with decreased incidence of metastasis (Masago et al., *Oncol. Lett.*, 2(2):253-247, 2011; Vesely, Anticancer Res., 34(4):1459-1466, 2014; Serafino and Pierimarchi, *Curr. Med. Chem.*, 21(21):2401-2409, 2014). Moreover, disruptions in collagen IV have also been associated with metastasis (Burnier et al., *Oncogene*, 30:3766-3783, 2011). Embodiments of the invention can be administered to a subject with cancer in order to prevent metastasis.

Embodiments of the invention can administer therapeutically effective amounts of Br⁻ to a subject receiving cancer treatment. Such practice of the invention can prevent or treat cardiovascular disease in a subject with cancer or who has received a cancer treatment. The invention can assist in preventing the development of a form of cardiovascular disease, kidney disease, or a combination thereof in a subject with cancer. Alternatively, the invention can assist in the recovery of the subject who has been treated with one or more cancer treatment regimens. The subject can be receiving radiation treatments, surgery, chemotherapy, or a combination thereof. In some embodiments, the invention can be administered to a subject before, after, or during an individual cancer treatment. The cancer treatment can be chemotherapy, surgery, radiation, or a combination thereof. In some embodiments, the invention can be administered to a subject before the subject is placed onto a cancer treatment regimen. For example, after a subject is diagnosed with cancer yet before the subject begins a set of cancer treatments or surgery, the subject can be administered one or more embodiments of the invention in preparation for the upcoming cancer treatments or surgery. In some embodiments, the invention can be administered to a subject after the subject has completed a cancer treatment regimen. For example, a subject who has completed a specified chemotherapy, radiation, or surgical treatment regimen may still be administered embodiments of the invention in order to assist the recovery of the subject. In another example, a subject can be administered embodiments of the invention days, weeks, months, or years after completing a cancer treatment regimen in order to prevent the development of cardiovascular disease, kidney disease, or a combination thereof. Embodiments of the invention can be similarly administered to subjects who do not complete a cancer treatment regimen, or who change from one cancer treatment regimen to another.

In some embodiments, the invention can comprise an effective amount of Br⁻ and a chemotherapeutic agent, for co-administration a subject. Non-limiting examples of chemotherapy and radiotherapy comprises methotrexate, paclitaxel, brentuximab, brentuximab vedotin, anthracyclines, doxorubicin, doxorubicin lipid complex, fluorouracil, fluorouracil 5-FU, everolimus, pemetrexed, melphalan, pamidronate, anastrozole, exemestane, nelarabine, ofatumumab, bevacizumab, belinostat, tositumomab, carmustine, bleomycin, blinatumomab, bosutinib, busulfan, alemtuzumab, irinotecan, vandetanib, bicalutamide, lomustine, daunorubicin, daunorubicin lipid complex, clofarabine, cabozantinib, dactinomycin, cobimetinib, ramucirumab, cytarabine, cytarabine lipid complex, cytoxan, cyclophosphamide, decitabine, dexamethasone, docetaxel, hydroxyurea, decarbazine, leuprolide, epirubicin, oxaliplatin, asparaginase, asparaginase *Erwinia chrysanthemi*, estramustine, cetuximab, vismodegib, amifostine, etoposide, flutamide, toremifene, panobinostat, fulvestrant, letrozole, degarelix, fludarabine, pralatrexate, floxuridine, obinutuzumab, gemcitabine, afatinib, imatinib, imatinib mesylate, carmustine, eribulin, trastuzumab, altretamine, topotecan, palbociclib, ponatinib, idarubicin, ifosfamide, ibrutinib, axitinib, interferon alpha-2a, peginterferon alpha-2a, gefitinib, romidepsin, ixabepilone, ruxolitinib, cabazitaxel, ado-trastuzumab emtansine, pembrolizumab, carfilzomib, lenvatinib, chlorambucil, sargramostim, cladribine, trifluridine, tipiracil, leuprolide, olaparid, mitotane, vincristine, vincristine lipid complex, procarbazine, megestrol, trametinib, mesna, strontium-89 chloride, mechlorethamine, mitomycin, mitoantrone, busulfan, gemtuzumab ozogamicin, vinorelbine, filgrastim, pegfilgrastim, sorafenib, nilutamide, pentostatin, tamoxifen, mitoxantrone, sonidegib, pegaspargase, denileukin diftitox, nivolumab, alitretinoin, carboplatin, pertuzumab, cisplatin, pomalidomide, prednisone, aldesleukin, mercaptopurine, zoledronic acid, lenalidomide, rituximab, octreotide, dasatinib, regorafenib, histrelin, sunitinib, siltuximab, omacetaxine, thioguanine, dabrafenib, erlotinib, bexarotene, decarbazine, docetaxel, temozolomide, thiotepa, thalidomide, bacillus calmette-guerin (BCG) vaccine, temsirolimus, bendamustine hydrochloride, triptorelin, arsenic trioxide, lapatinib, dinutuximab, valrubicin, panitumumab, vinblastine, bortezomib, tretinoin, azacitidine, pazopanib, teniposide, leucovorin, crizotinib, capecitabine, enzalutamide, ipilimumab, trabectedin, ziv-afibercept, streptozocin, vemurafenib, ibritumomab tiuxetan, goserelin, vorinostat, everolimus, idelalisib, ceritinib, abiraterone, liposomes, deoxyribonucleic acid agents, ribonucleic acid agents, x-rays, gamma rays, and charged particles.

Applications of the Invention

Br⁻ Injection

Dialysis treatments remove dietary Br⁻ from patients, where one report demonstrates a lowering of serum Br⁻ levels from 20.8 µM before dialysis to 12.0 µM, afterwards (Miura et al., 2002). The inventor notes that the pre-dialysis levels are still lower than the average of around 67 µM Br⁻ seen in healthy non-dialysis adults, likely as a result of Br⁻ loss in the previous dialysis treatment. This demonstrated that dietary sources of Br⁻ are apparently insufficient to reverse low Br⁻ levels in between dialysis treatments, underscoring an unmet need that is addressed by embodiments of the present invention. In embodiments, low doses of Br⁻ and Br-comprising compositions can be administered to such subject in order to effectively restore adequate serum Br⁻ levels in these subjects.

In embodiments, one can calculate how much Br⁻ needs to be administered to a subject in order to raise the circulating Br⁻ levels from X μM to Y μM following treatment:

$$(Y \text{ molar concentration} - X \text{ molar concentration}) * (\text{patient extracellular volume}) * \left(79.9 \frac{g}{mol} Br\right) = \text{mass Br to administer}$$

For example, one can calculate the amount of Br⁻ needed to be administered to a subject in order to raise the circulating Br— levels from 12 μM to 60 μM following treatment. Estimating that an individual dialysis subject has approximately 6 L of blood, which at 12 μM Br⁻, would equate to 72 μmol of Br⁻. Using a target concentration of 60 μM, said patient would contain 360 μmol in their bloodstream. Thus, the injection of 288 μmol or 23 mg of Br⁻ into the subject's bloodstream should effectively raise the amount of circulating Br⁻ to 360 μmol. However, the subject would likely consume additional amounts of Br⁻ from his/her standard diet before the next dialysis treatment. As a result, it should further be estimated that if 23 mg was indeed administered, said subject would likely display higher than 60 μM Br⁻ by the next dialysis treatment.

Subjects receiving maintenance dialysis typically consume similar amounts of dietary Br⁻ as the general healthy population. Without wishing to be bound by theory, as a result, their serum Br⁻ levels can oscillate between a rise in serum Br⁻ levels during the 2- or 3-day period between dialysis sessions, due to dietary intake, and a rapid loss of Br⁻ during the dialysis treatment session itself. Without wishing to be bound by theory, a subject in the United States may consume between 4-16 mg for a 2-day period between dialysis treatments, or between 6-24 mg for a 3-day period. As a consequence, if a subject diligently consumes a Br-rich diet, said subject should successfully replace all the lost Br⁻ by the end of said 3-day period. However, a Br-rich diet is not likely to provide sufficient amounts of Br⁻ over a 2-day period. Moreover, neither is a diet with little available Br⁻ likely to provide sufficient amounts of Br⁻. The present invention can be used to prevent the subject from becoming Br— deficient immediately following dialysis.

Thus, embodiments of the invention can comprise an injection comprising 5 mg of Br⁻. In embodiments, the injection can be formulated as a sterile solution of 6.438 mg NaBr in water. In some embodiments, the injection can be administered to subject immediately following the dialysis treatment. In other embodiments, the injection can be administered before the dialysis treatment or during the dialysis treatment. For example, by administering 5 mg of Br⁻, a subject with approximately 6 L of blood can see their serum Br⁻ raised by approximately 10 μM. If the subject's serum Br⁻ is 12 μM before receiving the injection, the final Br⁻ concentration would be about 22 μM Br⁻ which is above the threshold for Br— deficiency. Thus, by administering a therapeutically effective amount of Br⁻ to the subject after dialysis, the invention can assist a dialysis patient in maintaining adequate amounts of Br⁻.

Embodiments of the invention can be used to reduce a subject's risk of developing a form of cardiovascular disease due to the dialysis treatment. Non-limiting examples of said forms of cardiovascular disease include atherosclerotic heart disease, acute myocardial infarction, congestive heart failure, cerebrovascular accident, transient ischemic attack, stroke, peripheral heart disease, atrial fibrillation, infection, sudden cardiac arrest, and ventricular arrhythmia.

Embodiments of the invention can be used to prevent a form of cardiovascular disease and/or kidney disease in a subject with a pre-existing form of cardiovascular disease. Non-limiting forms of cardiovascular disease and/or kidney disease include vascular disease, chronic kidney disease, end stage renal disease, glomerular disease, tubular disease, kidney injury, acute kidney injury, sepsis-induced kidney injury, drug-induced kidney injury, hypovolemia-induced kidney injury, ischemic kidney injury, fibrosis, vascular disease, hypertension, salt-sensitive hypertension, heart attack, heart failure, cardiac remodeling, cardiac fibrosis, atherosclerosis, stroke, arterial stiffening, vascular wall thickening, thickening of the peritoneal membrane, dyslipidemia, blood clot, anemia, an acid-base imbalance, hypercholemia, infection, sepsis, thrombosis, coronary artery disease, ischemic heart disease, peripheral artery disease, or any combination thereof. For example, embodiments of the invention may be administered to a subject with hypertension in order to prevent the development of a kidney injury or a form of kidney disease in said subject. As another example, embodiments of the invention may be administered to a subject with chronic kidney disease in order to prevent the development of atherosclerosis or another form of cardiovascular disease in said subject.

Replacement of Br⁻ in Dialysis Patients

The invention can be injected through various formats to patients on dialysis, where such formats are discussed below.

For patients with an acute kidney injury receiving continuous renal replacement therapy (CRRT), embodiments as described herein can be injected through a needle and syringe to a subject, with non-limiting examples of the injection method including intramuscular, intradermal, subcutaneous, intravenous, intraosseous, intraperitoneal, intracardiac, intrathecal, epidural, intraarticular, intracavernous, and intravitreal. In this example, the Br⁻ and Br-comprising compositions can be distributed in a vial requiring a medical professional to draw up an appropriate amount of the composition into a syringe for administration, which conveniently allows the medical professional to adjust the administered dose to the individual needs of the patient. Alternatively, the invention can be distributed in a pre-filled syringe to reduce the number of actions required of the medical professional.

In another embodiment, compositions are injected into a replacement fluid during CRRT. In this case, the invention can be injected or infused into the patient's bloodstream before or after the blood is contacted with a filter. In other words, the compositions can be administered "pre-filter" or "post-filter." In some embodiments, compositions are administered to the bloodstream while the blood is outside the body, also termed extracorporeal administration. In some embodiments, compositions are distributed in a bag that is compatible with intravenous administration.

In another embodiment, compositions are added to an amount of CRRT dialysate, causing the dialysate to contain therapeutically effective amounts of Br⁻. As a result, when the dialysate would be used during CRRT, the dialysate would be less likely to remove Br⁻ from the patient. Moreover, this embodiment would also enable therapeutically effective amounts of Br⁻ to be transferred from the dialysate to the patient, if desired.

Administration to Patients with Cardiovascular Disease and/or Kidney Disease

Some embodiments of the invention can be injected into subjects with a form of cardiovascular disease, kidney disease, or a combination of the two diseases. Non-limiting examples of ongoing diseases and symptoms that can be treated by the invention include cardiovascular disease; vascular disease; kidney disease, including chronic kidney disease, ESRD, glomerular disease, and tubular disease; kidney injury, including acute kidney injury, sepsis-induced kidney injury, drug-induced kidney injury, hypovolemia-induced kidney injury, and ischemic kidney injury; fibrosis; hypertension, including salt-sensitive hypertension; heart attack; heart failure; cardiac remodeling; cardiac fibrosis; atherosclerosis; stroke; arterial stiffening; vascular wall thickening; thickening of the peritoneal membrane; dyslipidemia; blood clot; anemia; an acid-base imbalance; or hypercholemia.

In cardiovascular disease, tissue remodeling of the heart and/or vasculature is a notable feature of disease progression. For example, thickening of the cardiac ventricular wall can indicate chronic stress on the heart, and can be seen in patients at greater risk of developing severe heart disease. As another example, thickening of vascular walls, such as measured by the carotid intima-media thickness, is a risk factor for coronary heart disease (Nambi et al., 2012). Without wishing to be bound by theory, the invention acts on the extracellular mechanisms that drive tissue remodeling and fibrosis. Thus, embodiments of the invention can be used to treat cardiovascular disease.

A fundamental feature of kidney disease is the perturbation of renal function. Such perturbation can trigger biologic feedback loops whereby small losses in renal function can conceivably be amplified into more severe loss of function. Considering that kidneys are responsible for maintaining $Br^-$ levels in healthy adults, dysregulation of $Br^-$ homeostasis is possible in patients with kidney disease. Indeed, urinary excretion of $Br^-$ is positively associated with $Na^+$ excretion, while elevated levels of urinary sodium are associated with poor prognosis in patients with chronic kidney disease (CKD). Thus, an accelerated depletion of $Br^-$ can occur in CKD during disease progression. Embodiments of the invention can be used to provide low doses and/or therapeutically effective amounts of $Br^-$ to patients with kidney disease as a strategy for stabilizing the disease, which would be a positive step towards disease treatment.

Kidney transplantation is a treatment option for some ESRD patients, with the goal of providing one or two fully-functional kidneys to the patient. Restoration of adequate $Br^-$ levels is important for allowing a transplant recipient to regain their health after the operation. Such a transplant recipient can benefit from also receiving embodiments of the invention as described herein, therapeutic amounts of $Br^-$ as described herein, via administration of the invention as described herein, to supplement in the restoration or maintenance of proper $Br^-$ levels as described herein.

Prevention of Cardiovascular Disease and/or Kidney Disease

Embodiments of the invention can be used to prevent development of cardiovascular disease and/or kidney disease in an individual. Analogously, vaccine injections can be used to reduce one's risk of developing a specific infectious disease for a period of time, and often requiring booster shots. Similarly, administration of embodiments of the invention, such as by injection into a subject, can reduce the subject's risk of cardiovascular disease and/or kidney disease. In this case, similar to a vaccine, the invention can be administered at regular intervals to the subject in order to maintain the reduced risk of disease. For example, the invention can be administered hourly, twice a day, daily, weekly, monthly, every other month, quarterly, semi-annually, annually, or another regularly repeating interval. Alternatively, the need for administering the invention can be determined by measuring the level of a serum, blood, salivary, or urine biomarker, such as but not limited to $Br^-$, $SCN^-$, collagen IV, lipids, cholesterol, high-density lipoprotein, low-density lipoprotein, very-low-density lipoprotein, homocysteine, creatinine, c-reactive protein, cystatin C, tryglyceride, protein, albumin, blood pressure, heart rate, cGMP, BNP, ANP, lipid oxidation, protein oxidation, kidney injury molecule 1, neutrophil gelatinase-associated lipocalin, or a combination thereof. Non-limiting methods for measuring these biomarkers include an immunoassay, immunosorbent assay, immunoprecipitation assay, colorimetric assay, column chromatography, mass spectrometry, inductively coupled plasma mass spectrometry, x-ray florescence, neutron activation analysis, western blotting, and enzyme-linked immunosorbant assay (ELISA). In embodiments, the assay can comprise an anti-ANP or anti-BNP antibody, for example. In embodiments, the anti-ANP and/or anti-BNP antibody is a monoclonal or polyclonal antibody. For example, commercially available assays for evaluating BNP, ANP, and the like are available to the skilled artisan, with non-limiting examples including the atrial natriuretic factor blood test, the atrial natriuretic factor levels blood test, the atrial natriuretic protein blood test, the B-type natriuretic peptide (plasma) test, and the N-terminal pro-B type natriuretic peptide test available from clinical laboratory medicine facilities.

As an example, the biomarker, such as ANP and/or BNP, can be measured using lateral flow immunoassays, also known as immunochromatography assay or a strip test. Lateral flow immunoassays comprise immunoassays adapted to operate along a single axis to suit the test strip format. A typical lateral flow test strip comprises a sample pad (an adsorbent pad onto which the test sample is applied), a conjugate or reagent pad (this contains binding agents, such as antibodies, specific to the target analyte conjugate to colored particles, such as colloidal gold nanoparticles or latex microspheres), reaction membrane (typically a nitrocellulose or cellulose acetate membrane onto which anti-target analyte binding agents, such as antibodies, are immobilized in a line that crosses the membrane to act as a capture zone or test line. A control zone will also be present, containing antibodies specific for the conjugate antibodies), and a wick or waste reservoir (a further absorbent pad designed to draw the sample across the reaction membrane by capillary action and collect it). The components of the strip are usually fixed to an inert backing material and may be presented in a simple dipstick format or within a plastic casing with a sample port and reaction window showing the capture and control zones.

In embodiments, the antibody or fragment thereof can be specific for a natriuretic peptide, such as ANP (anti-ANP) and/or BNP (anti-BNP), or amino acid sequences thereof. The antibody can be a polyclonal antibody or a monoclonal antibody. The antibody or fragment thereof can be attached to a molecule that is capable of identification, visualization, or localization using known methods. Suitable detectable labels include radioisotopic labels, enzyme labels, non-radioactive isotopic labels, fluorescent labels, toxin labels, affinity labels, and chemiluminescent labels.

Atrial natriuretic peptide (ANP) is synthesized in myo-endocrine cells of the heart from which it is released into the circulation. It exerts natriuretic, diuretic, and vasodilatory effects through stimulation of guanylate cyclase-linked NPR-A receptors. It plays an important role in blood volume and blood pressure homeostasis.

Atrial Natriuretic Peptide (ANP) Sequence:

```
                                            (SEQ ID NO: 1)
Ser-Leu-Arg-Arg-Ser-Ser-Cys-Phe-Gly-Gly-Arg-Met-
Asp-Arg-Ile-Gly-Ala-Gln-Ser-Gly-Leu-Gly-Cys-Asn-
Ser-Phe-Arg-Tyr
```

Brain natriuretic peptide (type B natriuretic peptide, BNP) was originally isolated from brain, but is mainly produced in myoendocrine cells of the heart ventricles from which it is released into the circulatory system. BNP is involved in blood pressure control and cardiovascular homeostasis.

Brain Natriuretic Peptide (BNP) Sequence:

```
                                            (SEQ ID NO: 2)
SER-PRO-LYS-MET-VAL-GLN-GLY-SER-GLY-CYS-PHE-GLY-
ARG-LYS-MET-ASP-ARG-ILE-SER-SER-SER-SER-GLY-LEU-
GLY-CYS-LYS-VAL-LEU-ARG-ARG-HIS
```

An individual's risk for developing cardiovascular disease and/or kidney disease can be determined by assessing one or several factors. For example, the subject can have a personal or family history of a form of cardiovascular disease; vascular disease; kidney disease, including chronic kidney disease, ESRD, glomerular disease, and tubular disease; kidney injury, including acute kidney injury, sepsis-induced kidney injury, drug-induced kidney injury, hypovolemia-induced kidney injury, and ischemic kidney injury; fibrosis; hypertension, including salt-sensitive hypertension; heart attack; heart failure; cardiac remodeling; cardiac fibrosis; atherosclerosis; stroke; arterial stiffening; vascular wall thickening; thickening of the peritoneal membrane; dyslipidema; blood clot; anemia; an acid-base imbalance; or hypercholemia. For example, the subject can consume a high-salt or high-sodium diet.

Administration of a Pharmaceutical Drug Using the Invention

Some drugs are known to deplete Br⁻ from patients, including but not limited to diuretic agents. Patients receiving these drugs can experience low Br⁻ levels. Embodiments of the invention can be useful for administering a therapeutically effective amount of Br⁻ to these patients. In some embodiments, low doses of Br⁻ or Br-comprising compositions are administered. In some embodiments, only an amount of Br⁻ or Br-comprising composition sufficient to raise the serum levels of Br⁻ above 20 μM is administered to the subject. In other embodiments, only an amount of Br⁻ or Br-comprising composition sufficient to raise the serum Br⁻ level to an amount between about 20 μM and about 1 mM is administered to the subject.

Many types of drugs can be administered via injection to patients in combination with the invention. Non-limiting examples of types of drugs include small molecules, proteins, recombinant proteins, antibodies, vaccines, and biologics. In some embodiments, the drug may act on the kidney, heart, blood, bone marrow, or vasculature. Non-limiting examples of drug classes include blood pressure controlling agents, angiotensin-converting enzyme inhibitors, angiotensin receptor blockers, beta blocking agents, alpha blocking agents, antiarrhythmic agents, blood thinners, alpha agonists, sodium channel blocking agents, calcium channel blocking agents, antiplatelet agent, antihyperlipidemic agents, statin therapies, nonsteroidal anti-inflammatory drugs, loop diuretics, thiazide diuretics, potassium-sparing diuretics, vasodilators, renin inhibitors, dopamine, dopamine receptor agonists, thrombolytic agents, erythropoietin, erythropoietic stimulating agents, vitamins, vitamin analogues, drugs used in the management of ESRD, anti-infective agents, antibiotics, antifungals, and cancer chemotherapeutic agents. Non-limiting examples of drugs comprise captopril, enalapril, fosinopil, lisinopril, perindopril, quinapril, trandolapril, benazepril, ramipril, azilsartan, candesartan, telmisartan, fimasartan eprosartan, irbesartan, losartan, olmesartan, valsartan, doxazosin, phentolamine, indoramin, phenoxybenzamine, tolazoline, bucindolol, carvedilol, labetalol, tamsulosin, terazosin, prazosin, alfuzosin, timolol, betaxolol, propranolol, atenolol, nadolol, nebivolol, oxprenolol, pindolol, propranolol, metoprolol, sodium nitroprusside, hydralazine, adenosine, sildenafil, vardenafil, tadalafil, prostacyclin, nitric oxide, amiodarone, mexiletine, disopryamide, propafenone, diltiazem, dihydropyridines, amlodipine, cilnidipine, felodipine, isradipine, nimodipine, lercanidipine, levamlodipine, nicardipine, nitrendipine, nifedipine, verapamil, spironolactone, bumetanide, ethacrynic acid, epitizide, metolazone, amiloride, triamterene, torsemide, furosemide, indapamide, triamterene, hydrochlorothiazide, chlorothiazide, bendroflumethiazide, chlorthalidone, celecoxib, meloxicam, ibuprofen, naproxen, diclofenac, aspirin, dipyridamole, clopidogrel, cilostazol, ticlopidine, lovastatin, niacin, simvastatin, ezetimibe, warfarin, carperitide (recombinant ANP), nesiritide (recombinant BNP), tinzaparin, enoxaparin, heparin, atorvastatin, fluvastatin, pravastatin, rosuvastatin, aliskiren, alteplase, anistreplase, reteplase, tenecteplase, streptokinase, tissue plasminogen activator, urokinase, recombinant human erythropoietin, epoetin alpha, epoetin beta, darbepoetin alpha, methoxy polyethylene glycol-epoetin beta, Epo, Procrit®, Epogen®, Aranesp, Mircera, vitamin D, rocaltrol, calcitriol, Zemplar®, hectorol, doxercalciferol, carnitor, levocarntine, lepiridun, reteplase, alteplase, peginesatide, iron, sodium ferric gluconate, vitamin B12, Darbepoetin, midazolam hydrochloride, diazepam, calcium gluconate, calcitonin, deferoxamine, doxercalciferol, ibandronate, pamidronate, paricalcitol, methotrexate, paclitaxel, brentuximab, brentuximab vedotin, anthracyclines, doxorubicin, doxorubicin lipid complex, fluorouracil, fluorouracil 5-FU, everolimus, pemetrexed, melphalan, pamidronate, anastrozole, exemestane, nelarabine, ofatumumab, bevacizumab, belinostat, tositumomab, carmustine, bleomycin, blinatumomab, bosutinib, busulfan, alemtuzumab, irinotecan, vandetanib, bicalutamide, lomustine, daunorubicin, daunorubicin lipid complex, clofarabine, cabozantinib, dactinomycin, cobimetinib, ramucirumab, cytarabine, cytarabine lipid complex, cytoxan, cyclophosphamide, decitabine, dexamethasone, docetaxel, hydroxyurea, decarbazine, leuprolide, epirubicin, oxaliplatin, asparaginase, asparaginase *Erwinia chrysanthemi*, estramustine, cetuximab, vismodegib, amifostine, etoposide, flutamide, toremifene, panobinostat, fulvestrant, letrozole, degarelix, fludarabine, pralatrexate, floxuridine, obinutuzumab, gemcitabine, afatinib, imatinib, imatinib mesylate, carmustine, eribulin, trastuzumab, altretamine, topotecan, palbociclib, ponatinib, idarubicin, ifosfamide, ibrutinib, axitinib, interferon alpha-2a, peginterferon alpha-2a, gefitinib, romidepsin, ixabepilone, ruxolitinib, cabazitaxel, ado-trastuzumab emtansine, pembrolizumab, carfilzomib, lenvatinib, chlorambucil, sargramostim, cladribine, trifluridine, tipiracil, leuprolide, olaparid, mitotane, vincristine, vincristine lipid complex, procarbazine, megestrol, trametinib, mesna, strontium-89 chloride, mechlorethamine, mitomycin, mitoantrone, busulfan, gemtuzumab ozogamicin, vinorelbine, filgrastim, pegfilgrastim, sorafenib, nilutamide, pentostatin, tamoxifen, mitoxantrone, sonidegib, pegaspargase, denileukin diftitox, nivolumab, alitretinoin, carboplatin, pertuzumab, cisplatin, pomalidomide, prednisone, aldesleukin, mercaptopurine, zoledronic acid, lenalidomide, rituximab, octreotide, dasatinib, regorafenib, histrelin, sunitinib, siltuximab, omacetaxine, thioguanine, dabrafenib, erlotinib, bexarotene, decarbazine, docetaxel, temozolomide, thiotepa, thalidomide, bacillus calmette-guerin (BCG) vaccine, temsirolimus, bendamustine hydrochloride, triptorelin, arsenic trioxide, lapatinib, dinutuximab, valrubicin, panitumumab, vinblastine, bortezomib, tretinoin, azacitidine, pazopanib, teniposide, leucovorin, crizotinib, capecitabine, enzalutamide, ipilimumab, trabectedin, ziv-afibercept, streptozocin, vemurafenib, ibritumomab tiuxetan, goserelin, vorinostat, everolimus, idelalisib, ceritinib, abiraterone, liposomes, deoxyribonucleic acid agents, ribonucleic acid agents, penicillin, amoxicillin, cephalexin, erythromycin, clarithromycin, azithromycin, ciprofloxacin, levofloxacin, ofloxacin, sulfamethoxazole, trimethoprim, fosfomycin, nitrofurantoin, ceftriaxone, clavulanate, clindamycin, doxycycline, tetracycline, clotrimazole, econazole nitrate, miconazole, terbinafine, fluconazole, ketoconazole, and amphotericin. In some embodiments, a drug and a composition of the invention can be co-administered to a subject in a single injection. In other embodiments, a drug and a composition of the invention can be separately administered to a subject. For example, a composition of the invention can be injected into a subject and a drug can be separately administered to the same subject. Traditional medicines, such as traditional Chinese medicines, can be administered. Moreover, the invention can be used with medical devices, such as but not limited to bandages, intravascular stents, and ingestible devices such as pill cameras. Non-limiting examples of diseases and conditions that the invention can be useful in addressing include cardiovascular disease, vascular disease, kidney disease, chronic kidney disease, end stage renal disease, glomerular disease, tubular disease, kidney injury, acute kidney injury, sepsis-induced kidney injury, drug-induced kidney injury, hypovolemia-induced kidney injury, ischemic kidney injury, fibrosis, vascular disease, hypertension, salt-sensitive hypertension, heart attack, heart failure, cardiac remodeling, cardiac fibrosis, atherosclerosis, stroke, arterial stiffening, vascular wall thickening, thickening of the peritoneal membrane, dyslipidemia, blood clot, anemia, an acid-base imbalance, hypercholemia, infection, sepsis, thrombosis, coronary artery disease, ischemic heart disease, peripheral artery disease, or any combination thereof.

Use of Embodiments as Source of Nutrition

Kidney disease and cardiovascular disease are chronic conditions, requiring clinical management with few cures available. Diet and exercise are frequently prescribed as practical steps that patients can take to modify their risk of disease. Additionally, dietary supplements are routinely used in effort to improve the nutritional state of patients. Yet, while there is a general recognition of the importance of nutrition in the clinical care of kidney disease and cardiovascular disease, the prevalence of both diseases remains elevated. The inability to control these diseases by nutrition implies that either the current nutritional approach is insufficient or there is severe noncompliance on the part of patients. To consider both options in greater detail, the strength of a nutritional approach requires a complete understanding of the required nutrients as well as the administration of these nutrients in a format that enables sufficient amounts of the nutrients to be absorbed. For example, many forms of magnesium are available as dietary supplements, with two notable examples being magnesium chloride and magnesium oxide. Between the two, magnesium chloride is absorbed into the body at a significantly greater proportion than is magnesium oxide. Thus, a given amount of magnesium chloride in a dietary supplement will provide more bioavailable $Mg^{2+}$ than will the same amount of magnesium oxide. Similarly, the compositions disclosed herein eliminate many, if not all, of the potential bioavailability complications that must be considered if therapeutically effective amounts of $Br^-$ were to be administered orally.

Beyond the completeness of a particular nutritional regimen, patient compliance can be notoriously problematic to maintain. Nearly all patients have favorite foods, many of which are not nutritious but rather can worsen the health of the patient. For example, high sodium intake is prevalent in western society yet is associated with hypertension as well as some forms of kidney disease. Poor patient compliance can confound even the best designed nutritional plans.

Recognizing the problems with nutritional management of these diseases, the invention combines nutritionally-informed biochemistry with the controlled dosing afforded by physician-administered pharmaceutical drugs. As a result, practice of the invention can improve the nutritional state of a patient with cardiovascular disease and/or kidney disease while providing the physician with an enhanced ability to manage the overall health of the patient. Some embodiments of the invention can administer $Br^-$ to a subject in need of nutrition. Said subject may have be low or deficient in $Br^-$, as determined through one or more of the diagnostic testing methods described herein, while practice of the invention can provide a nutritionally effective amount of $Br^-$ to the subject. Some embodiments of the invention can be combined with other nutrients and the mixture administered via injection to a subject. Some embodiments of the invention can be administered through a tube, with a non-limiting example such as a feeding tube. Some embodiments of the invention can be used as a source of parenteral nutrition for a subject, either by administering $Br^-$ alone or in combination with other nutrients.

Several dietary supplements are available for dialysis patients, such as the Dialyvite (Hillestad Pharmaceuticals, Woodruff, Wis.), Renaltab (Renalab, Templeton, Calif.), and ProRenal® (Nephroceuticals, Tucson, Ariz.). Notably, these vitamins do not administer sufficient amounts of $Mg^{2+}$ to patients yet dialysis depletes patients of $Mg^{2+}$, increasing patient risk of experiencing a mortality event (Sakaguchi et al., 2013). Moreover, as dietary supplements, these vitamins are orally administered to patients, yet dialysis patients must diligently monitor and reduce their fluid intake to avoid fluid overload, which can create complications when trying to swallow their vitamins with small amounts of fluid.

Mg-deficiency is associated with increased risk of mortality in dialysis patients (Sakaguchi et al., 2013). Patients with serum $Mg^{2+}$ levels between 2.5 and 3.0 mg/dl have shown the lowest risk of developing cardiovascular disease (Sakaguchi et al., 2013). In some patients with hyperphosphatemia, low $Mg^{2+}$ levels can promote risk of calcification, including vascular calcification (Sakaguchi et al., 2014). Embodiments of the invention comprise an amount of $Mg^{2+}$ between about 50 mg and about 600 mg, in addition to comprising an effective amount of $Br^-$, for administration to a subject. In some embodiments, the subject can correct Mg-deficiency in a subject. In some embodiments, $Mg^{2+}$ levels can be measured in the blood, serum, plasma, or urine of a subject.

Embodiments comprising both $Br^-$ and $Mg^{2+}$ can display enhanced effectiveness in preventing cardiovascular disease, kidney disease, or a combination thereof in a subject. For example, if $Br^-$ levels are adequate in a subject yet $Mg^{2+}$ levels are deficient, the subject may still be at risk of developing a form of CVD. Conversely, if $Mg^{2+}$ levels are adequate yet $Br^-$ levels are deficient, the subject may still be at risk of developing a form of CVD. In some embodiments, the subject can be receiving dialysis treatments. In some embodiments, the subject can be deficient in $Br^-$, $Mg^{2+}$, or a combination thereof.

Co-Administration of $Br^-$ and Nutrients to Dialysis Patients

Patients on dialysis are advised to take multivitamins in order to compensate for treatment-induced nutritional imbalances. There are several vitamins that are formulated specifically for dialysis patients, yet in spite of their widespread use, dialysis still places patients at significant risk of developing cardiovascular disease. In other words, the currently available dietary supplements are insufficient for adequately preventing cardiovascular disease in patients on dialysis. Consequently, these patients experience high risk of developing cardiovascular disease, in part due to these inadequate vitamins.

It has not been known that $Br^-$ is important for heart health and/or vascular health, yet the inventor here shows that loss of $Br^-$ is associated with increased mortality in a rat model of hypertension and kidney disease (FIG. 1). Dialysis alters the circulating levels of $Br^-$ as well as many other nutrients in subjects, and this combined dysregulated nutritional state contributes to the elevated risk that the subject will develop a side effect of dialysis. Thus, and without being bound by theory, subjects on dialysis can benefit from being administered embodiments of the invention as well as a dialysis-specific formula of vitamins and minerals. This synergistic activity of $Br^-$ and other vitamins may explain why commercially-available dialysis vitamins are unable to prevent risk of cardiovascular disease. Specifically, the lack of $Br^-$ in current vitamin formulations may severely limit the efficacy of those vitamins. Thus, embodiments of the invention can be used to prevent or treat a side effect of dialysis by administering therapeutic amounts of $Br^-$ in combination with a complete set of dialysis vitamins. Such treatment can simultaneously correct the ongoing Br-deficiency in a subject on dialysis as well as provide appropriate nutritional supplementation to the subject. This combination treatment can yield an improved patient outcome due to its comprehensive approach of targeting patient $Br^-$ levels and patient nutrition. Moreover, as an injection product, compositions of the invention can be more convenient than requiring a patient to swallow another vitamin pill with a minimum amount of fluid. To this end, the inventor developed an embodiment of the invention that administers a therapeutically effectively amount of $Br^-$ as well as targeted levels of nutrients to patients on dialysis.

Embodiments of the invention can comprise compositions designed to administer $Br^-$ as well as one or more other compositions, such as vitamins, nutrients, or minerals. In some embodiments, the invention comprises compositions comprising $Br^-$, $Mg^{2+}$, selenium, iron, zinc, B vitamins, vitamin C, vitamin E, and/or vitamin D. Such embodiments can be administered via injection in order to ensure patient compliance and minimize the impact of bioavailability issues. Non-limiting examples of other routes of administration are described herein.

Embodiments of the invention comprise the following composition:
5 mg $Br^-$ (NaBr),
100 mg magnesium ($MgCl_2$),
1.2 mg of vitamin $B_1$ (thiamine),
1.7 mg of vitamin $B_2$ (riboflavin),
20 mg of vitamin $B_3$ (niacin),
10 mg of vitamin $B_5$ (pantothenic acid),
50 mg of vitamin $B_6$ (pyridoxine),
300 µg of vitamin $B_7$ (biotin),
0.8 mg of vitamin $B_9$ (folic acid),
6 µg of vitamin $B_{12}$ (cobalamin), and
100 mg of vitamin C (ascorbic acid).

Dialysis patients are advised to limit their fluid intake, which can be challenging when the patient is trying to take one or more dietary supplements. Embodiments of the invention can eliminate the need for dialysis patients to consume one or more dietary supplements with minimal amounts of fluid. For example, injection of the compositions as described herein eliminates the need for dialysis patients to try and consume one or more dietary supplements with minimal amounts of fluid.

This injection product can be administered to a patient immediately following dialysis. The product can be distributed in various formats, including a pre-filled syringe; a vial; or in packaging with connectors for infusing the product into the patient's bloodstream via a dialysis access port, a fistula, a catheter, a graft, or a dialysis tube. The product eliminates the need for a patient to consume a dietary supplement with fluid and ensures that adequate amounts of the nutrients are present in the circulation.

Use of Embodiments in Subjects with Cancer

Cancer treatments can deplete $Br^-$ from a subject. For example, Weber and colleagues (1984) documented the depletion of $Br^-$ from four patients with acute myelogenous leukemia after induction of chemotherapy treatments. Moreover, it is known that exposure to chemotherapeutics or radiation, during the course of cancer treatments, can lead to elevated risk of developing a form of cardiovascular disease or kidney disease. Non-limiting examples of the forms of these diseases that can be triggered by cancer treatments comprise Q-T prolongation, hypertension, heart failure, cardiomyopathy, thromboembolism, edema, ischemia, atrial fibrillation, cardiac shock, bradycardia, and kidney injury. Non-limiting examples of specific chemotherapeutics that can cause these forms of disease include arsenic trioxide, bevacizumab, bortezomib, cisplatin, anthracyclines, doxorubicin, fluorouracil 5-FU, imatinib, interleukin alpha-2b, lapatinib, lenalidomide, melphalan, mitomycin, mitoantrone, pazopanib, sorafenib, sunitinib, thalidomide, trastuzumab, carmustine, and methotrexate.

Embodiments of the invention can administer effective amounts of $Br^-$ to a subject receiving cancer treatment. For example, such embodiments can prevent the development of a form of cardiovascular disease, kidney disease, or a combination thereof in a subject with cancer. The subject can be receiving radiation treatments, surgery, chemotherapy, or a combination thereof. In some embodiments, the invention can be administered to a subject before, after, or during an individual cancer treatment. The cancer treatment can be chemotherapy, surgery, radiation, or a combination thereof. In some embodiments, the invention can be administered to a subject before the subject is placed onto a cancer treatment regimen. For example, after a subject is diagnosed with cancer yet before the subject begins a set of cancer treatments or surgery, the subject can be administered one or more embodiments of the invention in preparation for the upcoming cancer treatments or surgery. In some embodiments, the invention can be administered to a subject after the subject has completed a cancer treatment regimen. For example, a subject who has completed a specified chemotherapy, radiation, or surgical treatment regimen may still be administered embodiments of the invention in order to assist the recovery of the subject. In another example, a subject can be administered embodiments of the invention days, weeks, months, or years after completing a cancer treatment regimen in order to prevent the development of cardiovascular disease, kidney disease, or a combination thereof. Embodiments of the invention can be similarly administered to subjects who do not complete a cancer treatment regimen, or who change from one cancer treatment regimen to another.

In some embodiments, the invention can comprise co-administration of an effective amount of $Br^-$ and a chemotherapeutic agent to a subject. Non-limiting examples of said chemotherapeutics comprise methotrexate, paclitaxel, brentuximab, brentuximab vedotin, anthracyclines, doxorubicin, doxorubicin lipid complex, fluorouracil, fluorouracil 5-FU, everolimus, pemetrexed, melphalan, pamidronate, anastrozole, exemestane, nelarabine, ofatumumab, bevacizumab, belinostat, tositumomab, carmustine, bleomycin, blinatumomab, bosutinib, busulfan, alemtuzumab, irinotecan, vandetanib, bicalutamide, lomustine, daunorubicin, daunorubicin lipid complex, clofarabine, cabozantinib, dactinomycin, cobimetinib, ramucirumab, cytarabine, cytarabine lipid complex, Cytoxan, cyclophosphamide, decitabine, dexamethasone, docetaxel, hydroxyurea, decarbazine, leuprolide, epirubicin, oxaliplatin, asparaginase, asparaginase *Erwinia chrysanthemi*, estramustine, cetuximab, vismodegib, amifostine, etoposide, flutamide, toremifene, panobinostat, fulvestrant, letrozole, degarelix, fludarabine, pralatrexate, floxuridine, obinutuzumab, gemcitabine, afatinib, imatinib, imatinib mesylate, carmustine, eribulin, trastuzumab, altretamine, topotecan, palbociclib, ponatinib, idarubicin, ifosfamide, ibrutinib, axitinib, interferon alpha-2a, peginterferon alpha-2a, gefitinib, romidepsin, ixabepilone, ruxolitinib, cabazitaxel, ado-trastuzumab emtansine, pembrolizumab, carfilzomib, lenvatinib, chlorambucil, sargramostim, cladribine, trifluridine, tipiracil, leuprolide, olaparid, mitotane, vincristine, vincristine lipid complex, procarbazine, megestrol, trametinib, mesna, strontium-89 chloride, mechlorethamine, mitomycin, mitoantrone, busulfan, gemtuzumab ozogamicin, vinorelbine, filgrastim, pegfilgrastim, sorafenib, nilutamide, pentostatin, tamoxifen, mitoxantrone, sonidegib, pegaspargase, denileukin diftitox, nivolumab, alitretinoin, carboplatin, pertuzumab, cisplatin, pomalidomide, prednisone, aldesleukin, mercaptopurine, zoledronic acid, lenalidomide, rituximab, octreotide, dasatinib, regorafenib, histrelin, sunitinib, siltuximab, omacetaxine, thioguanine, dabrafenib, erlotinib, bexarotene, decarbazine, docetaxel, temozolomide, thiotepa, thalidomide, bacillus calmette-guerin (BCG) vaccine, temsirolimus, bendamustine hydrochloride, triptorelin, arsenic trioxide, lapatinib, dinutuximab, valrubicin, panitumumab, vinblastine, bortezomib, tretinoin, azacitidine, pazopanib, teniposide, leucovorin, crizotinib, capecitabine, enzalutamide, ipilimumab, trabectedin, ziv-afibercept, streptozocin, vemurafenib, ibritumomab tiuxetan, goserelin, vorinostat, everolimus, idelalisib, ceritinib, abiraterone, liposomes, deoxyribonucleic acid agents, ribonucleic acid agents.

Liposomes can refer to vesicles having a self-closed structure of generally spherical or oval shape formed from one or more lipid layers and having an interior lumen containing a part of the solvent. These nanosized, lipid bilayered vesicles can be utilized as drug delivery systems owing to their efficiency, biocompatibility, nonimmunogenicity, enhanced solubility of chemotherapeutic agents and their ability to encapsulate a wide array of drugs known in the art. Liposomes can be activated by heat, allowing the targeted delivery of a drug to a specific tissue or tumor site in a subject. Liposomes, including heat-activated liposomes, can be used to administer embodiments of the invention to a subject. Other embodiments of the invention can be administered to a subject who is administered another liposome-delivered drug. Other embodiments of the invention can be formulated as a combination drug product with another liposome-delivered drug.

Embodiments of the invention can be administered to a subject together with a DNA agent or RNA agent, or at about the same time as administration of a DNA agent or RNA agent. Deoxyribonucleic acid (DNA) agents and ribonucleic acid (RNA) agents can refer to compositions comprising a sequence of DNA or RNA, respectively, that is formulated for administration to a subject, such as but not limited to a subject with cancer. The sequence can be an oligonucleotide, a double-stranded DNA sequence, an enzyme, or an aptamer. The sequence can be administered to a subject by a vector, a plasmid, a liposome, a polymer, or a drug delivery device. The sequence can be used to transfer a gene to a subject or express a therapeutic protein in a subject. The sequence can be used to bind and silence a target gene transcript in a cancerous cell. Some embodiments can be administered before a DNA or RNA agent is administered to a subject. Other embodiments can be administered after a DNA or RNA agent is administered to a subject. Still other embodiments can be co-administered with a DNA or RNA agent to a subject. Still other embodiments can be formulated, manufactured, and packaged with a DNA or RNA agent for co-administration to a subject.

Formulation and Administration Strategies for Embodiments of the Invention

Embodiments of the invention are amenable to a variety of formulations. Embodiments can be formulated as a pill, a patch, a liquid, an injectable liquid, a powder, a lozenge, a food, a drink, a candy, or a gum. Certain embodiments are not formulated for inhalation. Certain embodiments are not formulated with thiocyanate. Certain liquid embodiments are not formulated with greater than 0.1% sodium chloride. Certain embodiments are not formulated as eye drops. Embodiments can be formulated for systemic administration to a subject, such as but not limited to injection or oral administration.

Some embodiments of the invention are combined with another pharmaceutical drug into a combination product, where a non-limiting example includes manufacturing and packaging a combination drug product that comprises an embodiment of the invention and a drug for treating diabetes. Some embodiments are manufactured separately but combined with another pharmaceutical drug prior to administration to a subject, where a non-limited example is combining a liquid embodiment and a liquid diuretic for administration as a single treatment to a subject. Embodiments of the invention can be combined with another other drug listed herein.

Embodiments of the invention can be packed for single administration to a subject, such as not but limited to a single injection of an embodiment to a hospitalized subject. Some embodiments can be packaged for repeated dosing of a subject, such as but not limited to a pill bottle containing a multi-day supply of embodiments or a bubble strip containing a multi-day supply of embodiments.

Embodiments can be administered through one or more formulations and packaging formats. A non-limiting example includes administering embodiments as a daily pill to a subject, where the pill is self-administered at home, and administering injection embodiments to the same subject during regular office visits.

Some embodiments comprise administering doses of $Br^-$ at differing concentrations over a period of time in order to achieve the desired circulating $Br^-$ level in the blood, serum, or plasma of a subject. For example, a subject can be administered a composition comprising a high dose of $Br^-$, such as but not limited to 15-25 mg $Br^-$, followed by subsequent administration of lower doses of $Br^-$, such as but not limited to 1-5 mg $Br^-$ a period time thereafter. This approach can benefit a subject who has serum $Br^-$ levels below 20 µM, where the initial large dose serves to restore serum $Br^-$ levels to between about 50 µM and about 500 µM while the subsequently administered lower doses of $Br^-$ serve to maintain the serum $Br^-$ levels in this range. Another non-limiting example includes administering compositions comprising increasing doses of $Br^-$ to a subject until a desired maintenance dosing is achieved, such as but not limited to increasing dosing from 1 mg $Br^-$ to 3 mg $Br^-$ to 5 mg $Br^-$ and so on until a maintenance dose of 10 mg $Br^-$ is achieved. Still another non-limiting example includes administering a daily maintenance dose of 5 mg $Br^-$ with periodic injections of larger doses such as but not limited to 10 mg $Br^-$, 15 mg $Br^-$, 20 mg $Br^-$, or 25 mg $Br^-$.

Importantly, in order to prevent toxicity, embodiments as described herein do not provide for administering sufficient amounts of $Br^-$ to raise the circulating $Br^-$ concentration above 1 mM in a subject, particularly if two or more separate compositions, each comprising Br—, are administered to the same subject. As a non-limiting example, if a subject is administered a combination of two or more drug formulations each containing Br—, for example a first drug for controlling diabetes combined with a second drug for controlling hypertension, it would be out of scope of the invention for the subject's blood concentration of $Br^-$ to rise above 1 mM. Thus, embodiments as described herein comprise only administering sufficient $Br^-$ to raise and maintain circulating $Br^-$ concentration above at least 20 µM $Br^-$ but not more than 1 mM. Further embodiments administer sufficient $Br^-$ to achieve circulating $Br^-$ concentrations above 50 µM but below 500 µM $Br^-$.

EXAMPLES

Example 1

Dialysis is known to place patients into a chronic state of low $Br^-$ levels. Depletion of $Br^-$ is reported to occur after consumption of a high salt diet. However, the chronic effects of dietary salt on serum $Br^-$ is not known. More importantly, it is not known whether salt-induced depletion of $Br^-$ can cause disease in an individual.

To test whether dietary salt can cause sustained low $Br^-$ levels, Dahl rats were administered a base diet of AIN76A with 8% NaCl for 10 weeks. In parallel, another group of Dahl rats were administered AIN76A without supplemental salt for the same time period. At the end of the study, serum $Br^-$ measurements displayed 25.54 µM $Br^-$ in the normal-salt arm yet only 14.14 µM $Br^-$ in the high salt arm (FIG. 1). Thus, consumption of a high salt diet can cause a sustained depletion of serum $Br^-$, placing a subject into a chronic Br—depleted state.

Example 2

Dialysis is known to place subjects into a chronic state of low $Br^-$ levels. Depletion of $Br^-$ is reported to occur after consumption of a high salt diet. However, the chronic effects of dietary salt on serum $Br^-$ is not known. More importantly, it is not known whether salt-induced depletion of $Br^-$ can cause disease in an individual.

To test whether $Br^-$ can therapeutically treat cardiovascular disease and/or kidney disease, $Br^-$ was administered to Dahl rats while on a high salt (8%) diet. Administration of high salt to Dahl rats is known to trigger hypertension, structural changes in the heart and vasculature, and kidney injury, thus modeling similar pathologic changes occurring in clinical cases of cardiovascular disease and/or kidney disease.

Dahl rats were administered a base diet of AIN76A with 8% NaCl, while a parallel arm was administered AIN76A with 8% NaCl and 300 mg of NaBr per kg of food. Mortality events were counted over the 10 week study. High salt treatment, without administration of $Br^-$, resulted in a survival probability of only 44% while Br-treatment yielded a survival probability of 67%. Thus, administration of $Br^-$ and together increased the survival probability of 52% as compared to administration of alone (FIG. 1).

Example 3

Figure 2:
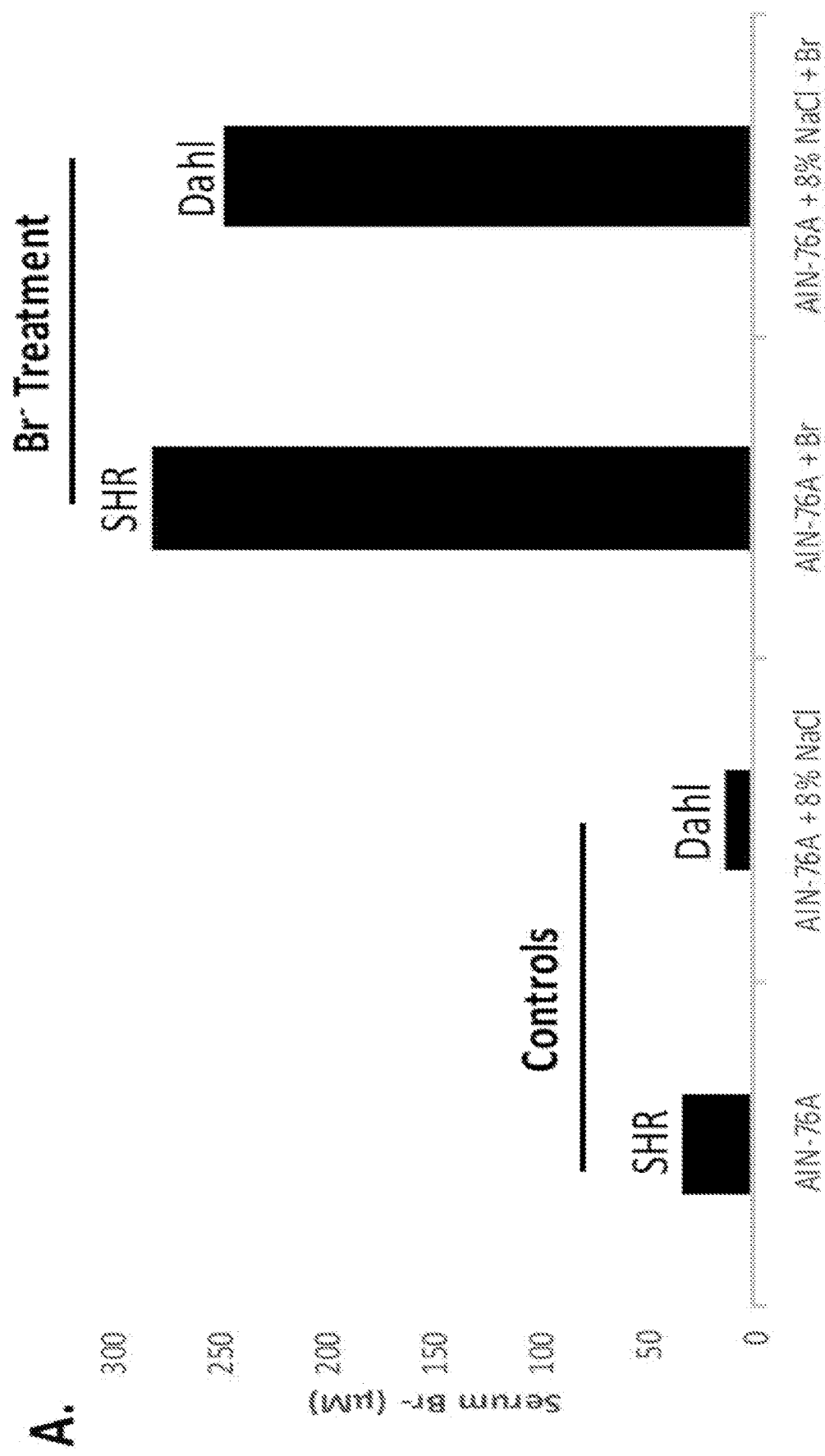
FIG. 2 shows evidence of safe administration of embodiments of the invention in repeat dosing studies in rats. (A) Serum $Br^-$ concentrations from rats fed a daily diet over 10 weeks of "AIN-76A", "AIN-76A+8% NaCl", "AIN-76A+Br", or "AIN-76A+8% NaCl+Br". Salt sensitive Dahl rats as well as Spontaneously Hypertensive Rats (SHR) were used in these studies. The two diets containing 8% NaCl (eg. "AIN-76A+8% NaCl" and "AIN-76A+8% NaCl+Br") were fed to Dahl rats while the remaining two diets (eg. "AIN-76A" and "AIN-76A+Br") were fed to SHR, as indicated in panel A. Serum $Br^-$ measurements were determined using mass spectrometry. Importantly, both $Br^-$ treatments (eg. "AIN-76A+Br" nor "AIN-76A+85 NaCl+Br") resulted in non-toxic serum $Br^-$ concentrations, indicating that embodiments of the invention can safety harness the therapeutic potential of $Br^-$. (B) Actual Br— levels (final) were determined in AIN-76A, AIN-76A+8% NaCl, AIN-76A+Br, or AIN-76A+8% NaCl+Br diets using epiboron instrumental neutron activation analysis. (C) Embodiments of the invention administer safe amounts of $Br^-$ to subjects, targeting those circulating $Br^-$ concentrations that exhibit no observed adverse effects, which distinguishes these embodiments from other Br-containing drugs that raise circulating $Br^-$ concentrations to toxic levels. Not to scale.

Dahl rats are known to exhibit salt-sensitive hypertension and kidney disease. To test the invention, a group of Dahl rats was administered AIN76A supplemented with 8% NaCl and 300 mg NaBr per kg of food. Considering that the rat body weights increased from around 300 g to around 400 g over the course of the study, and assuming that the rats ate a relatively constant amount of 25 g of food per day, the daily consumption of $Br^-$ ranged from approximately 14.6 to 19.4 mg $Br^-$ per kg body weight, in accordance with the invention. Rats receiving $Br^-$ and high salt displayed a mean serum $Br^-$ of 246.50 µM at the end of the study (FIG. 2). Thus, the invention succeeded in providing a nutritionally effective amount of $Br^-$ to the rats in the presence of a high salt diet.

Example 4

Safety of the invention was demonstrated in spontaneously hypertensive rats (SHR). Rats were administered 10 mg of NaBr per kg of AIN76A diet for 10 weeks. At the end of the study, serum $Br^-$ levels in Br-treated rats were compared to serum $Br^-$ levels in SHR on AIN76A as well as Wistar rats on AIN76A. Administration of the invention resulted in a mean serum $Br^-$ of 281.7 µM (±34.9 µM), while AIN76A-treated SHR displayed 33.1 µM (±5.4 µM) and Wistar rats on AIN76A diet displayed serum $Br^-$ levels of 29.6 µM (±3.1 µM) (FIG. 2). The serum $Br^-$ levels in the Br-treated rats are below the toxicity threshold of 12 mM serum $Br^-$ in humans. Considering that the invention was administered for 10 weeks, it can be assumed that the end-of-study serum $Br^-$ measurements reflect a steady-state level. Moreover, in the situation that the invention is administered to a patient being treated with dialysis, it can be further assumed that the $Br^-$ administered through the invention would be removed from the patient at the next dialysis treatment. Thus, this data supports the position that the invention is reasonably safe for administration.

Example 5

To validate the potential cardioprotective effects of $Br^-$ observed in Dahl rats, the inventors turned to the spontaneously hypertensive rat (SHR) model of cardiovascular disease. Eight SHR animals received AIN76A diet for 10 weeks while 8 SHR animals received AIN76A supplemented with 10 mg NaBr/kg diet. No treatment-induced mortality or electrolyte disturbances were detected. Br-treatment significantly reduced the absolute heart weight, and this trend was preserved when heart weight was adjusted to rat body weight (FIG. 3). After 1 day on study diet, urinary protein levels were significantly lower in rats receiving Br⁻, a difference that persisted through the end of the study (FIG. 3).

Following conclusion of the in vivo study, rat hearts were formalin-fixed, paraffin-embedded, and 5 μm-thick sections were obtained for histochemical analysis. Masson's Trichrome staining revealed dramatic reduction in blue staining in Br-treated hearts compared to SHR on AIN76A diet, suggesting that Br⁻ prevented the progression of fibrosis in cardiac tissue (FIG. 4).

Example 6

The inventors next asked whether Br⁻ exerts any short-term activity in addition to the improved cardiac fibrosis noted after 10 weeks administration. Returning to the SHR preclinical model of disease, the inventors specifically asked whether Br⁻ administration modulates certain biomarkers associated with cardiovascular disease at one day post-administration. To this end, Br⁻ was administered to 8 SHR via intraperitoneal (IP) injection with an estimated 0.154 μg NaBr per gram body weight. For control, 8 SHR were administered saline via IP injection containing an estimated 4 ng NaBr per gram body weight. At one day post-administration, Br-treated rats exhibited statistically significant reductions in systolic blood (FIG. 5). Moreover, Br-treated rats displayed a statistically significant increase in serum brain natriuretic peptide (BNP; FIG. 6). Without wishing to be bound by theory, embodiments as described herein can therapeutically improve certain hemodynamic and circulating biomarkers that are associated with progression of cardiovascular and kidney diseases. Moreover, Br⁻ achieves its cardiovascular and renal therapeutic activities in part via modulation of natriuretic peptide signaling.

REFERENCES

The following references are hereby each incorporated by reference in its entirety.
Addison, *Can. Med. Assoc. J.,* 18(3), 1928.
Akomeah et al., *Eur. J. Pharm. Sci.,* 21(2-3):337, 2004.
Aouacheria et al., *Mol. Biol. Evol.,* 23:2288, 2006.
Baird-Heinz, et al., *J. Am. Vet. Med. Assoc.,* 2012
Bhave et al., *Nat. Chem. Biol.,* 8(9):784, 2012.
Barratt and Walser, *J. Clin. Invest.,* 48:56, 1969.
Baxter and Mitragotri, *J. Control. Release,* 106(3):361, 2005.
Bevc et al., *Acta Dermatovenerol APA,* 15(4):151, 2006
Borza et al., *J. Biol. Chem.,* 280:27147, 2005.
Bramson et al., *Gene Ther.,* 10(3):251, 2003.
Brodie et al., *J. Biol. Chem.,* 130:555, 1939.
Burnier et al. *Oncogene,* 30:3766-3783, 2011.
Canavese et al., *Am. J. Kidney Dis.,* 48(6):1018, 2006.
Cao et al., *Clin. Interv. Aging,* 10:55, 2015
Cheng et al., *Free Radic. Biol. Med.,* 45:1682, 2008.
Cho-Chung, *Curr. Pharm. Des.,* 11(22):2811-2823, 2005.
Chun and Uitto, *Dermatol. Clin.,* 28(1):93, 2010.
Cope et al., *J. American Chemical Soc.,* 82:4663, 1960.
Cortez et al., *Arch. Biochem. Biophys.,* 254(2):504, 1987.
Cummings et al., *J. Cell. Biol.,* 213(4):479, 2016.
Daley and Yamada, *Curr. Opin. Genet. Dev.,* 23:408-414, 2013.
Davis et al., *Biomaterials,* 33(28):6691, 2012.
Dobbie et al., *Adv. Peritoneal Dial.,* 6:3 1990.
Eli Lilly and Co. Hand Book of Pharmacy and Therapeutics, 1920.
Fidler et al., *Proc. Natl. Acad. Sci. U.S.A.,* 111(1):331, 2014.
Fox et al., *Cell,* 129:179, 2007.
Fu et al., *J. Biol. Chem.,* 288(11):7430, 2013.
Gilchrist and Moody, *Chemical Rev.,* 77:409, 1977.
Glass and Duchek, *J. American Chemical Soc.,* 98:965, 1976.
Glibowicka et al., *Biochem. Biophys. Acta.,* 946:345, 1988.
Gotenstein et al., *Development,* 137(21):3603, 2010.
Gould et al., *N Engl. J. Med.,* 354:1489, 2006.
Gould et al., *Science,* 308:1167, 2005.
Gupta et al., *J. Cell. Biol.,* 137(5):1185, 1997.
Haenlein and Anke, *Small Rumin. Res.,* 95:2, 2011.
Hasuike et al., *Nephrol. Dial. Transplant.,* 19(6):1474, 2004.
He et al., *J. Am. Soc. Nephrol.,* 27(4):1202, 2016.
Hudson et al., *N Engl. J. Med.,* 348:2543, 2003.
Hynes, *Cell,* 110:673, 2002.
Kay et al., *J. American Chemical Soc.,* 114:10663, 1992.
Kennedy et al, *Hypertension,* 47:488-495, 2006.
Khan et al., *Am. J. Hum. Genet.,* 89(3):464, 2011.
Khoshnoodi et al., *J. Biol. Chem.,* 281:6058, 2006.
Khoshnoodi et al., *Microsc. Res. Tech.,* 71:357, 2008.
Kivirikko and Pihlajaniemi, *Adv. Enzymol. Relat. Areas Mol. Biol.,* 72:325, 1998.
Kleinewietfeld et al., *Nature,* 469(7446): 518, 2013.
Kubieck-Sutherland et al., *EBioMedicine,* 2(9):1169, 2015.
Kuo, et al., *Hum. Mol. Genet.,* 21(R1):R97, 2012.
Lagerwerf et al., *Rapid Commun. Mass Spectrom.,* 10:1905, 1996.
Lambeth and Swank, *Federation Proc.,* 38:830, 1979.
Lee et al., *Nephrol. Dial. Tranplant.,* 23:1005, 2008.
Licklider et al., *Anal. Chem.,* 74:3076, 2002.
Lopez et al., *J. Am. Col. Coll Cardiol.,* 65:2449-2456, 2015.
Lourenco et al., *Eur. J. Heart Fail.* 11(2), 2009.
Malara et al., *Stem Cells,* 32:926, 2014.
Marcinkiewicz et al., *Adv. Exp. Med. Biol.,* 643:439, 2009.
Masago et al., *Oncol. Lett.,* 2(2):253-247, 2011.
Matias et al., *Port. J. Nephrol. Hypert.,* 23(2):161-166, 2009.
Matsue et al., *J. Card. Fail.,* 21(11):859-864, 2015.
Maya and Villareal, *J. Mol. Cell. Cardiol.,* 48(3):524-529, 2010.
McCall et al., *Cell* 157(6):1380, 2014.
Mertz, *Science,* 213:1332, 1981.
Miura et al., *Nucl. Instr. and Meth. in Phys. Res. B,* 189:443, 2002.
Moser et al., *Science,* 324:895, 2009.
Nambi et al., *Eur. Heart J.,* 33:183, 2012.
Nathan et al., *J. Am. Coll. Cardiol.,* 57(8):891-903, 2011.
Naughton, *Am. Fam. Physician,* 78(6):743-750, 2008.
Nelson et al., *Embo J.,* 13:3438, 1994.
NICE Guideline, "Chronic kidney disease in adults: assessment and management (CG182), 2014
Ochi et al., *Biol. Trace Elem. Res.,* 143:825, 2011.
Ogawa et al., *Protein Sci.,* 19(3):544-557, 2010.
Palmer et al., *J. Magnetic Resonance,* 93:151, 1991.
Parkin et al., *Hum. Mut.,* 32(2):127, 2011.
Pastor-Pareja and Xu, *Dev. Cell,* 21(2):245, 2011.
Pavelka et al., *Physiol. Res.,* 54:639, 2005.
Pitt and Zannad, *Circulation: Cardiovascular Imaging,* 5:9-11, 2012.
Podell et al., *J. Vet. Intern. Med.,* 7(5):318, 1993.
Poschl et. al., *Development,* 131(7):1619, 2004
Reid et al., *J. Proteome Res.,* 3:751, 2004.
Reule & Drawz, *Curr. Hypertens. Rep.,* 14(6), 2012.

Sackner-Bernstein et al., *Circulation*, 111(12):1487-1491, 2005
Sackner-Bernstein et al., *JAMA*, 293(15):1900-1905, 2005
Sakaguchi et al., *Kidney International*, 85:174, 2013.
Sakaguchi et al., *PLoS One*, 9(12):e116273, 2014.
Saraswat et al., *Indian J. Pharm. Sci.*, 71(5):488-498, 2009.
Sawala, et al., *Proc. Nat. Acad. Sci. U.S.A.*, 109:11222, 2012.
Schleucher et al., *J. Biomol. NMR*, 4:301, 1994.
Schlueter et al., *Pharmacol. Ther.*, 144(1):12-27, 2014.
Serafino and Pierimarchi, *Curr. Med. Chem.*, 21(21):2401-2409, 2014
Shroff et al., *Circulation*, 118:1748, 2008.
Siebold et al., *Eur. J. Biochem.*, 176:617, 1988.
Senthilmohan and Kettle, *Arch. Biochem. Biophys.*, 446(2):235, 2006.
Song and Ott, *Trends Mol. Med.*, 17(8):424, 2011.
Springer et al., *J. Mol. Cell Cardiol.*, 52(5):1122, 2012
Strejan et al., *Prog Clin Biol Res.*, 146:429, 1984.
Sundaramoorthy et al., *J. Biol. Chem.*, 277:31142, 2002.
Tektas and Lutjen-Drecol, *Exp. Eye Res.*, 88(4):769, 2009.
Than et al., *Biological Chemistry*, 386:759, 2005.
Than et al., *Proc. Natl. Acad. Sci. USA*, 99:6607, 2002.
Thorner et al., *J. Biol. Chem.*, 271:13821, 1996.
Timpl et al., *Eur. J. Biochem.*, 120(2):203, 1981.
Torii et al., *Psychopharmacologia (Berl.)*, 29:65, 1973.
Trautner and Wieth, *Acta. Physiol. Scand.*, 74:606, 1968.
Travers et al., *Circ. Res.*, 118:1021-1040, 2016.
Trepanier et al., *J. Am. Vet. Med. Assoc.*, 213(10):1449, 1998
Tsuge et al., *J. Health Sci.*, 46(5): 343, 2000.
Tuqan et al., *Lasers Med. Sci.*, 20(2):80, 2005.
United States Pharmacopeial Convention, "Sodium Chloride" monograph, *Pharmcopeial Forum*, 28(4), July-August, 2002.
USRDS, Annual Data Report, 2013.
Van Leeuwen and Sangster, *Toxicol.*, 18(3):189, 1987.
Van Renterghem et al., *J. Trace Elem. Electrolytes Health Dis.*, 6:105, 1992.
Vanacore et al., *J. Biol. Chem.*, 279:44723, 2004.
Vanacore et al., *J. Biol. Chem.*, 280:29300, 2005.
Vanacore et al., *J. Biol. Chem.*, 283:22737, 2008.
Vanacore et al., *Science*, 325(5945):1230, 2009.
Vesely, *Anticancer Res.*, 34(4):1459-1466, 2014.
Vobecky et al., *Biol. Trace Elem. Res.*, 103:37, 2005.
Vracko, *Am. J. Pathol.*, 77:314, 1974
Wallaeys et al., *Kidney Int.*, 30:599, 1986.
Wang et al., *Nature*, 455(7209):72-77, 2008.
Weber et al., *Eur. J. Biochem.*, 139:401, 1984.
Weber et al., *Nucl. Instr. and Meth. in Phys. Res. B3*, 326, 1984.
Weil et al., *Pediatrics*, 80(4): 545-548, 1987.
Willker et al., *Magnetic Resonance in Chemistry*, 31:287, 1993.
Wolf and Eadie, *Am. J. Physiol.*, 163:436, 1950.
Yap et al., *Tissue Eng. Part A*, 19(21,22):2361, 2013.
Yates et al., *Anal. Chem.*, 67:1426, 1995.
Yamane et al., *J. Neurochem.*, 1984
Yan et al., *Hum. Mol. Genet.*, 23(21):5597, 2014.
Yanagisawa and Torii, *Tohuko J. Exp. Med.*, 2002.
Yanagisawa and Yoshikawa, *Biochem. Biophys. Acta*, 329: 283, 1973.
Yunos et al. *Critical Care*, 14:226, 2010.
Yurchenko, *Cold Spring Harb. Perspect. Biol.*, 3(2): a004911, 2011
Yurchenco and Furthmayr, *Biochemistry*, 23:1839, 1984.

---

What is claimed is:

1. An oral pharmaceutical composition, the composition consisting of an amount between about 1 mg and about 250 mg of Br—, a pharmaceutically acceptable carrier or salt thereof, and one or more pharmaceutical drug(s) selected from the group consisting of a cardiovascular disease treating agent, a kidney disease treating agent, or an anti-diabetic agent.

2. The composition of claim 1, wherein the bromide source comprises sodium bromide, potassium bromide, magnesium bromide, or a combination thereof.

3. The composition of claim 1, wherein the cardiovascular disease treating agent is a blood pressure controlling agent, angiotensin-converting enzyme inhibitor, angiotensin receptor blocker, beta blocking agent, alpha blocking agent, antiarrhythmic agent, blood thinner, alpha agonist, sodium channel blocking agent, calcium channel blocking agent, antiplatelet agent, antihyperlipidemic agent, statin therapy, nonsteroidal anti-inflammatory drug, loop diuretic, thiazide diuretic, potassium-sparing diuretic, vasodilator, renin inhibitor, dopamine, dopamine receptor agonist, or a thrombolytic agent.

4. The composition of claim 1, wherein the kidney disease treating agent is erythropoietin or an erythropoietic stimulating agent.

5. The composition of claim 1, wherein the anti-diabetic agent is an insulin, insulin-combination drug, amylinomimetic agent, alpha-glucosidase inhibitor, pramlintide, acarbose, miglitol, biguanide, glucagon-like peptide, meglitinide, sodium glucose transporter 2 inhibitor, sulfonylurea, thiazolidinedione, dipeptidyl peptidase-4 inhibitor, metformin, metformin-containing drug, bromocriptine, alogliptin, alogliptin-pioglitazone, linagliptin, linagliptin-empagliflozin, sitagliptin and simvastatin, albiglutide, dulaglutide, exenatide, exenatide extended-release, liraglutide, nateglinide, repaglinide, dapagliflozin, canaglifoxin, empaglifozin, empagliflozin-linagliptin, glimepiride, glimepiride-pioglitazone, glimepiride-rosiglitazone, gliclazide, glipizide, glyburide, chlorpropamide, tolazamide, tolbutamide, rosiglitazone, or pioglitazone.

* * * * *

SEQUENCE LISTING

```
<160> NUMBER OF SEQ ID NOS: 2

<210> SEQ ID NO 1
<211> LENGTH: 28
<212> TYPE: PRT
<213> ORGANISM: Unknown
<220> FEATURE:
<223> OTHER INFORMATION: Description of Unknown:
      Atrial natriuretic peptide (ANP) sequence

<400> SEQUENCE: 1

Ser Leu Arg Arg Ser Ser Cys Phe Gly Gly Arg Met Asp Arg Ile Gly
1               5                   10                  15

Ala Gln Ser Gly Leu Gly Cys Asn Ser Phe Arg Tyr
            20                  25

<210> SEQ ID NO 2
<211> LENGTH: 32
<212> TYPE: PRT
<213> ORGANISM: Unknown
<220> FEATURE:
<223> OTHER INFORMATION: Description of Unknown:
      Brain natriuretic peptide (BNP) sequence

<400> SEQUENCE: 2

Ser Pro Lys Met Val Gln Gly Ser Gly Cys Phe Gly Arg Lys Met Asp
1               5                   10                  15

Arg Ile Ser Ser Ser Ser Gly Leu Gly Cys Lys Val Leu Arg Arg His
            20                  25                  30
```